United States Patent
LaVoie et al.

(10) Patent No.: US 11,091,498 B2
(45) Date of Patent: Aug. 17, 2021

(54) TOPOISOMERASE POISONS

(71) Applicant: Rutgers, The State University of New Jersey, New Brunswick, NJ (US)

(72) Inventors: Edmond J. LaVoie, New Brunswick, NJ (US); Ajit K. Parhi, New Brunswick, NJ (US)

(73) Assignee: Rutgers, The State University of New Jersey, New Brunswick, NJ (US)

(*) Notice: Subject to any disclaimer, the term of this patent is extended or adjusted under 35 U.S.C. 154(b) by 0 days.

(21) Appl. No.: 16/090,802

(22) PCT Filed: Apr. 3, 2017

(86) PCT No.: PCT/US2017/025779
§ 371 (c)(1),
(2) Date: Oct. 2, 2018

(87) PCT Pub. No.: WO2017/176648
PCT Pub. Date: Oct. 12, 2017

(65) Prior Publication Data
US 2020/0325149 A1  Oct. 15, 2020

Related U.S. Application Data

(60) Provisional application No. 62/318,139, filed on Apr. 4, 2016.

(51) Int. Cl.
*C07D 491/147* (2006.01)
*C07D 519/00* (2006.01)
*A61P 35/04* (2006.01)

(52) U.S. Cl.
CPC .......... *C07D 491/147* (2013.01); *A61P 35/04* (2018.01); *C07D 519/00* (2013.01)

(58) Field of Classification Search
CPC .......................... C07D 491/147; C07D 519/00
See application file for complete search history.

(56) References Cited

U.S. PATENT DOCUMENTS

| | | |
|---|---|---|
| 2,915,523 A | 12/1959 | Elslager et al. |
| 2,981,731 A | 4/1961 | Moore et al. |
| 2,985,661 A | 5/1961 | Alheim et al. |
| 3,267,107 A | 8/1966 | Sallay et al. |
| 3,272,707 A | 9/1966 | Tedeschi et al. |
| 3,449,330 A | 6/1969 | Maeder et al. |
| 3,538,097 A | 11/1970 | Lammler et al. |
| 3,542,782 A | 11/1970 | Houlihan et al. |
| 3,849,561 A | 11/1974 | Ikeda et al. |
| 3,884,911 A | 5/1975 | Shimada |
| 3,912,740 A | 10/1975 | Zee-Cheng et al. |
| 4,749,708 A | 6/1988 | Maroko |
| 4,761,417 A | 8/1988 | Maroko |
| 4,761,477 A | 8/1988 | Ikekawa et al. |
| 4,925,943 A | 5/1990 | Kanmacher et al. |
| 4,980,344 A | 12/1990 | Maroko |
| 5,106,863 A | 4/1992 | Hajos et al. |
| 5,126,351 A | 6/1992 | Luzzio et al. |
| 5,153,178 A | 10/1992 | Maroko |
| 5,190,753 A | 3/1993 | Behrens et al. |
| 5,244,903 A | 9/1993 | Wall et al. |
| 5,318,976 A | 6/1994 | Luzzi et al. |
| 5,639,759 A | 6/1997 | Magolda et al. |
| 5,646,283 A | 7/1997 | Suzuki et al. |
| 5,767,142 A | 6/1998 | Lavoie et al. |
| 5,770,617 A | 6/1998 | Lavoie et al. |
| 5,807,874 A | 9/1998 | Lavoie et al. |
| 5,981,541 A | 11/1999 | Lavoie et al. |
| 6,140,328 A | 10/2000 | Lavoie et al. |
| 6,486,167 B1 | 11/2002 | La et al. |
| 6,509,344 B1 | 1/2003 | Cushman et al. |
| 6,740,650 B2 | 5/2004 | Lavoie et al. |
| 6,964,964 B2 | 11/2005 | Lavoie et al. |
| 6,987,109 B2 | 1/2006 | Lavoie et al. |

(Continued)

FOREIGN PATENT DOCUMENTS

| | | |
|---|---|---|
| EP | 0108147 B1 | 8/1988 |
| EP | 0496634 A1 | 7/1992 |

(Continued)

OTHER PUBLICATIONS

Steverding et al. (Medical Mycology, 2012, 50, pp. 333-336).*
Aguirre, J., et al., "Reaction of 1,2-diarylethylamides with ethyl polyphosphate(EPP): correlation of the von Braun, Ritter and Bischler-Napieralski reactions", Chemical Abstracts, 111(13), Abstract No. 115004, 656 (1989).
Akiyama, et al., "Isolation and Genetic Characterization of Human KB Cell Lines Resistant to Multiple Drugs", Somatic Cell and Molecular Genetics, vol. 11, No. 2, 117-126 (1985).
Andoh, et al., "Characterization of a mammalian mutant with a camptothecin-resistant DNA topoisomerase I", Proc. Natl. Acad. Sci., vol. 84, 5565-5569 (1987).

(Continued)

*Primary Examiner* — Susanna Moore
(74) *Attorney, Agent, or Firm* — Viksnins Harris Padys Malen LLP

(57) ABSTRACT

Provided herein are compounds of formula (I): and salts thereof. Also provided are pharmaceutical compositions comprising a compound of formula (I), processes for preparing compounds of formula (I), intermediates useful for preparing compounds of formula (I), and therapeutic methods for treating diseases such as cancer, a bacterial infection or a fungal infection using compounds of formula (I).

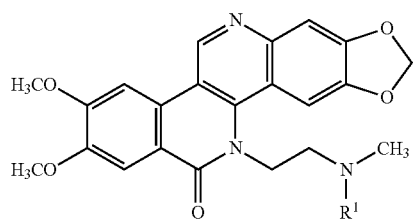

18 Claims, No Drawings

(56) References Cited

U.S. PATENT DOCUMENTS

| | | |
|---|---|---|
| 6,989,387 B2 | 1/2006 | Lavoie et al. |
| 6,992,088 B2 | 1/2006 | Lavoie et al. |
| 6,992,089 B2 | 1/2006 | Lavoie et al. |
| 7,049,315 B2 | 5/2006 | Lavoie et al. |
| 7,208,492 B2 | 4/2007 | Lavoie et al. |
| 7,319,105 B2 | 1/2008 | Lavoie et al. |
| 7,468,366 B2 | 12/2008 | Lavoie et al. |
| 7,517,867 B2 | 4/2009 | Lavoie et al. |
| 7,517,883 B2 | 4/2009 | Lavoie et al. |
| 7,781,587 B2 | 8/2010 | Lavoie et al. |
| 7,858,627 B2 | 12/2010 | Lavoie et al. |
| 8,389,721 B2 | 3/2013 | Lavoie et al. |
| 9,321,781 B2 | 4/2016 | Lavoie et al. |
| 9,562,051 B2 | 2/2017 | Lavoie et al. |
| 10,179,789 B2 | 1/2019 | Lavoie et al. |
| 2004/0102443 A1 | 5/2004 | Lavoie et al. |
| 2004/0110760 A1 | 6/2004 | Lavoie et al. |
| 2004/0110782 A1 | 6/2004 | Lavoie et al. |
| 2005/0009824 A1 | 1/2005 | Lavoie et al. |
| 2005/0009825 A1 | 1/2005 | Lavoie et al. |
| 2005/0009826 A1 | 1/2005 | Lavoie et al. |
| 2005/0009830 A1 | 1/2005 | Lavoie et al. |
| 2005/0010046 A1 | 1/2005 | Lavoie et al. |
| 2006/0058306 A1 | 3/2006 | Lavoie et al. |
| 2007/0015751 A1 | 1/2007 | Lavoie et al. |
| 2008/0045538 A1 | 2/2008 | Lavoie et al. |
| 2008/0214576 A1 | 9/2008 | Matteucci et al. |
| 2010/0240664 A1 | 9/2010 | Lavoie et al. |
| 2011/0136812 A1 | 6/2011 | Lavoie et al. |
| 2012/0004235 A1 | 1/2012 | Lavoie et al. |
| 2012/0101117 A1 | 4/2012 | Lavoie et al. |
| 2013/0280282 A1 | 10/2013 | Ohtsuka et al. |
| 2013/0303778 A1 | 11/2013 | Matteucci et al. |

FOREIGN PATENT DOCUMENTS

| | | |
|---|---|---|
| GB | 2108955 A | 5/1983 |
| SU | 1530628 A1 | 12/1989 |
| WO | 1992021661 A1 | 12/1992 |
| WO | 1996036612 A1 | 11/1996 |
| WO | 1997029106 A1 | 8/1997 |
| WO | 1998012181 A1 | 3/1998 |
| WO | 1998031673 A1 | 7/1998 |
| WO | 1999031067 A1 | 6/1999 |
| WO | 2000021537 A1 | 4/2000 |
| WO | 2001032631 A2 | 5/2001 |
| WO | 2003041660 A2 | 5/2003 |
| WO | 2003047505 A2 | 6/2003 |
| WO | 2004014918 A1 | 2/2004 |
| WO | 2004044174 A2 | 5/2004 |
| WO | 2005081711 A2 | 9/2005 |
| WO | 2006065448 A2 | 6/2006 |
| WO | 2007002931 A2 | 1/2007 |
| WO | 2008103693 A2 | 8/2008 |
| WO | 2008141044 A2 | 11/2008 |
| WO | 2013173337 A2 | 11/2013 |
| WO | 2014164503 A1 | 10/2014 |

OTHER PUBLICATIONS

Andoh , "Drug Resistance Mechanisms of Topoisomerase / Drugs", Advances in Pharmacology, vol. 29B, DNA Topoisomerases: Topoisomerase—Targeting Drugs, 93-103 (1994).

Arumugam , et al., "Synthesis of 7, 8-Benzophenanthridines", Indian Journal of Chemistry, vol. 12, 664-667 (1974).

Badia , et al., "Silicon-mediated isoquinoline synthesis: preparation and stereochemical characterization of 4-hydroxy-3-phenylisoquinolines", Chemical Abstracts, vol. 117 (13), Abstract No. 131034, 730 (1992).

Baezner , "Conversion of o-nitro and o,p-dinitrobenzylchlroide into acridinic derivatives", 2438-2447 (1906) [with English Abstract].

Baezner , "Conversion of o-nitrobenzyl chloride and o,p-dinitrobenzyl chloride into acridine derivatives", 3077-3083 (1904) [with English Abstract].

Baguley, D , et al., "Anticancer Drug Development", p. 148, Scheme 17 Activation of 2-nitro-imidazolylcarbamates self-immolative prodrugs by NR, 2 p. 2 (2001).

Bhakuni, D , et al., "Protoberberine Alkaloids", The Alkaloids, vol. 28, Chapter 2, Academic Press, Inc., 95-181 (1986).

Bjornsit, M , et al., "Expression of human DNA topoisomerase I in yeast cells lacking yeast DNA topoisomerase I: restoration of sensitivity of the cells to the antitumor drug camptothecin", Cancer Research, 49, 6318-6323 (1989).

Bradsher, C , et al., "Alpha-Acyl-o-tolunitriles as intermediates in the preparation of 3-substituted isoquinolines and 1-amino-2-benzopyrylium derivatives", Chemical Abstracts, 89(21), Abstract No. 89: 179810b, 590 (1978).

Brossi, A , "Benzo[c]phenanthridine Alkaloids", The Alkaloids, Chemistry and Pharmacology, vol. XXV, Academic Press, Inc., 178-199 (1985).

Buu-Hoi, N , et al., "Carcinogenic Nitrogen Compounds. XV. Polysubstituted Angular Benacridines and Benzophenarsazines", Chemical Abstracts, 49(1), Abstract, col. 330, 10—Organic Chemistry, 329-330 (1955).

Buu-Hoi, N , "The chemistry of carcinogenic nitrogen compounds. Part V. Angular hydroxybenzacridines and hydroxdibenzacridines", Journal of the Chemical Society, Letchworth GB, (1950), 2096-2099 (1950).

Buu-Hoi, N , et al., "The Chemistry of Carcinogenic Nitrogen Compounds. Part X. The Pfitzinger Reaction in the Synthesis of 1:2-Benzacridines", Journal of the Chemical Society, Letchworth, GB, 279-281 (1952).

Carmichael, J , "Evaluation of a tetrazolium-based semiautomated colorimetric assay: assessment of chemosensitivity testing", Cancer Research, 47, 936-42 (1987).

Cecil Textbook of Medicine , edited by Bennet, J.C. and Plum F., 20th Edition, vol. 1, 1004-1010 (1996).

Chen, A , "A new mammalian DNA topoisomerase I poison Hoechst 33342: cytotoxicity and drug resistance in human cell cultures", Cancer Research, 53(6), 1332-1337 (1993).

Chen , et al., "DNA Minor Groove-Binding Ligands: A Different Class of Mammalian DNA Topoisomerase I Inhibitors", Proceedings of the National Academy of Sciences, 90, 8131-8135 (1993).

Chen , et al., "DNA Topoisomerases: Essential Enzymes and Lethal Targets", Annu. Rev. Pharmacol. Toxicol., 34, 191-218 (1994).

Cherif, A , et al., "N-(5,5-Diacetoxypent-1-yl)doxorubicin: a new intensely potent doxorubicin analogue", Journal of Medicinal Chemistry, 35, 3208-3214 (1992).

Croisy-Delcey, M , et al., "Synthesis and Carcinogenic Activity of Oxidized Benzacridines: Potential Metabolites of the Strong Carcinogen 7-methylbenz[c]acridine and of the Inactive Isomer 12-methylbenz[a]acridine", Chemical Abstracts, 98, Abstract No. 43798, 27-29 (1983).

Croisy-Delcey, M , et al., "Synthesis and carcinogenic activity of oxidized benzacridines: potential metabolites of the strong carcinogenic 7-methylbenz[c]acridine and of the inactive isomer 12-methylbenz[a]acridine", Journal of Medicinal Chemistry, 26, 303-306 (Abstract) (1983).

Cushman, M , et al., "Synthesis and antitumor activity of structural analogues of the anticancer benzophenanthridine alkaloid fagaronine chloride", Journal of Medicinal Chemistry, 28, 1031-1036 (1985).

Cushman , et al., "Synthesis of New Indeno[1,2-c]isoquinolines: Cytotoxic Non-Camptothecin Topoisomerase I Inhibitors", Journal of Medicinal Chemistry, 43(20), 3688-3698 (2000).

D'Arpa , et al., "Topoisomerase-targeting antitumor drugs", Journal of Medicinal Chemistry, 43(20), 3688-3698 (2000).

Denizot, F , et al., "Rapid colorimetric assay for cell growth and survival. Modifications to the tetrazolium dye procedure giving improved sensitivity and reliability", Journal of Immunological Methods, 89, 271-277 (1986).

Denny , "Emerging DNA topoisomerase inhibitors as anticancer drugs", Expert Opin. Emerg. Drugs, vol. 9(1), 105-133 (2004).

Dominguez, E , et al., "Dehydrogenation reactions of 1-substituted-3-aryltetrahydro-isoquinoline derivatives", Chemical Abstracts, 101(11), Abstract No. 090742z,(1984).

(56) References Cited

OTHER PUBLICATIONS

Dorofeenko, G , et al., "Synthesis of 3-aryl derivatives of 2-benzopyrylium salts with free alpha-positions", Chemical Abstracts, 74 (15), Abstract No. 076295, 432 (1971).
Feng , et al., "11-Substituted 2,3-dimethoxy-8,9-methylenedioxybezo[i]phenanthridine derivatives as novel topoisomerase I-targeting agents", Bioorganic & Medicinal Chemistry 16, 8598-8606 (2008).
Feng, W , et al., "Synthesis of N-substituted 5-[2-(N-alkylamino)ethyl]dibenzo[c,h][1,6]-naphthyridines as novel topoisomerase I-targeting antitumor agents", Bioorganic & Medicinal Chemistry 16, 9295-9301 (2008).
Fitzergald, J , et al., "Reaction of benzocyclobutene oxides with nitriles: synthesis of hypecumine and other 3-substituted isoquinolines", Chemical Abstracts, 122(7), Abstract No. 081704, 1128 (1995).
Fox, G , et al., "para-Bromination of Aromatic Amines: 4-Bromo-N,N-Dimethyl-3-(Trifluoromethyl)Aniline", Organic Syntheses, vol. 55, 20-23 (1976).
Fuji, N , et al., "Induction of Mammalian DNA Topoisomerase I-mediated DNA Cleavabe and DNA Winding by Bulgarein", Journal of Biological Chemistry, 268(18), 13160-13165 (1993).
Gallo, R , et al., "Studies on the Antitumor Activity, Mechanism of Action, and Cell Cycle Effects of Camptothecin", Journal of the National Cancer Institute, vol. 46, No. 4, 789-795 (1971).
Garcia, A , et al., "A simple direct approach to 1-substituted 3-arylisoquinolines from deoxybenzoins and nitriles", Chemical Abstracts, 110(25), Abstract No. 23107u, 622 (1989).
Gatto, B , "Identification of Topoisomerase I as the Cyctotoxic Target of the Protoberberine Alkaloid Coralyne", Cancer Research, 56(12), 2795-2800 (1996).
Giovanella, B , et al., "Complete growth inhibition of human cancer xenografts in nude mice by treatment with 20-(S)-camptothecin", Cancer Research, 51(11), 3052-3055 (1991).
Godowski, K , et al., "Free amine benzophenanthridine alkaloid compositions", USPATFULL Database, No. 95:20510, RN No. 218-38-2 (Benzo[c]phenanthradine), from U.S. Pat. No. 5,395,615, (1995), 3 pages.
Goldman, G , et al., "Differential poisoning of human and Aspergillus nidulans DNA topoisomerase I by bi- and terbenzimidazoles", Biochemistry, 36(21), (1997), 6488-6494 (1997).
Golub, T , et al., "Molecular Classification of Cancer: Class Discovery and Clas Prediction by Gene Expression Monitoring", Science 286, 531-537 (1999).
Gopinath, K , et al., "Synthesis of Some 1:2- and 7:8-Benzophenanthridine", Journal of the Chemistry Society, 78(2), 504-509 (1958).
Hahn, F , et al., "Berberine", Antibiotics, Mechanism of Action of Antimicrobial and Antitumor Agents, vol. III, J.W. Corcoran et al., (eds.), Springer-Verlag, 577-584 (1975).
Halligan, B , et al., "Purification and Characterization of a Type II DNA Topoisomerase from Bovine Calf Thymus", The Journal of Biological Chemistry, 260(4), 2475-2482 (1985).
Hoan, N , et al., "Syntheses from o-halogenated anisoles and phenetoles", Chemical Abstracts, 41(20), American Chemical Society, Abstract No. 6571bg, 2 pages (1947).
Hsaing , et al., "Camptothecin Induced Protein-Linked DNA Breaks Via Mammalian DNA Topoisomerase I", J. Biol. Chem., 260 No. 27, 14873-14878 (1985).
Hsiang, Y , et al., "Identification of Mammalian DNA Topoisomerase I as an Intracellular Target of the Anticancer Drug Camptothecin", Cancer Research, 48(7), 1722-1726 (1988).
Iwao, M , et al., "A Regiospecific Synthesis of Carbazoles via Consecutive Palladium-Catalyzed Cross-coupling and Aryne-Mediated Cyclization", Heterocycles, 36, 1483-1488 (1993).
Satyanarayana, M , et al., "Syntheses and biological evaluation of topoisomerase I-targeting agents related to 11-[2-N,N-dimethylamino)ethyl]-2,3-dimethoxy-8,9-methylenedioxy-11H-isoquino[4,3-c]cinnolin-12-one (ARC-31)", Bioorganic & Medicinal Chemistry 16, 7824-7831 (2008).

Schiess, P , et al., "Thermolytic ring opening of acyloxybenzocyclobutenes: an efficient route to 3-substituted Isoquinolines", Chemical Abstracts, 104(19), Abstract No. 168332z, 639 (1986).
Sethi, M , "Enzyme Inhibition VI: Inhibition of Reverse Transcriptase Activity by Protoberberine Alkaloids and Structure-Activity Relationships", Journal of Pharmaceutical Sciences, 72(5), 538-541 (1983).
Shcherbakova, I , et al., "2-Benzopyrilium salts. 35. Synthesis of the natural alkaloid dehydronocoralydine and other substituted salts of dibenzo[a,g] quinolizine", Chemical Abstracts, 112 (19), Abstract No. 179554, 823 (1990).
Shelanski, H , "Acute and Chronic Toxicity Tests on Electrolytic Iron Powder", Bulletin of the National Formulary Committee, XVIII (5-6), 81-87 (1950).
Simplicio , et al., "Prodrugs for amines", Molecules 13, 519-547 (2008).
Singh, S , et al., "Nitro and Amino Substitution in the D-Ring of 5-(2-Dimethylaminoethyl)-2,3-methylenedioxy-5H-dibenzo [c,h] [1,6] naphthyridin-6-ones: Effect on Topoisomerase-I Targeting Activity and Cytotoxicity", Journal of Medicinal Chemistry, 46(11), 2254-2257 (2003).
Singh, M , et al., "Synthesis and Sequence-Specific DNA Binding of a Topoisomerase Inhibitory Analog of Hoechst 33258 Designed for Altered Base and Sequence Recognition", Chem. Res. Toxicol., 5, 597-607 (1992).
Sotomayor, N , et al., "Oxidation reactions of 2'-functionalized 3-aryltetrahydro-and 3,4-dihydroisoquinolines", Chemical Abstracts, 124 (11), Abstract No. 145854, 1227 (1996).
Southard, G , et al., "Drug Delivery Devices", USPATFULL Database, No. 91:36238, RN No. 218-38-2 (Benzo[c]phenanthradine), from U.S. Pat. No. 5,013,553, 2 pages (1991).
Stermitz, F , "Synthesis and Biological Activity of Some Antitumor Benzophenanthridinum Salts", Journal of Medicinal Chemistry, 18(7), 708-713 (1975).
Studier, F , et al., "Use of T7 RNA polymerase to direct expression of cloned genes", Methods in Enzymology, 185, 60-89 (1990).
Sun, Q , et al., "Structure activity of novel topoisomerase I inhibitors related to Hoechst 33342", Abstract 6—Proceedings of the American Association of Pharmaceutical Scientists Eastern Regional Meeting, Hyatt Regency Hotel, New Brunswick, NJ, p. 25 (Jun. 5-6, 1995).
Sun, Q , et al., "Structure Activity of Topoisomerase I Poisons Related to Hoechst 33342", Bioorganic & MedicinaL Chemistry Letters, 4 (24), 2871-2876 (1994).
Sun, Q , et al., "Structure-activity studies related to minor groove-binding ligands which inhibit mammalian DNA topoisomerase I", Cancer Institute of New Jersey's First Annual Scientific Retreat, Abstract 2, Princeton Marriott Forrestal Village, Princeton, NJ, p. 66 (Jun. 7, 1994).
Sun, Q , et al., "Synthesis and Evaluation of Terbenzimidazoles as Topoisomerase I Inhibitors", Chemical Abstracts, vol. 123, No. 15, Abstract No. 198740r, 1241 (1995).
Sun, Q , et al., "Synthesis and evaluation of terbenzimidazoles as topoisomerase I inhibitors", Journal of Medicinal Chemistry, 38(18), 3638-3644 (1995).
Sun, Q , et al., "Synthesis and pharmacological evaluation of a series of novel DNA topoisomerase I inhibitors as antitumor agents", Abstract 5—Proceedings of the 3rd Annual Scientific Retreat of the Cancer Institute of New Jersey, Princeton Marriott Forrestal Village, Princeton, NJ, p. 27 (1995).
Sun, Q , et al., "Synthesis and Pharmacological Evaluation of a Series of Novel DNA Topoisomerase I Inhibitors as Antitumor Agents", Scientific Proceedings of 86th Annual Meeting of the American Association for Cancer Research, Abstract 3, vol. 36, Toronto, Canada, 2688 (Mar. 1995).
Sun, Q , et al., "Synthesis of Benzimidazo[2,1-a]isoquinolines", Syn. Lett., submitted, Paper No. 7, 6 pages (1995).
Tamura, H , et al., "Molecular cloning of a cDNA of a camptothecin-resistant human DNA topoisomerase I and identification of mutation sites", Nucleic Acids Research, 19 (1), 69-75 (1991).

(56) References Cited

OTHER PUBLICATIONS

Tewey, K , et al., "Adriamycin-induced DNA damage mediated by mammalian DNA topoisomerase II", Science, 226 (4673), 466-8 (1984).
Vinogradov, A , et al., "Some properties of new DNA specific bisbenzimidazole fluorochromes without a piperazine ring", Biotechnic & Histochemistry, 68 (5), 265-270 (1993).
Walterova, D , et al., "Isolation, Chemistry and Biology of Alkaloids from plants of Papaveraceae. Part XCV. Practical application of isotachophoresis in analysis of isoquinoline alkaloids", Chemical Abstract, vol. 104, No. 12, No. 95573, (1986).
Wang, L , et al., "Inhibition of Topoisomerase I Function by Coralyne and 5,6-Dihydrocoralyne", Chem. Res. Toxicol., 9, 75-83 (1996).
Wang, L , et al., "Inhibition of Topoisomerase I Function by Nitidine and Fagaronine", Chem. Res. Toxicol., 6, 813-818 (1993).
Wang, H , et al., "Stimulation of topoisomerase II-mediated DNA damage via a mechanism involving protein thiolation", Biochemistry, 40(11), 3316-3323 (2001).
Waters, W , et al., "Reactions of Free Benzyl Radicals with Benz[a]- and Benz[c]acridine", Chemical Abstracts, 54(4), Abstract, col. 3424b, (1960).
Wilson, W , et al., "Coralyne. Intercalation with DNA as a Possible Mechanism of Antileukemic Action", Journal of Medicinal Chemistry, 19(10), Communications to the Editor, 1261-1263 (1976).
Yadagiri, B , et al., "Convenient Routes to Substituted Benzimidazoles and Imidazolo[4,5-b]pyridines Using Nitrobenzene as Oxidant", Synthetic Communications, 20 (7), 955-963 (1990).
Yamamoto, Y , et al., "Reaction of 6H-1, 3-oxazin-6-one with benzyne giving isoquinoline derivatives", Chemical Abstracts, 118(7), Abstract No. 059563u, 831 (1993).
Yamashita, Y , et al., "Induction of Mammalian DNA Topoisomerase I and II Mediated DNA Cleavage by Saintopin, a New Antitumor Agent from Fungus", Biochemistry, 30(24), 5838-5845 (1991).
Yamashita, Y , et al., "Induction of Mammalian DNA Topoisomerase I Mediated DNA Cleavage by Antitumor Indolocarbazole Derivatives", Biochemistry, 31(48), 12069-12075 (1992).
Yu, Y , et al., "Comparative QSAR modeling of antitumor activity of ARC-111 analogues using stepwise MLR, PLS, and ANN techniques", Medicinal Chemistry Research 19(9), 1233-1244 (2009).
Zee-Cheng, K , et al., "Experimental Antileukemic Agents. Coralyne, Analogs, and Related Compounds", Journal of Medicinal Chemistry, 17(3), 347-351 (1974).
Zee-Cheng, K , et al., "Practical Preparation of Coralyne Chloride", Journal of Pharmaceutical Sciences, 61 (6), 969-971 (1972).
Zee-Cheng, R , et al., "Tetramethoxydibenzoquinolizinium Salts. Preparation and Antileukemic Activity of Some Positional and Structural Isomers of Coralyne", Journal of Medicinal Chemistry, 19(7), 882-886 (1976).
Zhu, S , et al., "6-Substituted 6H-dibenzo[c,h][2,6]naphthyridin-5-ones: Reversed lactam analogues of ARC-111 with potent topoisomerase I-targeting activity and cytotoxicity", Bioorganic & Medicinal Chemistry 14(9), 3131-3143 (2006).
Izmail'Skii, V , et al., "Absorption Spectra of Molecular Complexes of Derivatives of Benzacridine and Dibenzacridine", Chemical Abstracts, 54(8), Abstract, col. 7335b, 3 pages (1960).
Jacob, J , et al., "Monooxygenase Induction by Various Xenobiotics and its Influence on Rat Liver Microsomal Metabolism by Chrysene in Comparison to Benz[a]anthracene", Chemical Abstracts, 107, Abstract No. 34760, 2 pages (1987).
Janin, Y , et al., "Synthesis and Evaluation of New 6-Amino-Substituted Benzo[c]phenanthridine Derivatives", Journal of Medicinal Chemistry, 36(23), 3686-3692 (1993).
Jayaraman, M , et al., "Synthesis of New Dihydroindeno [1,2-c] isoquinoline and Indenoisoquinolinium Chloride Topoisomerase Inhibitors Having High in Vivo Anticancer Activity in the Hollow Fiber Animal Model", Journal of Medicinal Chemistry, 45(1), 242-249 (2002).
Kametani, T , et al., "Studies on the synthesis of heterocyclic compounds. DCXXVII. The formation of 2,3,9,10-tetramethoxybenz[c]acridine by treatment of 6,7-dimethoxy-1-(4,5-dimethoxy-2-nitrophenethyl)-2-methylisoquinoline with triethyl phosphite", Chemical and Pharmaceutical Bulletin, 23(9), 2025-2028 (1975).
Kametani, T , et al., "Synthesis of Heterocyclic Compounds. DCXXVII. Formation of 2,3,9,10-tetramethoxybenz[c]acridine by treatment of 6,7-dimethoxy-1-(4,5-dimethoxy-2-nitrophenethyl)-2-methylisoquinoline with Triethyl Phosphite", Chemical Abstracts, 84, Abstract No. 43798, 1 page (1976).
Kanmacher, I , et al., "Synthesis of Isoquino[1,2-b]quinazolines by Cycloaddition Reaction", Chemical Abstracts, 114, Abstract No. 207191, 4 pages (1990).
Kar, G , et al., "Regioselective Thermal Cyclization of 3-substituted Arylenaminoimine hydrochlorides. A convenient method for the synthesis of Functionalized Polycyclic Quinoline Derivatives", Chemical Abstracts, 123, Abstract No. 11828, 1 page (1995).
Kerrigan, J , et al., "5H-8,9-Dimethoxy-5-(2-N,N-dimethylaminoethyl)dibenzo[c, h][1,6]naphthyridin-6-ones and Related Compounds as TOP1-Targeting Agents: Influence of Structure on the Ternary Cleavable Complex Formation", Bioorganic and Medicinal Chemistry Letters, 13, 3395-3399 (2003).
Kessar, S , et al., "Azasteroids. Part VII. Synthesis of 7-hydroxy-2-methoxy-7,8,9,10-tetrahydrobenzo[i]phenanthridine", J. Chem. Soc., 259-261 (1971).
Kessar, S , et al., "New Routes to Condensed Polynuclear Compounds: Part X—Synthesis of Some Benzo[i]phenanthridine through Benzyne Cyclization", Indian Journal of Chemistry, 11, 624-627 (1973).
Kim, J , et al., "Influence of steric factors on topoisomerase I inhibition and cytotoxicity of bisbenzimidazoles related to Hoechst 33342", Abstract 7—Proceedings of the 3rd Annual Scientific Retreat of the Cancer Institute of New Jersey, Princeton Marriott Forrestal Village, 28 (1995).
Kim, J , et al., "Influence of steric factors on topoisomerase I inhibition and cytotoxicity of bisbenzimidazoles related to Hoechst 33342", Proceedings of the 86th Annual Meeting of the American Association for Cancer Research, 36, Abstract No. 2689, Toronto, Ontario, Canada, 451 (Mar. 1995).
Kim, J , et al., "Quantitative structure-activity relationships on 5-substituted terbenzimidazoles as topoisomerase I poisons and antitumor agents", Bioorganic & Medicinal Chemistry, 6(2), 4 pages [Abstract] (1998).
Kim, J , et al., "Steric factors associated with the topoisomerase I inhibition and cytotoxicity of substituted bisbenzimidazoles", Abstract 10—Proceedings of the American Association of Pharmaceutical Scientists Eastern Regional Meeting, 27 (1995).
Kim, J , et al., "Structure-activity Relationships of Benzimidazoles and Related Heterocycles as Topoisomerase I Poisons", Bioorganic & Med. Chem., 4, 621-630 (1996).
Kim, J , et al., "Substituted 2,5'-Bi-1H-benzimidazoles: Topoisomerase I Inhibition and Cytotoxicity", Journal of Medicinal Chemistry, 39(4), 992-998 (1996).
Kim, J , et al., "Terbenzimidazoles: influence of 2"-, 4-, and 5-subtituents on cytotoxicity and relative potency as topoisomerase I poisons", Journal of Medicinal Chemistry, 40(18), 2818-2824 (1997).
Kitamura, T , et al., "Isoquinoline derivatives from the Ritter-type reaction of vinyl cations", Chemical Abstracts, 102(1), Abstract No. 6157c, (1985).
Klopman, G , et al., "Testing by Artificial Intelligence: Computational Alternatives to the Determination of Mutagenicity", Chemical Abstracts, 118, Abstract No. 17489, 1 page (1993).
Knab, A , et al., "Mechanisms of Camptothecin Resistance in Yeast DNA Topoisomerase I Mutants", Journal of Biological Chemistry, 268(30), 22322-22330 (1993).
Kurtzberg, LS , et al., "Bone marrow and tumor cell colony-forming units and human tumor xenograft efficacy of noncamptothecin and camptothecin topoisomerase I inhibitors", Molecular Cancer Therapeutics 7, 3212-3222 (2008).
Lavoie, E , et al., "Structure-activity studies related to minor groove-binding ligands which inhibit mammalian DNA topoisomerase

(56) References Cited

OTHER PUBLICATIONS

I", Abstract 1—Proceedings of the 85th Annual Meeting of American Association for Cancer Research, San Francisco, CA, 2699 (Apr. 1994).
Lee, J, et al., "Coralyne binds tightly to both T A T- and C G C+-containing DNA triplexes", Biochemistry, 32(21), 5591-5597 (1993).
Li, T, et al., "Characterization of ARC-111 as a Novel Topoisomerase I-Targeting Anticancer Drug", Cancer Research 63, 8400-8407 (2003).
Liao, S, et al., "A Combined 2D- and 3D-QSAR Study on Analogues of ARC-111 with Antitumor Activity", ASAR Comb Sci 27(6), 740-749 (2008).
Liu, L, et al., "Cleavage of DNA by Mammalian DNA Topoisomerase II", Journal of Biological Chemistry, vol. 258, No. 24, 15365-15370 (1983).
Makhey, D, "Coralyne and Related Compounds as Mammalian Topoisomerase I and Topoisomerase II Poisons", Bioorganic & Medicinal Chemistry, 4(6), 781-791 (1996).
Makhey, D, et al., "Protoberberine Alkaloids and Related Compounds as Dual Inhibitors of Mammalian Topoisomerase I and II", Medicinal Chemistry Research, 5(1), 1-12 (1994).
Meegalla, S, et al., "Synthesis and Pharmacological Evaluation of Isoindolo[1,2-b]quinazolinone and Isoindolo[2,1-a]benzimidazole Derivatives Related to the Antitumor Agent Batracylin", J. Med. Chem., 37, 3434-3439 (1994).
Memetzidis, G, et al., "Structure-affinity relationships of berbines or 5,6,13,13a-tetrahydro-8H-dibenzo[a,g]quinolizines at alpha-adrenoceptors", European Journal of Medicinal Chemistry, 26, 605-611 (1991).
Messmer, F, et al., "Fagaronine, a New Tumor Inhibitor Isolated from Fagara zanthoxyloides Lam. (Rutaceae)", Journal of Pharmaceutical Sciences, 1858-1859 (1972).
Mohanty, N, et al., "New Therapeutic agents of the quinoline series. I. Fused quinolyl compounds", Chemical Abstracts, XP 002049521, 1792 (1968).
Mosmann, "Rapid Colorimetric Assay for Cellular Growth and Survival: Application to Proliferation and Cytotoxicity Assays", Journal of Immunological Methods, 65(1-2), 55-63 (1983).
Nelson, J, et al., "Proton and carbon-13 NMR spectra of fifteen substituted isoquinolines", Chemical Abstract, 115(5), Abstract No. 048721, 753 (1991).
Patent Cooperation Treaty, International Searching Authority, Search Report and Written Opinion for PCT/US2017/025779, 10 pages, dated Sep. 5, 2017.
Peters, D, et al., "Synthesis of Various 5-Substituted Uracils", Journal of Heterocyclic Chemistry, 27, 2165-2173 (1990).
Pilch, D, et al., "A terbenzimidazole that preferentially binds and conformationally alters structurally distinct DNA duplex domains:
a potential mechanism for topoisomerase I poisoning", Proc. Nat'l. Acad. Sci. USA, 94(25), 13565-13570 (1997).
Pilch, D, et al., "Biophysical Characterization of a Cytotoxic, Topoisomerase I Poison", Abstract 8—Proceedings of the 3rd Annual Scientific Retreat of the Cancer Institute of New Jersey, Princeton Marriott Forrestal Village, Princeton, NJ, 2 pages (Jun. 1, 1995).
Pilch, D, et al., "Characterizing the DNA binding modes of a topoisomerase I-poisoning terbenzimidazole: evidence for both intercalative and minor groove binding properties", Drug Design and Discovery, 13, 115-133 (1996).
Piper, J, et al., "Synthesis and Antifolate Activity of 5-Methyl-5,10-dideaza Analogues of Aminopterin and Folic Acid and an Alternative Synthesis of 5, 10-Dideazatetrahydrofolic Acid, a Potent Inhibitor of Glycinamide Ribonucleotide Formyltransferase", J. Med. Chem., 31, 2164-2169 (1988).
Porai-Koshits, B, et al., "Imidazole derivatives. IV. Synthesis of some polybenzimidazoles", J. Gen. Chem. USSR, 23, As related in Chemical Abstracts, 48(10) (1954), col. 12740, (1953), pp. 873-879 (1953).
Quast, U, et al., "Heterocyclic alpha-carbinolamines with the isoquinuclidines skeleton. 3. Benzoisoquinuclidines", Chemical Abstracts, 97 (21), Abstract No. 182180s, 806 (1982).
Ramesh, D, et al., "Studies on Polycyclic Azaarenes. 2. Synthesis of Trans-3,4-dihydroxy-3,-dihydrobenz[c]acridine and trans-8,9-dihydroxy-8,9-dihydrobenz[c]acridine", Chemical Abstracts, 108, Abstract No. 37626, 2 pages (1988).
Ray, J, et al., "A Facile and Convenient Method for the Synthesis of 8-methoxy-10,11-dihydronaphtho[1,2-b]quinolones", Chemical Abstracts, 92, Abstract No. 76254, 30-31 (1980).
Ruchelman, A, et al., "11H-Isoquino[4,3-c]cimmolin-12-ones: novel anticancer agents with potent topoisomerase I-targeting activity and cytotoxicity", Bioorganic & Medicinal Chemistry 12, 795-806 (2004).
Ruchelman, AL, et al., "5-(2-aminoethyl)dibenzo[c,h][1,6]naphthyridin-6-ones: variation of n-alkyl substituents modulates sensitivity to efflux transporters associated with multidrug resistance", J Med Chem 48 (3), 792-804 (2005).
Ruchelman, A, et al., "Diaza- and Triazachrysenes: Potent Topoisomerase-Targeting Agents with Exceptional Antitumor Activity against the Human Tumor Xenograft, MDS-MB-435", Bioorganic & Medicinal Chemistry Letters 12, 3333-3336 (2002).
Ruchelman, et al., "Dimethoxybenzol[i]phenanthridine-12-carboxylic acids derivatives and 6H-dibenzol[c,h][2,6]naphthyridin-5-ones with potent topoisomerase I-targeting activity and cytotoxicity", Bioorganic & Medicinal Chemistry Letters, 14, 5585-5589 (2004).
Safaryan, G, et al., "2-Benzopyrylium salts. 25, Reaction of 2-benzopyrylium salts with some nucleophiles", Chemical Abstracts, 96(17), Abstract No. 142656z, 739 (1982).

\* cited by examiner

TOPOISOMERASE POISONS

PRIORITY OF INVENTION

This application claims priority from U.S. Provisional Patent Application No. 62/318,139 filed Apr. 4, 2016, which is hereby incorporated by reference in its entirety.

BACKGROUND OF THE INVENTION

The non-camptothecin topoisomerase I-targeting agent of formula II (8,9-dimethoxy-2,3-methylenedioxy-5-[2-(N-methylamino)ethyl]-5H-dibenzo[c,h]1,6-naphthyridin-6-one), is known to be very potent as an antitumor agent against several human tumor types (International Patent Application Number PCT/US02/36901, filed Nov. 14, 2002 and published on May 22, 2003 as WO 03/041660).

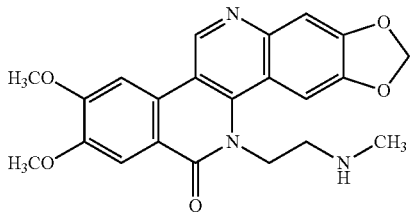

However, this compound can form reactive intermediates when subjected to various purification processes. The formation of such reactive intermediates is illustrated in Scheme 1. The formation of these imine reactive intermediates from this intramolecular cyclodehydration is variable and can result in the formation of by-products as these electrophiles may interact with an available nucleophile. Although in aqueous systems, this does not represent a major problem, there are concerns regarding purification, storage, and the characterization of this compound. Thus, prodrugs of the compound of formula II which reduce the formation of these reactive intermediates would be advantageous.

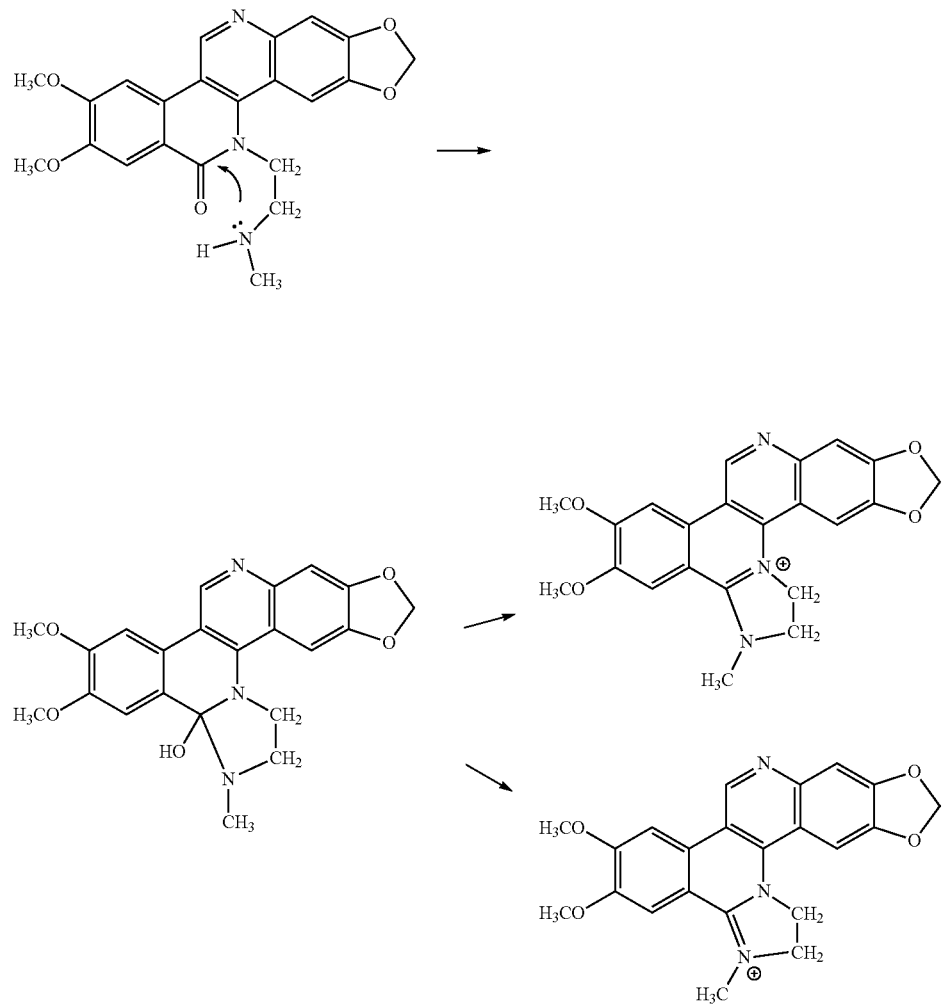

Scheme 1

The compound of formula II may also not have optimal exposure at certain organ sites such as organ sites that inherently have a lower or higher pH than the typical physiologic pH of 7.4. In addition, optimal exposure may not be achieved within the central nervous system (CNS) for treating diseases of the CNS such as CNS cancers. Prodrugs of the compound of formula II with enhanced physicochemical properties (e.g., lipophilicity) may thus be advantageous in the delivery of the active agent to sites in the CNS. In addition, the compound of formula II may not have optimal properties (e.g. acidic/basic properties or tumor affinity) for the selective delivery to the (or accumulation at the) desired target site of action (e.g., cell, tissue or organ) effected by a disease such as cancer.

Accordingly, there is currently a need for prodrugs of the compound of formula II with beneficial properties. Such beneficial properties may include one or more of the following such as improved chemical stability, improved methods of processing the compound (e.g., purification during manufacture), improved methods of characterizing the compound, improved cell, tissue or organ targeting and/or improved activation at the site of action.

SUMMARY OF THE INVENTION

Applicant has discovered prodrugs of the compound of formula II that may have beneficial properties.

Accordingly, one embodiment provides a compound of formula I:

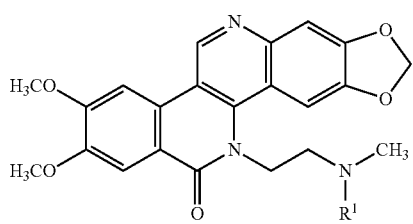

wherein $R^1$ is —C(=O)$R^a$, —C(=O)O$R^b$, a self-immolative moiety, or a linker substituted with one or more targeting moieties;

$R^a$ is (C$_1$-C$_6$) alkyl, 5-6-membered monocyclic heterocycle, phenyl, or 5-6-membered monocyclic heteroaryl wherein any (C$_1$-C$_6$) alkyl of $R^a$ is optionally substituted with one or more halogen, hydroxy, —O(C$_1$-C$_6$)alkyl, COO$R^c$, or N$R^d R^e$ and any 5-6-membered monocyclic heterocycle, phenyl, or 5-6-membered monocyclic heteroaryl of $R^a$ is optionally substituted with one or more halogen, $R^f$, COO$R^c$, or N$R^d R^e$;

$R^b$ is (C$_1$-C$_6$) alkyl, 5-6-membered monocyclic heterocycle, phenyl, or 5-6-membered monocyclic heteroaryl wherein any (C$_1$-C$_6$) alkyl of $R^b$ is optionally substituted with one or more halogen, hydroxy, —O(C$_1$-C$_6$)alkyl, COO$R^c$, or N$R^d R^e$ and any 5-6-membered monocyclic heterocycle, phenyl, or 5-6-membered monocyclic heteroaryl of $R^b$ is optionally substituted with one or more halogen, hydroxy, $R^f$, COO$R^c$, or N$R^d R^e$;

each $R^c$ is independently hydrogen or (C$_1$-C$_4$)alkyl;

each $R^d$ and $R^e$ is independently hydrogen or (C$_1$-C$_3$) alkyl, or $R^d$ and $R^e$ together with the nitrogen to which they are attached form a 3-7 membered monocyclic heterocycle optionally substituted with one or more (C$_1$-C$_3$)alkyl; and each $R^f$ is independently (C$_1$-C$_6$) alkyl or —O(C$_1$-C$_6$) alkyl wherein any (C$_1$-C$_6$)alkyl or —O(C$_1$-C$_6$) alkyl of $R^f$ is optionally substituted with one or more halogen, hydroxy, COO$R^c$, or N$R^d R^e$;

or a salt thereof.

One embodiment provides a pharmaceutical composition comprising a compound of formula I or a pharmaceutically acceptable salt thereof as described herein and a pharmaceutically acceptable diluent or carrier.

One embodiment provides a method for modulating topoisomerase activity in a mammal (e.g. a human) comprising administering to the mammal, an effective amount of a compound a compound of formula I or a pharmaceutically acceptable salt thereof as described herein, to provide a topoisomerase modulating effect.

One embodiment provides a method of inhibiting cancer cell growth, comprising administering to a mammal (e.g. a human) in need thereof, an effective amount of a compound of formula I or a pharmaceutically acceptable salt thereof as described herein, to inhibit the growth of said cancer cells.

One embodiment provides a method of treating cancer, comprising administering to a mammal (e.g. a human) in need thereof a compound of formula I or a pharmaceutically acceptable salt thereof as described herein.

One embodiment provides a compound of formula I or a pharmaceutically acceptable salt thereof as described herein for use in medical therapy (e.g. for use in treating cancer including solid tumors).

One embodiment provides the use of a compound of formula I or a pharmaceutically acceptable salt thereof as described herein, for the manufacture of a medicament useful for the treatment of cancer (e.g. solid tumors) in a mammal (e.g. a human).

One embodiment provides the use of a compound of formula I or a pharmaceutically acceptable salt thereof as described herein, for the manufacture of a medicament useful for the treatment of a fungal infection in a mammal (e.g. a human).

One embodiment provides a compound of formula I or a pharmaceutically acceptable salt thereof as described herein, for use in the prophylactic or therapeutic treatment of cancer (e.g. solid tumors) or a fungal infection.

One embodiment provides processes and novel intermediates disclosed herein which are useful for preparing compounds of formula I. Some of the compounds of the invention are useful to prepare other compounds of the invention.

DETAILED DESCRIPTION

The following definitions are used, unless otherwise described.

The compounds of formula I described herein are prodrugs of the compound of formula II and specifically are derivatives at the nitrogen atom of the pendant "methylamine" moiety of the compound formula II. Thus, the compounds of formula I comprise a residue of the compound of formula II which residue results from the removal of the hydrogen atom from the pendent methylamine moiety of the compound of formula II thereby creating the open valency required to produce the compounds of formula I. The following structure shows the residue of the compound of formula II wherein the asterisk illustrates that site at which the compound is derivatized to provide the prodrug (i.e., the compounds of formula I).

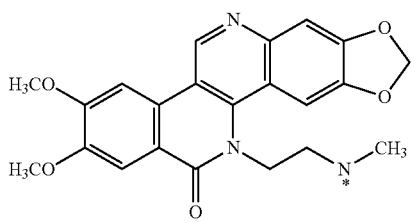 [SMILES: CNCCn1c(=O)c2cc(OC)c(OC)cc2c2cnc3cc4c(cc3c21)OCO4]

As a prodrug of the compound of formula II, the compound of formula I ultimately provides the compound of formula II (e.g., at some point after administration).

Alkyl, for example such as "$(C_1-C_{10})$alkyl" and "$(C_1-C_6)$ alkyl" denotes both straight and branched carbon chains with one or more, for example, 1, 2, 3, 4, 5, 6, 7, 8 9, 10 (or 1-6), carbon atoms, but reference to an individual radical such as "propyl" embraces only the straight chain radical, a branched chain isomer such as "isopropyl" being specifically referred to.

Aryl denotes a phenyl radical or an ortho-fused bicyclic carbocyclic radical having about nine to ten ring atoms in which at least one ring is aromatic. Examples of aryl include phenyl, indenyl, and naphthyl.

Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl include furyl, imidazolyl, triazolyl, triazinyl, oxazoyl, isoxazolyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) and quinolyl (or its N-oxide).

The term "heterocycle" or "heterocyclic" refers to a monovalent saturated or partially unsaturated cyclic non-aromatic group which contains at least one heteroatom, preferably 1 to 4 heteroatoms, selected from nitrogen ($NR_x$, wherein $R_x$ is hydrogen, alkyl, or a direct bond at the point of attachment of the heterocycle group), sulfur, phosphorus, and oxygen within at least one cyclic ring and which may be monocyclic or multi-cyclic. Such heterocycle groups preferably contain from 3 to 10 atoms. The point of attachment of the heterocycle group may be a carbon or nitrogen atom. This term also includes heterocycle groups fused to an aryl or heteroaryl group, provided the point of attachment is on a non-aromatic heteroatom-containing ring. Representative heterocycle groups include, by way of example, pyrrolidinyl, piperidinyl, piperazinyl, imidazolidinyl, morpholinyl, indolin-3-yl, 2-imidazolinyl, 1,2,3,4-tetrahydroisoquinolin-2-yl, quinuclidinyl and the like.

Alkoxy such as for example "$(C_1-C_6)$alkoxy" refers to groups of the formula $(C_1-C_6)$alkyl-O—, where $(C_1-C_6)$ alkyl is as defined herein. Alkoxy groups include, by way of example, methoxy, ethoxy, propoxy, iso-propoxy, n-butoxy, tert-butoxy, sec-butoxy, n-pentoxy, n-hexoxy, 1,2-dimethylbutoxy, and like groups.

Alkanoyloxy such as for example "$(C_1-C_6)$alkanoyloxy" includes, by way of example, formyloxy, acetoxy, propanoyloxy, iso-propanoyloxy, n-butanoyloxy, tert-butanoyloxy, sec-butanoyloxy, n-pentanoyloxy, n-hexanoyloxy, 1,2-dimethylbutanoyloxy, and like groups.

"Heteroaryloxy" refers to a group of the formula heteroaryl-O—, where heteroaryl is as defined herein. Examples of heteroaryloxy groups include 3-pyridinyloxy, 3-furyloxy, and 4-imidazoyloxy.

Alkanoyl such as for example "$(C_1-C_6)$alkanoyl" includes by way of example, formyl, acetyl, propanoyl, butanoyl, pentanoyl, hexanoyl, and like groups.

Alkoxycarbonyl such as for example "$(C_1-C_6)$alkoxycarbonyl" refers to group of the formula $(C_1-C_6)$alkoxy-C(=O)— where $(C_1-C_6)$alkoxy is as defined herein and includes by way of example, methoxycarbonyl, ethoxycarbonyl, propoxycarbonyl, isopropoxycarbonyl, butoxycarbonyl, pentoxycarbonyl, hexyloxycarbonyl and like groups.

As used herein the term "peptide" is a sequence of 2 to 100 amino acids.

As used herein the term "polyamine" includes but is not limited to bovine serum albumin, alginate that has been treated with ethylenediamine, lysozyme (e.g., such as lysozyme that contains free amino groups (such as 7 free amino groups) polyamine based polymers such as polylysine and poly-alpha amino acids and diaminoalkyl (e.g., $(C_1-C_{12})$ alkyl substituted with two or more amine (e.g., $NH_2$, $NH(C_1-C_6)$alkyl) groups; $NH_2—(C_1-C_{12})$alkyl-$NH_2$). In one embodiment the nitrogen atoms of two amino groups of the polyamine are each connected to the remainder of the compound of formula I (via the removal of a hydrogen atom from each of the amines to create the open valency; e.g., a residue of a polyamine). The following listed include "polyamines" that are useful as described herein; these documents are each hereby incorporated by reference in their entirety ((1) W. C. Shen, H. J. P. Ryser, cis-Aconityl spacer between daunomycin and macromolecular carriers: a model of pH-sensitive linkage releasing drug from lysosomotropic conjugate, Biochem. Biophys. Res. Commun. 102 (1981) 1048-1054; (2) Haas, M., Moolenaar, F., Elsinga, A., Van Der Wouden, E. A., De Jong, P. E., Meijer, D. K. F., De Zeeuw. D., Targeting of Doxorubicin to the Urinary Bladder of the Rat Shows Increased Cytotoxicity in the Bladder Urine Combined With An Absence of Renal Toxicity, Journal of Drug Targeting, 10(1) (2002) 81-89; (3) Pinhassi, R. I., Assaraf, Y. G., Farber, S., Stark, M., Ickowicz, D., Drori, S., Domb, A. J., Livney, Y. D., Arabinogalactan—Folic Acid—Drug Conjugate for Targeted Delivery and Target-Activated Release of Anticancer Drugs to Folate Receptor-Overexpressing Cells, Biomacromolecules, 11 (2010) 294-303; (4) Du, C., Deng, D., Shan, L., Wan, S., Cao, J., Tian, J., Achilefu, S., Gu, Y., A pH-sensitive doxorubicin prodrug based on folate-conjugated BSA for tumor-targeted drug delivery, Biomaterials 34 (2013) 3087-3097; (5) Ulbrich, K., Etrych, T., Chytil, P., Jelinkova, M., Rihova, B., HPMA copolymers with pH-controlled release of doxorubicin; In vitro cytotoxicity and in vivo antitumor activity, Journal of Controlled Release 87 (2003) 33-47).

Specific and preferred values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl and $(C_1-C_6)$alkoxy can be methoxy, ethoxy, propoxy, isopropoxy, butoxy, iso-butoxy, sec-butoxy, pentoxy, 3-pentoxy, or hexoxy.

In one embodiment $R^1$ is —C(=O)$R^a$ or —C(=O)O$R^b$.
In one embodiment $R^1$ is —C(=O)$R^a$.
In one embodiment $R^1$ is —C(=O)O$R^b$.

In one embodiment R$^a$ is (C$_1$-C$_6$) alkyl or a piperidinyl wherein the piperidinyl is optionally substituted with one or more halogen, (C$_1$-C$_6$) alkyl or —O(C$_1$-C$_6$) alkyl.

In one embodiment R$^a$ is methyl or piperidinyl.
In one embodiment R$^b$ is (C$_1$-C$_6$) alkyl.
In one embodiment R$^b$ is methyl or t-butyl.
In one embodiment the compound of formula I is:

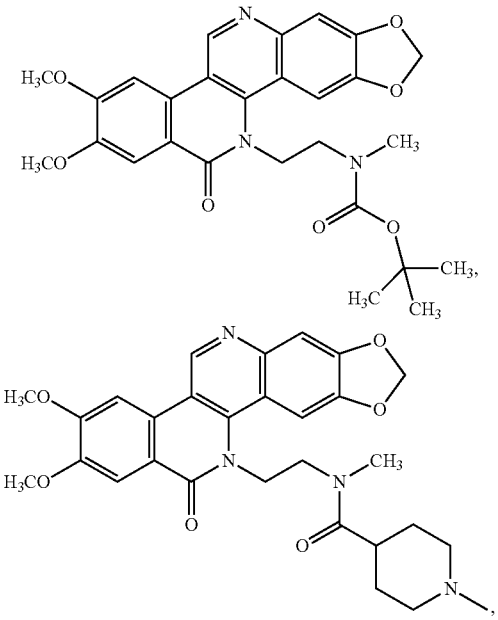

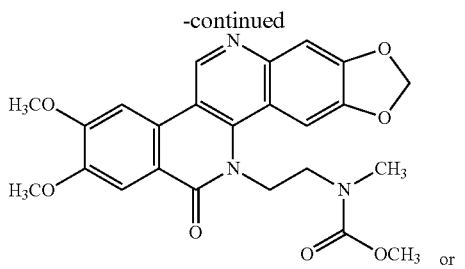

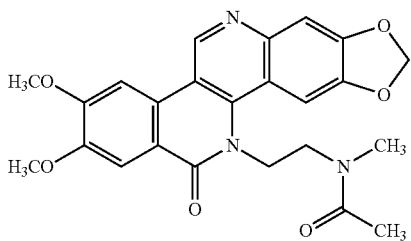

or a pharmaceutically acceptable salt thereof.

In one embodiment R$^1$ is a self-immolative moiety.
In one embodiment R$^1$ is a self-immolative moiety that is:

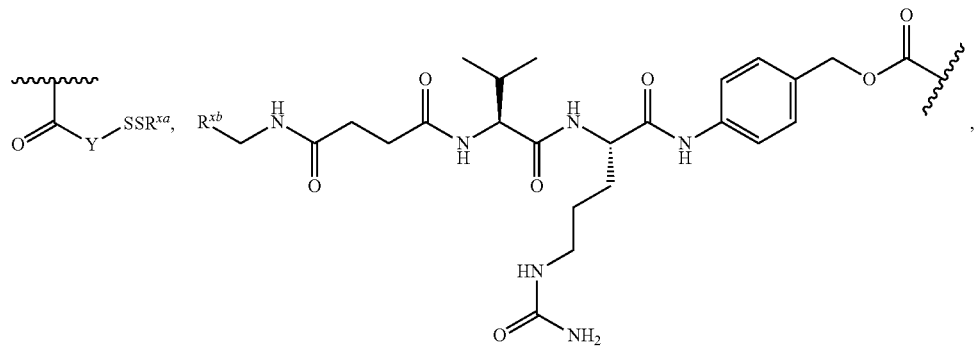

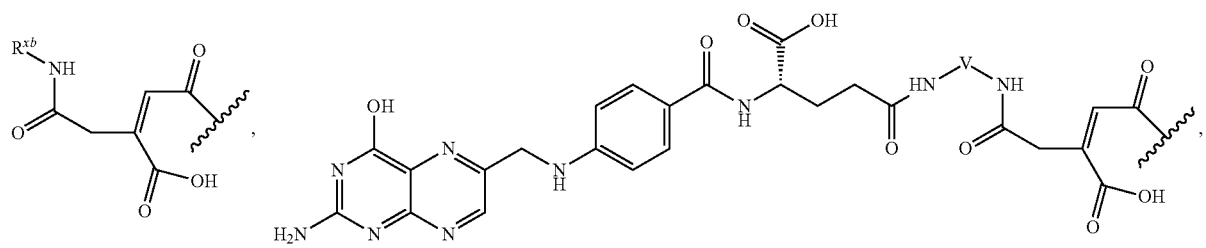

-continued

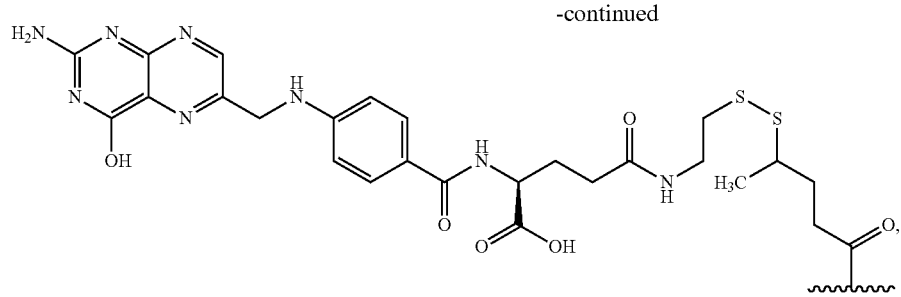

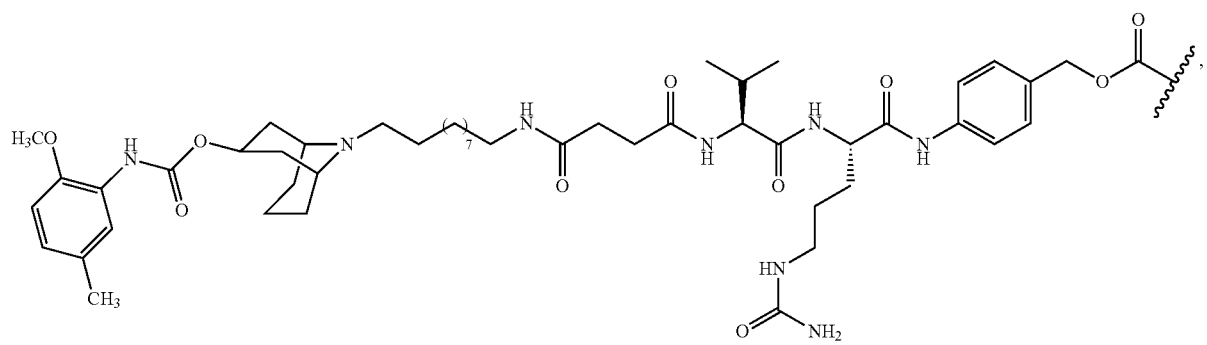

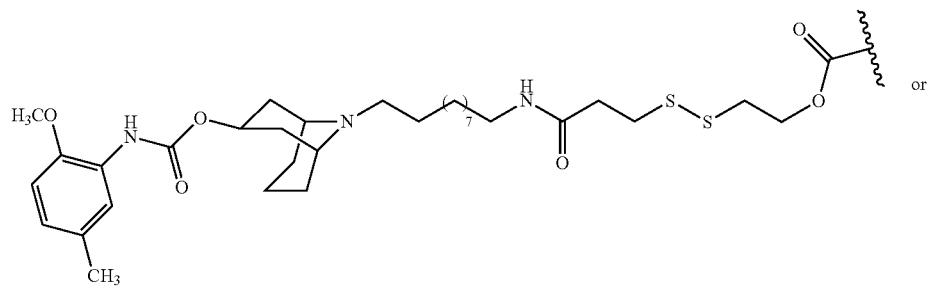

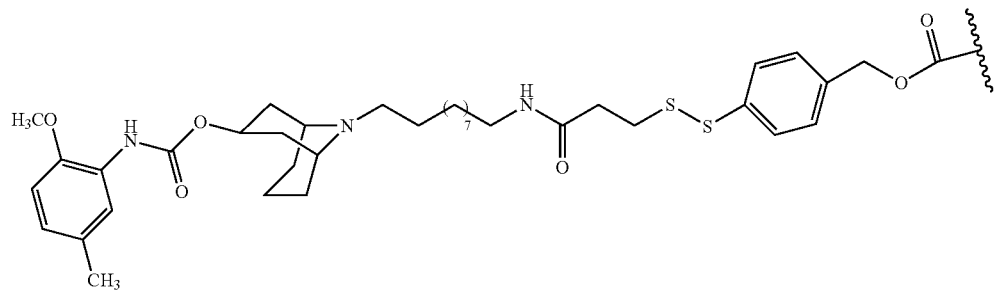

wherein Y is $(C_2-C_{10})$alkyl; V together with two nitrogen atoms as shown attached to V is a polyamine; $R^{xa}$ is $(C_1-C_{10})$alkyl, phenyl or 5-6-membered monocyclic heteroaryl wherein any phenyl or 5-6-membered monocyclic heteroaryl of $R^{xa}$ is optionally substituted with one or more halogen, $(C_1-C_4)$alkyl or $(C_1-C_4)$alkyl; and $R^{xb}$ is $(C_1-C_{10})$alkyl, —$O(C_1-C_{10})$alkyl, phenyl, or a 5-6-membered monocyclic heteroaryl wherein any phenyl or 5-6-membered monocyclic heteroaryl is optionally substituted with one or more halogen, $(C_1-C_4)$alkyl, or —$O(C_1-C_4)$alkyl.

In one embodiment the compound of formula I is:
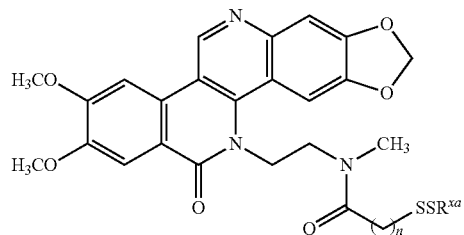
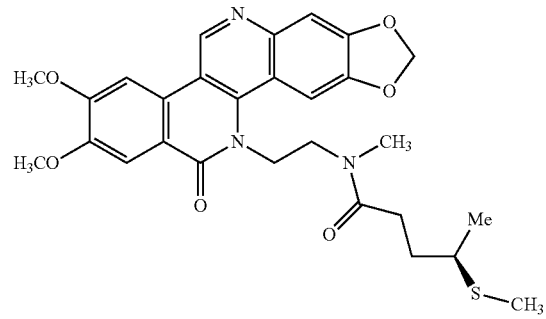
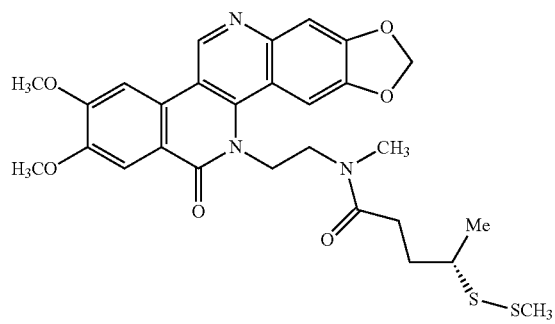
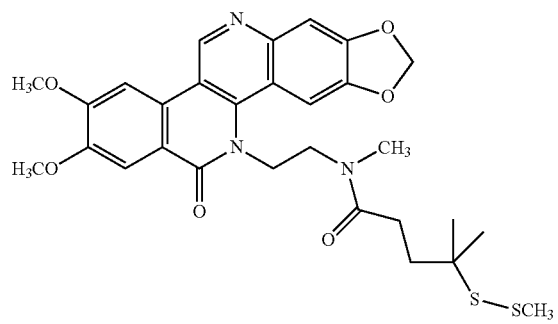
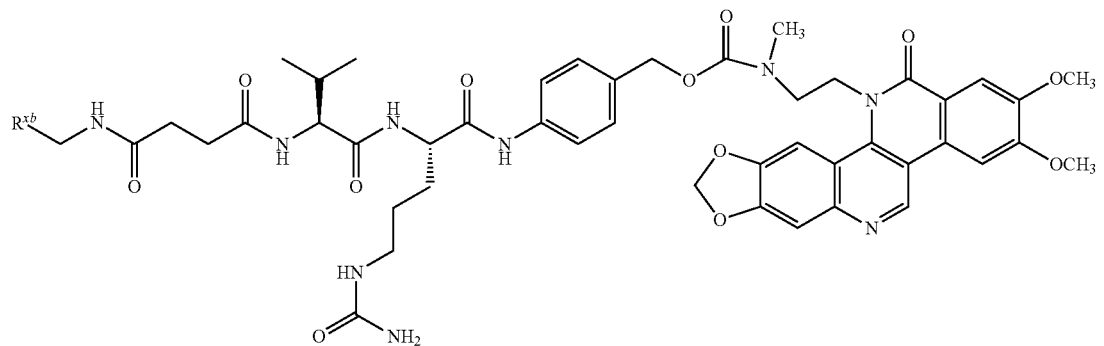
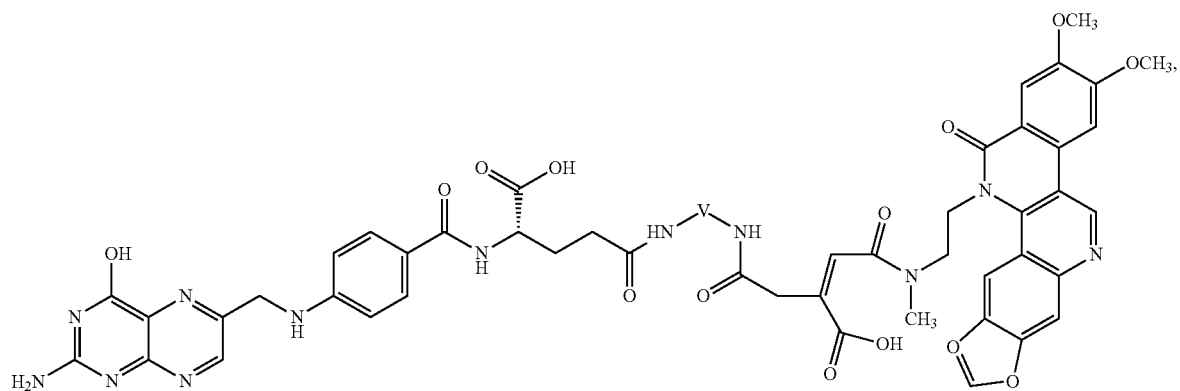

-continued

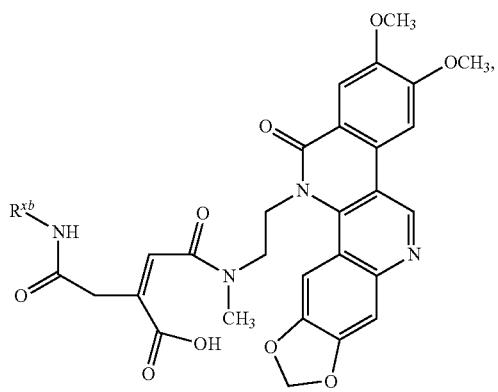

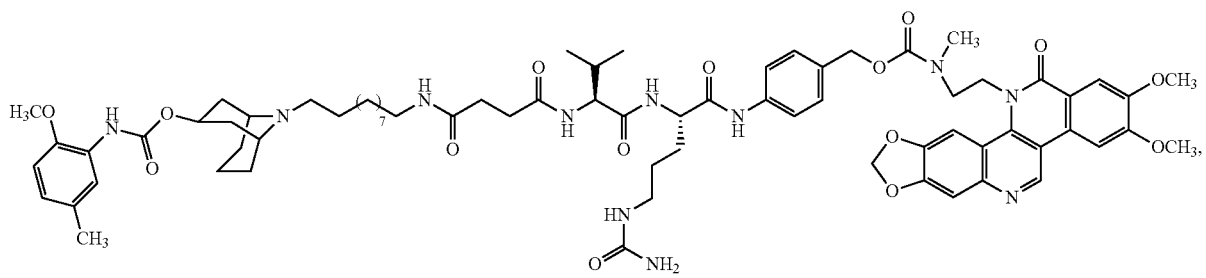

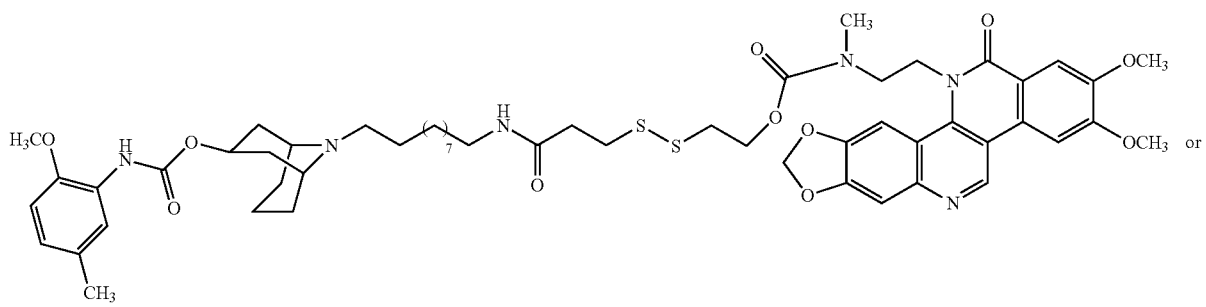

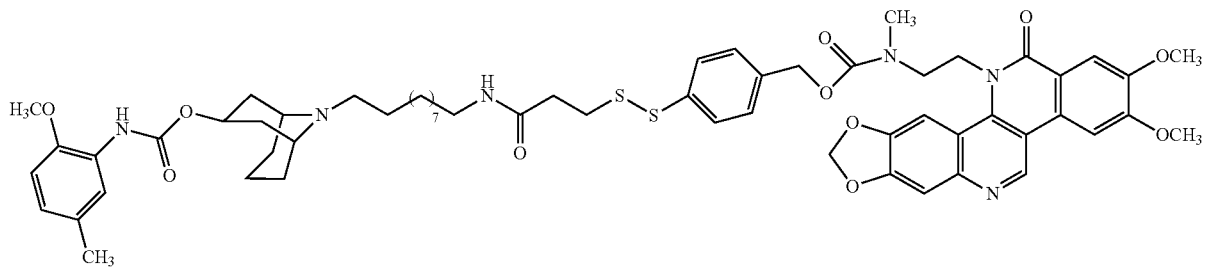

wherein n is 1, 2 or 3; $R^{xa}$ is $(C_1-C_{10})$alkyl, phenyl or 5-6-membered monocyclic heteroaryl wherein any phenyl or 5-6-membered monocyclic heteroaryl of $R^{xa}$ is optionally substituted with one or more halogen, $(C_1-C_4)$alkyl or $(C_1-C_4)$alkyl; and $R^{xb}$ is $(C_1-C_{10})$alkyl, —O$(C_1-C_{10})$alkyl, phenyl, or a 5-6-membered monocyclic heteroaryl wherein any phenyl or 5-6-membered monocyclic heteroaryl is optionally substituted with one or more halogen, $(C_1-C_4)$alkyl, or —O$(C_1-C_4)$alkyl; and V together with two nitrogen atoms as shown attached to V is a polyamine; or a pharmaceutically acceptable salt thereof.

In one embodiment $R^1$ is a self-immolative moiety that is:

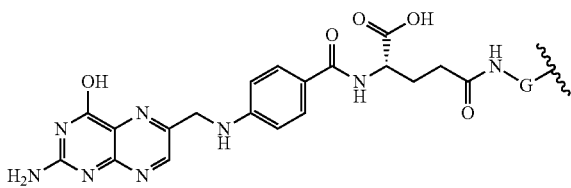

wherein G is a branched or unbranched, saturated or unsaturated, hydrocarbon chain, having from 2 to 25 carbon atoms, wherein one or more (e.g. 1, 2, 3, or 4) of the carbon atoms is optionally replaced by (—O—), (—NH—) or (—S—)and wherein the chain is optionally substituted on carbon with one or more (e.g. 1, 2, 3, or 4) substituents selected from ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, cyano, nitro, halo, hydroxy, oxo (=O), carboxy, aryl, aryloxy, heteroaryl, and heteroaryloxy.

In one embodiment $R^1$ is a linker substituted with one or more targeting moieties.

In one embodiment the linker has a formula of:

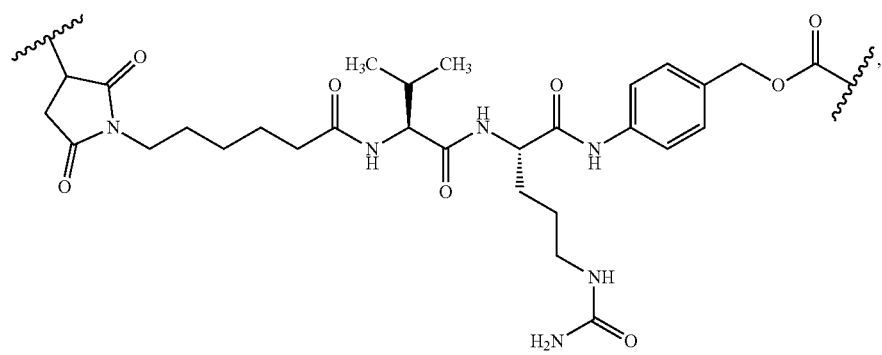

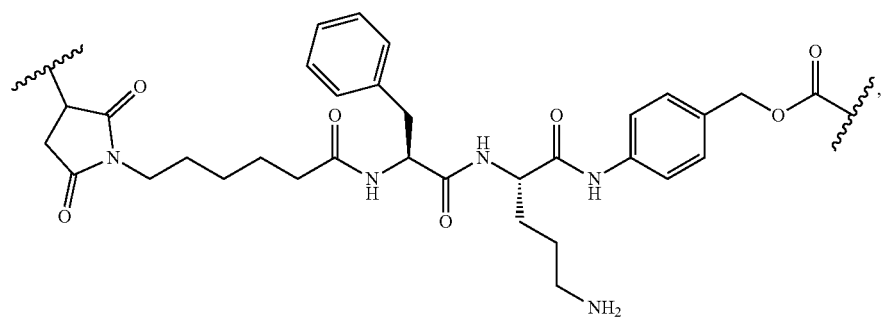

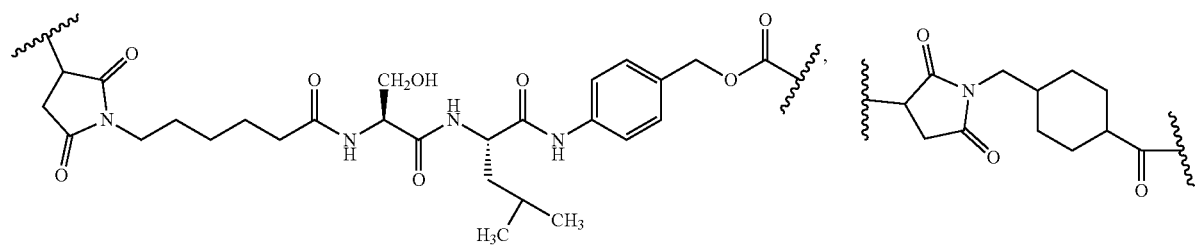

wherein the wavy line at the left depicts the point of attachment to the targeting moiety and wherein the wavy line at the right is the point of attachment to the remainder of the compound of formula I.

In one embodiment the linker has a formula of:

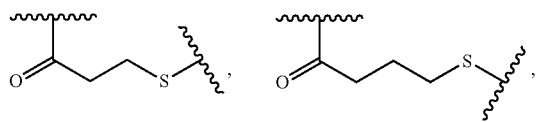

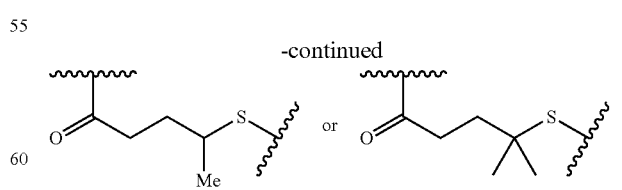

wherein the wavy line at the right depicts the point of attachment to the targeting moiety and wherein the wavy line at the left is the point of attachment to the remainder of the compound of formula I.

In one embodiment the compound of formula I is:
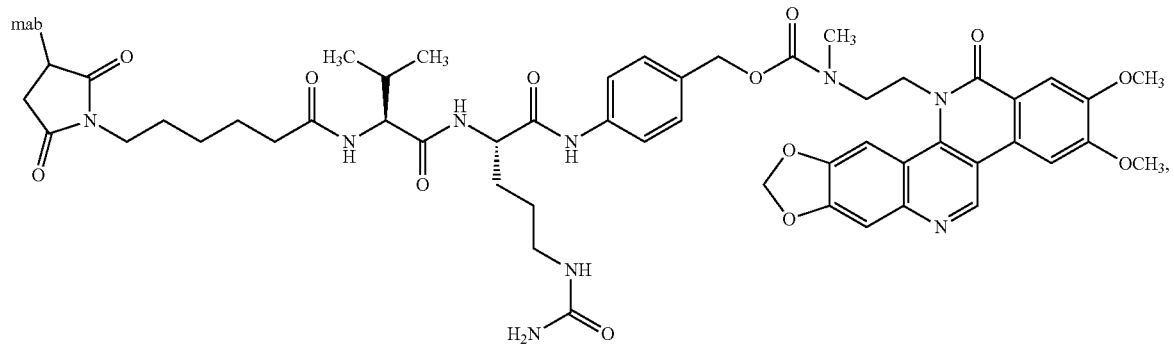
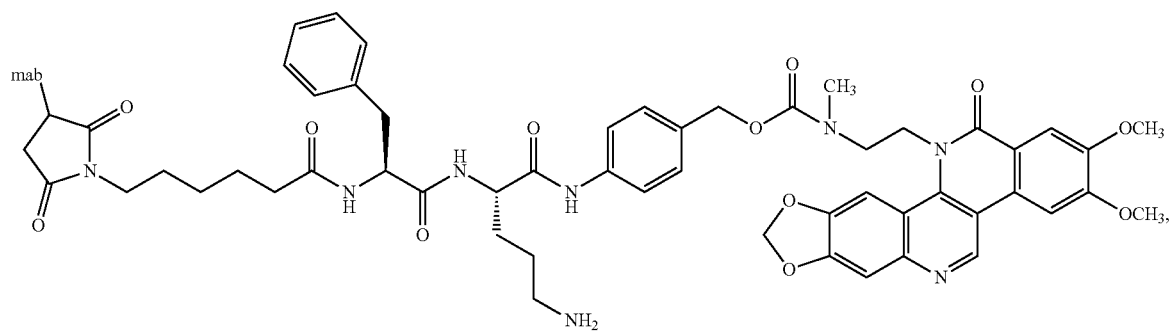
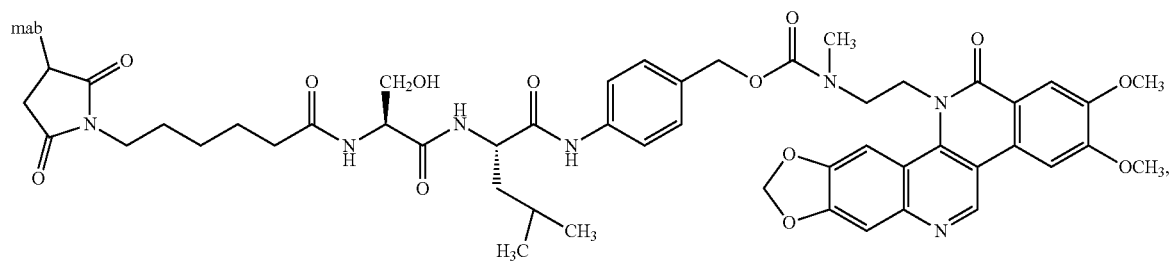
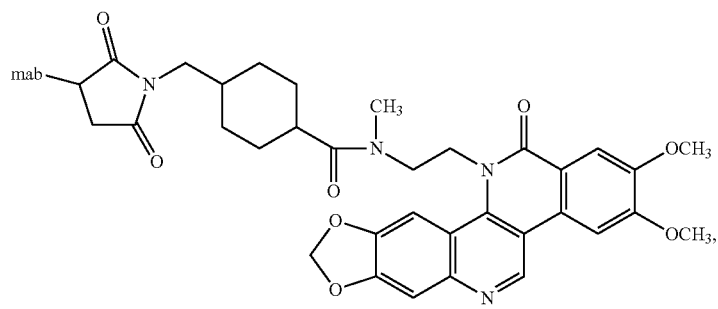
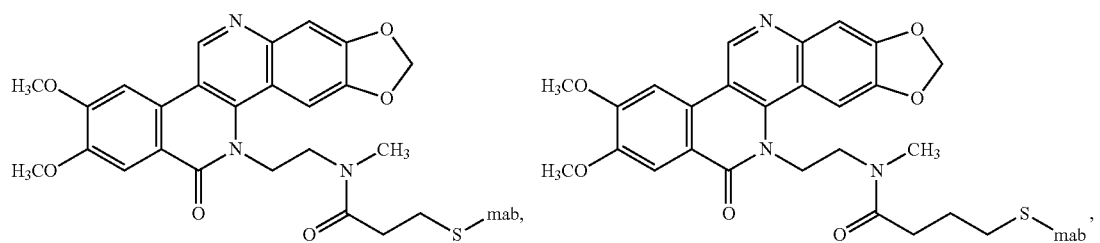

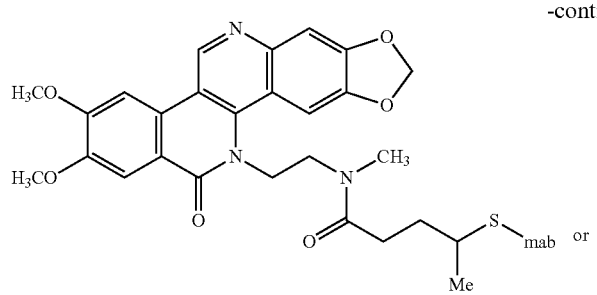

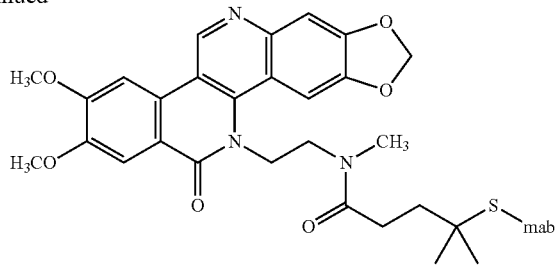

or a pharmaceutically acceptable salt thereof.

In one embodiment the mab is a monoclonal antibody to CD30, CD33, CD70, Her2 or CEA.

Self-Immolative Moiety

As used herein the term "self-immolative moiety" is a moiety that is released from a compound of formula I when administered to a biological system to generate the drug substance, i.e. active ingredient (the compound of formula II), as a result of spontaneous chemical reaction(s), enzyme catalyzed chemical reaction(s), photolysis, and/or metabolic chemical reaction(s) or by some other process to provide a compound of formula II. Several self-immolative moieties and methods for their synthesis are described in Tranoy-Opalinsky et al., Anti-Cancer Agents in Medicinal Chemistry, 2008, 8, 618-637, and in references therein.

In one embodiment the self-immolative moiety is:

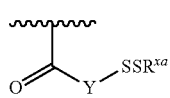

wherein Y is $(C_2-C_{10})$alkyl; and $R^{xa}$ is $(C_1-C_{10})$alkyl, phenyl or 5-6-membered monocyclic heteroaryl wherein any phenyl or 5-6-membered monocyclic heteroaryl of $R^{xa}$ is optionally substituted with one or more halogen, $(C_1-C_4)$alkyl or $(C_1-C_4)$alkyl In one embodiment the self-immolative moiety is:

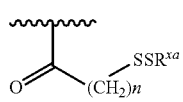

wherein n is 1, 2 or 3; and $R^{xa}$ is $(C_1-C_{10})$alkyl, phenyl or 5-6-membered monocyclic heteroaryl wherein any phenyl or 5-6-membered monocyclic heteroaryl of $R^{xa}$ is optionally substituted with one or more halogen, $(C_1-C_4)$alkyl or $(C_1-C_4)$alkyl.

In one embodiment the self-immolative moiety is:

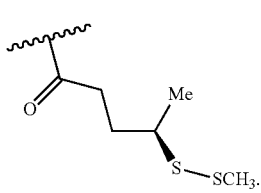 [SMILES: *C(=O)CC[C@@H](C)SSC]

In one embodiment the self-immolative moiety is:

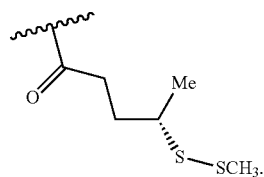

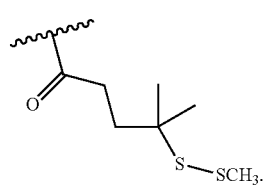

In one embodiment the self-immolative moiety is:

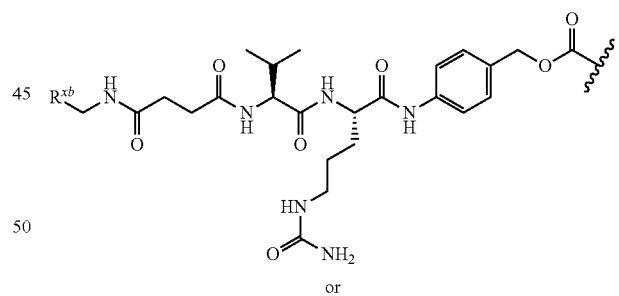

or

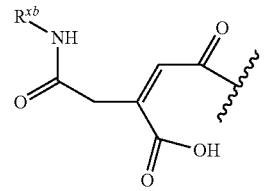

wherein $R^{xb}$ is $(C_1-C_{10})$alkyl, —O$(C_1-C_{10})$alkyl, phenyl, or a 5-6-membered monocyclic heteroaryl wherein any phenyl or 5-6-membered monocyclic heteroaryl is optionally substituted with one or more halogen, $(C_1-C_4)$alkyl, or —O$(C_1-C_4)$alkyl.

In one embodiment the self-immolative moiety is:
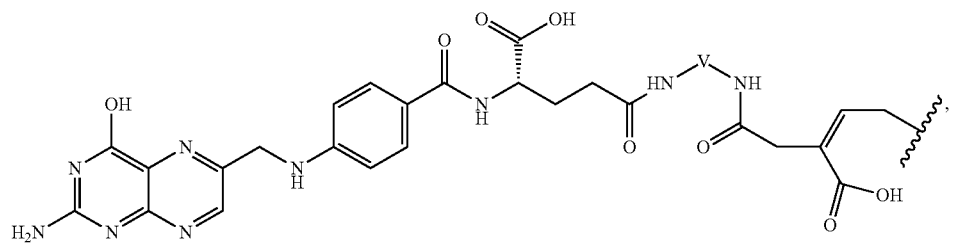
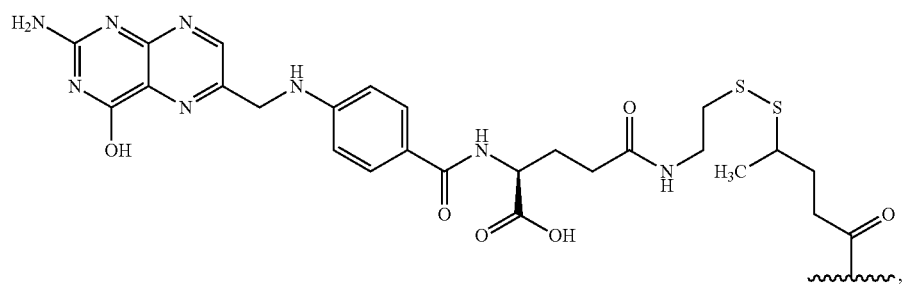
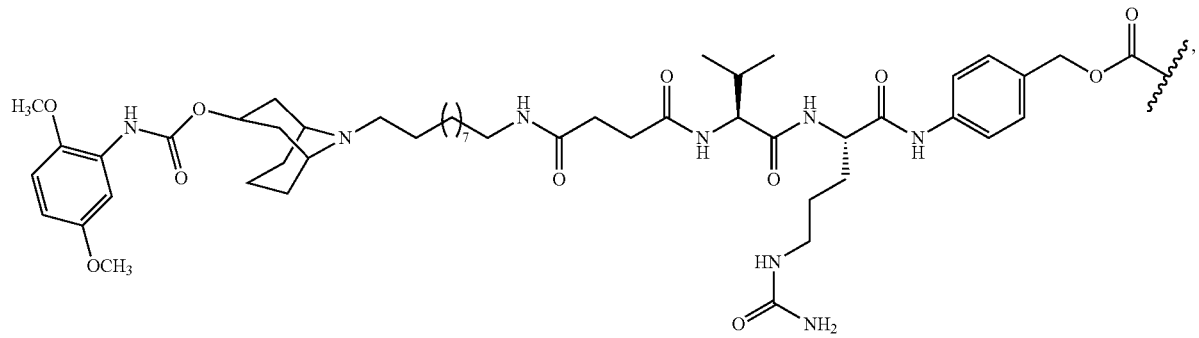
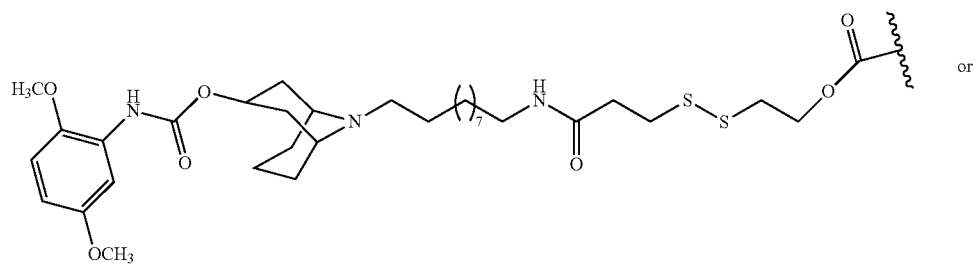 or
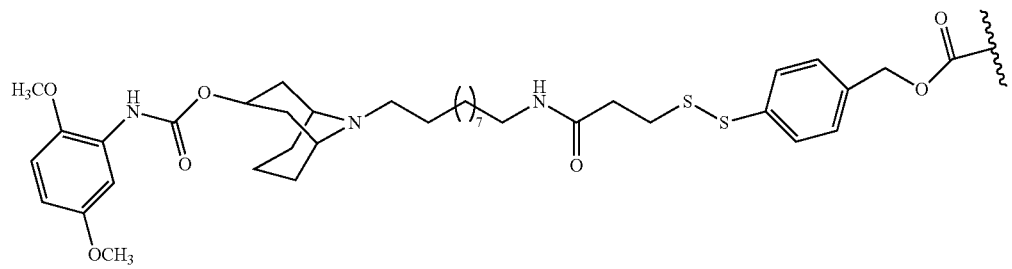

wherein V together with two nitrogen atoms as shown attached to V is a polyamine. In one embodiment the polyamine comprises alginate derivatives, bovine serum albumin, polylysine, lysozyme, or diaminoalkyl.

In another embodiment the self-immolative moiety is:

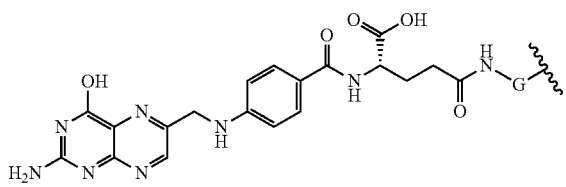

wherein G is a branched or unbranched, saturated or unsaturated, hydrocarbon chain, having from 2 to 25 carbon atoms, wherein one or more (e.g. 1, 2, 3, or 4) of the carbon atoms is optionally replaced by (—O—), (—NH—) or (—S—) and wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, cyano, nitro, halo, hydroxy, oxo (=O), carboxy, aryl, aryloxy, heteroaryl, and heteroaryloxy.

In one embodiment G is:

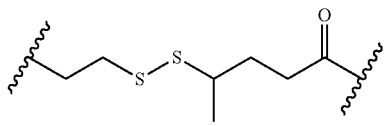 [SMILES: *CCSSC(C)CCC(*)=O]

In another embodiment the self-immolative moiety is:

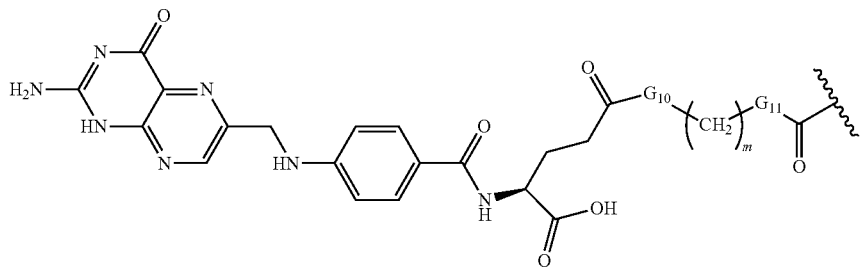

wherein $G_{10}$ and $G_{11}$ are each independently NH and O and m is 2 or 3.

Antibody-Drug Conjugates

Antibody-drugs conjugates (ADCs) have been developed for several monoclonal antibodies (mab) that have proven selective for various human cancers. This methodology has proved to be an effective means for improving the targeting of cancer chemotherapeutic to neoplastic cells while reducing side effects. More than twenty-different monoclonal antibodies have been employed in the formation of ADCs. These monocolonal antibodies have been linked to various cytotoxic agents with the objective of improving therapeutic efficacy, while reducing systemic toxicity. Monoclonal antibodies to CD30, CD33, CD70, Her2 and CEA attached to one or more cytotoxic agents have been among the more extensively studied. The number of chemotypes of cytotoxic agents relative to the number of monoclonal antibodies that have been used to form these ADCs is less than half. Maytansinoid, taxoid, doxorubicin, auristatin, calcicheasmicin, geldamycin, streptonigrin, and camptothecin derivatives are among the more commonly selected cytotoxic agents. The number of molecules of cytotoxic agent attached to each monoclonal antibody can vary depending upon the conditions under which the linkage to the cytotoxic agent if formed. There may be as one molecule of cytotoxic agent attached per monoclonal antibody to as high as 7 or more.

Potency and metabolic stability are factors that can influence the selection of cytotoxic agent used to form the ADC. Potency is a factor as there are limits to the amount of drug that can be loaded onto a monoclonal antibody. Metabolic stability is a factor as inactivation of the cytotoxic agent by plasma enzymes would limit the amount of effective agent that would be delivered to the cancerous cell. In one embodiment the invention provides a compound of the invention which is a potent cytotoxic agent with sufficient metabolic stability and accessible functionality (e.g. phenol) for forming conjugates (via a linker) to monoclonal antibodies.

Linker

As used herein the term "linker" includes groups that are covalently bonded to a targeting moiety and the reminder of the compound of formula I (i.e., the residue of the compound of formula I). The nature of the linker is not critical provided it does not interfere with the ability of compound to function as a prodrug.

In one embodiment the linker has a molecular weight of from about 20 daltons to about 100 daltons.

In one embodiment linker has a molecular weight of from about 20 daltons to about 400 daltons.

In another embodiment the linker has a length of about 5 angstroms to about 60 angstroms.

In another embodiment the linker separates the targeting moiety from the remainder of the compound of formula I by about 5 angstroms to about 40 angstroms, inclusive, in length.

In another embodiment the linker comprises about 5-200 atoms wherein the atoms include carbon, nitrogen, oxygen, sulfur, and hydrogen.

In another embodiment the linker comprises about 5-100 atoms wherein the atoms include carbon, nitrogen, oxygen, sulfur, and hydrogen.

In another embodiment the linker comprises about 7-100 atoms wherein the atoms include carbon, nitrogen, oxygen, sulfur, and hydrogen.

In another embodiment the linker comprises about 7-75 atoms wherein the atoms include carbon, nitrogen, oxygen, sulfur, and hydrogen.

In another embodiment the linker comprises about 7-75 atoms wherein the atoms include carbon, nitrogen, oxygen, and hydrogen.

In another embodiment the linker is a branched or unbranched, saturated or unsaturated, hydrocarbon chain, having from 2 to 60 carbon atoms, wherein one or more (e.g. 1, 2, 3, or 4) of the carbon atoms is optionally replaced by (—O—), phenyl, succinimdyl, or (—NH—) and wherein the chain is optionally substituted on carbon with one or more (e.g. 1, 2, 3, or 4) substituents selected from ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, amino, cyano, nitro, halo, hydroxy, oxo (=O), carboxy, phenyl, phenoxy, 5-6-membered monocyclic heteroaryl, and 5-6-membered monocyclic heteroaryloxy.

In another embodiment the linker is of the formula W-A wherein A is ($C_1$-$C_{24}$)alkyl, ($C_2$-$C_{24}$)alkenyl, ($C_2$-$C_{24}$)alkynyl, ($C_3$-$C_8$)cycloalkyl, ($C_6$-$C_{10}$)aryl or a combination thereof, wherein W is —N(R)C(=O)—, —C(=O)N(R)—, —OC(=O)—, —C(=O)O—, —O—, —S—, —S(O)—, —S(O)$_2$—, —N(R)—, —C(=O)—, or a direct bond; wherein each R is independently H or ($C_1$-$C_6$)alkyl.

In another embodiment the linker is of the formula $W^1$—$W^2$—$W^3$—$W^4$—$W^5$ wherein: $W^1$ is —C(=O)—, —C(=O)N(R)—, —C(=O)O—, —S(O)—, —S(O)$_2$— or a direct bond; $W^2$ is ($C_1$-$C_6$)alkyl, ($C_2$-$C_6$)alkenyl, ($C_2$-$C_6$) alkynyl, ($C_3$-$C_8$)cycloalkyl or ($C_6$-$C_{10}$)aryl or a combination thereof; $W^3$ is —N(R)C(=O)—, —C(=O)N(R)—, —OC(=O)—, —C(=O)O—, —O—, —S—, —S(O)—, —S(O)$_2$—, —C(=O)—, —N(R)—, or is absent; $W^4$ is ($C_1$-$C_6$)alkyl, ($C_2$-$C_6$)alkenyl, ($C_2$-$C_6$)alkynyl, ($C_3$-$C_8$)cycloalkyl or ($C_6$-$C_{10}$)aryl or a combination thereof or is absent; and $W^5$ is —N(R)C(=O)—, —C(=O)N(R)—, —OC(=O)—, —C(=O)O—, —O—, —S—, —S(O)—, —S(O)$_2$—, —C(=O)—, —N(R)—, succinimidyl or absent, provided that when $W^4$ is absent $W^5$ is absent; and wherein each R of $W^1$, $W^3$ or $W^5$ is independently H or ($C_1$-$C_6$)alkyl. It is understood that $W^1$ is the point of attachment of the linker to the compound of formula I and that any alkyl, alkenyl, alkynyl, cycloalkyl or aryl of $W^2$ or $W^4$ can be monovalent or divalent.

In another embodiment the linker is a radical formed from a peptide.

In another embodiment the linker is a radical formed from an amino acid.

In another embodiment the linker is a radical formed from poly-L-glutamic acid, poly-L-aspartic acid, poly-L-histidine, poly-L-ornithine, poly-L-serine, poly-L-threonine, poly-L-tyrosine, poly-L-leucine, poly-L-lysine-L-phenylalanine, poly-L-lysine or poly-L-lysine-L-tyrosine.

In another embodiment the linker is of the formula W—(CH$_2$)$_n$ wherein, n is between about 1 and about 10; and W is —N(R)C(=O)—, —C(=O)N(R)—, —OC(=O)—, —C(=O)O—, —O—, —S—, —S(O)—, —S(O)$_2$—, —C(=O)—, —N(R)—, or a direct bond; wherein each R is independently H or ($C_1$-$C_6$)alkyl.

In another embodiment the linker has a formula of:

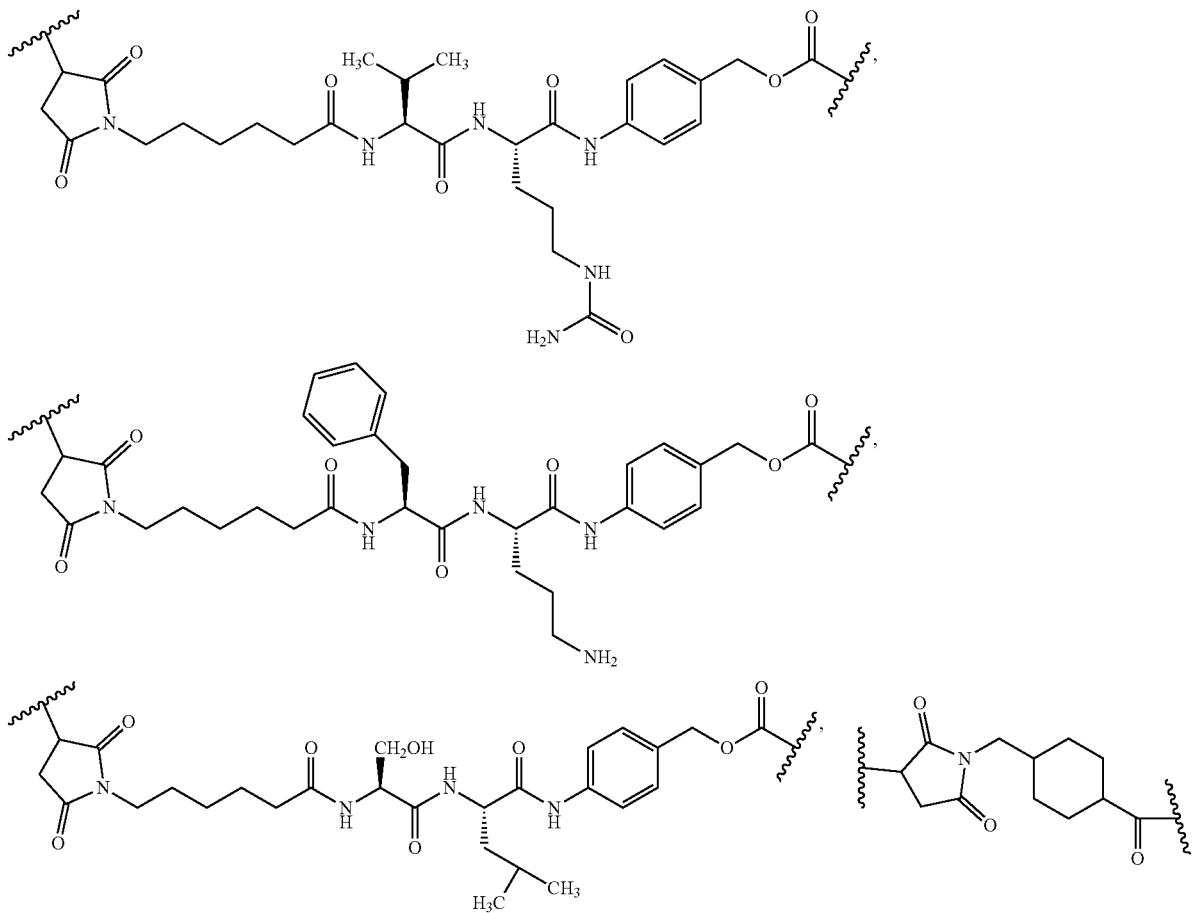

wherein the wavy line at the left depicts the point of attachment to the targeting moiety and wherein the wavy line at the right is the point of attachment to the remainder of the compound of formula I.

In another embodiment the linker has a formula of:

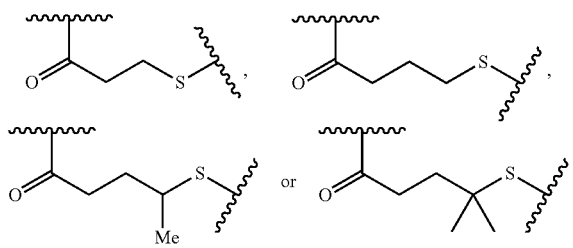

wherein the wavy line at the right depicts the point of attachment to the targeting moiety and wherein the wavy line at the left is the point of attachment to the remainder of the compound of formula I.

In another embodiment the linker is released from the remainder of the compound of formula I when administered to a biological system to generate the drug substance, i.e. active ingredient (the compound of formula II), as a result of spontaneous chemical reaction(s), enzyme catalyzed chemical reaction(s), photolysis, and/or metabolic chemical reaction(s) or by some other process. In another embodiment the linker is not released from the compound of formula I when administered to a biological system.

Targeting Moiety

As used herein the term "targeting moiety" includes but is not limited to any moiety that can selectively target a receptor, enzyme, protein, membrane, cell, cell type (e.g. cancer cell), tissue or that can cross a biological barrier (e.g. the gut wall or the blood-brain barrier) in an assisted or unassisted fashion. Targeting moieties include but are not limited to proteins, antibodies, monoclonal antibodies, sugars and glycosylated proteins or other molecules that are known to preferentially interact with biomolecules, membranes, proteins, cells and tissues. As used herein the term "protein" comprises 21 or more amino acids.

Several purified monoclonal antibodies useful in binding to different clusters of differentiation (cell surface molecules) that are associated with various cancers have been developed. With the broad array of purified monoclonal antibodies that have been developed, ADCs developed from monoclonal antibodies to CD30, CD33, CD70, EGFR, Her2 and CEA attached to one or more cytotoxic agents have been among the more extensively studied.

In one embodiment the targeting moiety is a protein capable of binding to tumor cell membranes, tumor cell receptors, and/or capable of being internalized into tumor cells.

In another embodiment the targeting moiety is a protein that comprises a cysteine residue and is capable of binding to tumor cell membranes, tumor cell receptors, and/or capable of being internalized into tumor cells.

In another embodiment the targeting moiety is a monoclonal antibody.

In another embodiment the monoclonal antibody is an antibody to CD30, CD33, CD70, EGFR, Her2 or CEA. The following documents relate to specific monoclonal antibodies, their purification and methods for the formation of their respective antibody-drugs conjugates (1. Anti-CD30/cAC10: Sun, M. M. C., et al., Bioconjugate Chem., 2005, 16, 1282-1290; McDonagh, C. F., et al., Protein Engineering, Design & Selection, 19, 299-307; Doronina, S. O., et al., Nature Biotechnology, 2003, 21, 778-784. 2. Anti-CD79b: Doronina, S. O., et al., Bioconjugate Chem., 2006, 17, 114-124; Poison, A. G., et al., Blood, 2007, 110, 616623. 3. Anti-CD19, Anti-CD20, Anti-CD21, Anti-CD22, Anti-CD72, Anti-CD79b, and Anti-CD-180: Poison, A. G., et al., Cancer Res., 2009, 69, 2358-2364. 4. huC242: Erickson, H. K., et al., Cancer Res., 2006, 66, 4426-4433; Xie, H., et al., J. Pharmacol Exp. Ther., 2004, 308, 1073-1082. 5. Anti-CD30 and Anti-CD70: Burke, P. J., et al., Bioconjugate Chem., 009, 20, 1242-1250. 6. Anti-CD70: Alley, S. C., et al., Bioconjugate Chem., 2008, 19, 759-765. 7. Anti-Her-2 and Anti-CD19: Chari, R V, et al., Cancer Res., 1991, 52, 127-131. Lewis Phillips, G. D., et al., Cancer Res., 2008, 68, 9280-9290. 8. Anti-CEACAM5: Govindan, S. V., et al., Clin. Cancer Res., 2009, 15, 6052-6061).

Processes for preparing compounds of the invention including compounds of formula I are provided as further embodiments of the invention and are illustrated by the following procedures in which the meanings of the generic radicals are as given above unless otherwise qualified.

The starting materials employed in the synthetic methods described herein are commercially available, have been reported in the scientific literature, or can be prepared from readily available starting materials using procedures known in the field. It may be desirable to optionally use a protecting group during all or portions of the above described synthetic procedures. Such protecting groups and methods for their introduction and removal are well known in the art. See Greene, T. W.; Wutz, P. G. M. "Protecting Groups In Organic Synthesis" second edition, 1991, New York, John Wiley & Sons, Inc.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine topoisomerase inhibition activity or cytotoxic activity using the standard tests described herein, or using other similar tests which are well known in the art. Compounds of the present invention can contain chiral centers, for example, the carbon atom in formula I when $R_3$ and $R_4$ are different. Compounds of the present invention can also contain chiral centers, for example, in any of the substituents Y, Z, $R_1$, $R_2$ when $R_3$ and $R_4$ together are =N—$R_2$, and $R_3$ or $R_4$.

In cases where compounds are sufficiently basic or acidic, a salt of a compound of the invention can be useful as an intermediate for isolating or purifying a compound of the invention. Additionally, administration of a compound of the invention as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Representative compounds of the invention can be prepared as illustrated on the schemes below.

Scheme 1 illustrates a general method for the preparation of certain N-acyl derivatives of formula I and Scheme 2 illustrates a general method for the preparation of carbamate derivatives of formula I (R is H or —($C_1$-$C_6$)alkyl).

Scheme 1

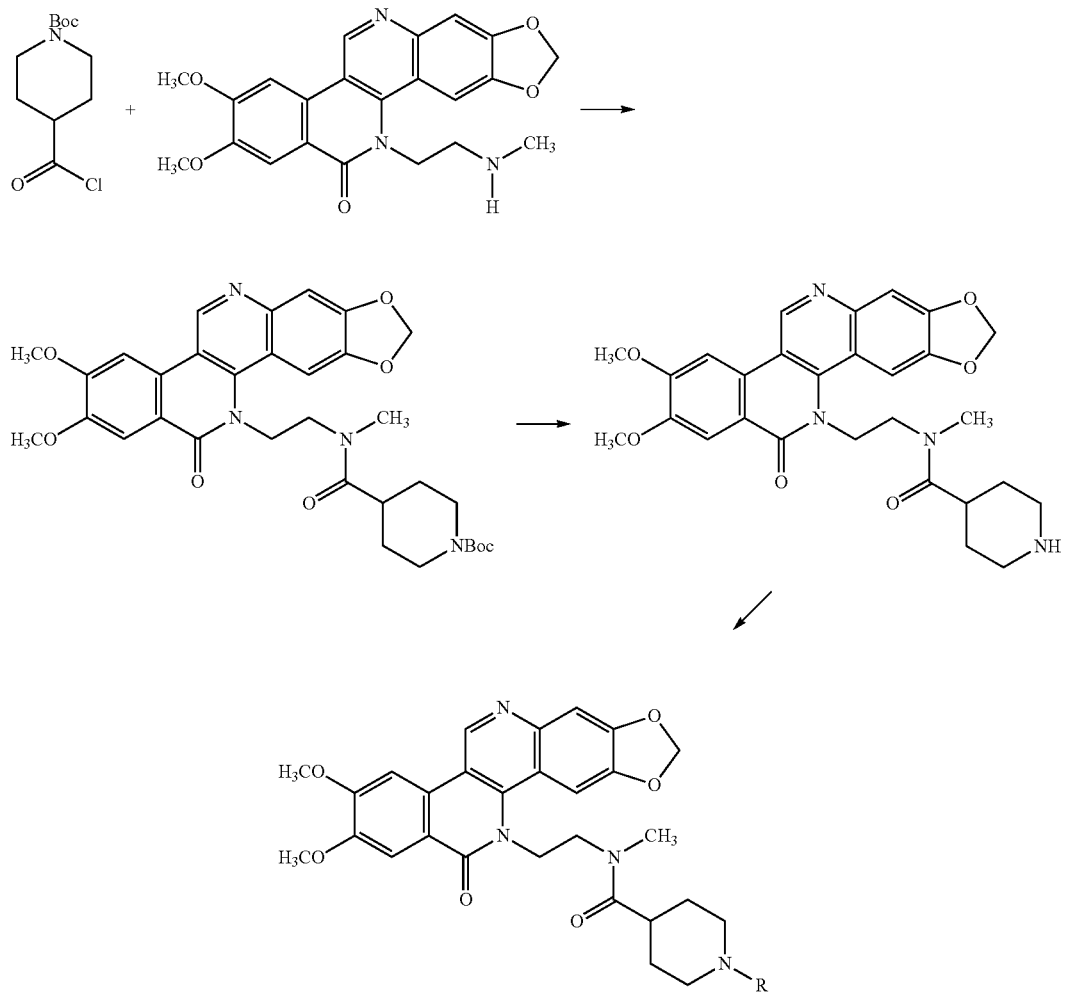

Scheme 2

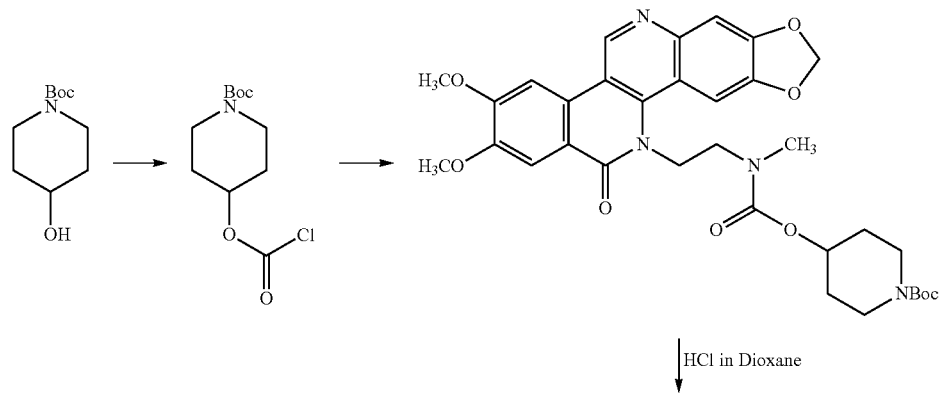

31

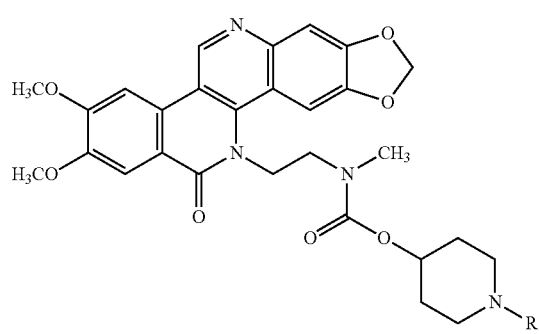

32

-continued

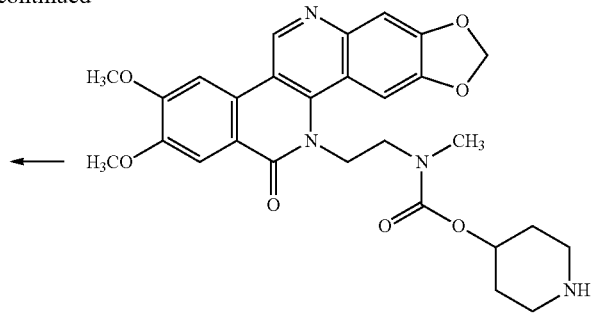

One advantage of the N-acyl compounds of formula I is that a disulfide can be incorporated into the N-acyl portion of the molecule. Increased levels of glutathione in tumor cells provides an environment that more readily can interact with disulfide moiety and form the free sulphydryl group, that as a cascading prodrug will undergo a self-immolative process that will result in the formation of the compound of formula II. One example of such a derivative is the compound:

-continued

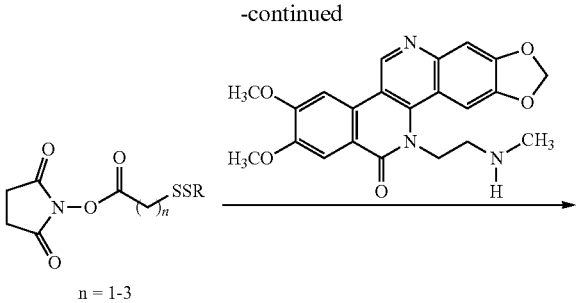

n = 1-3

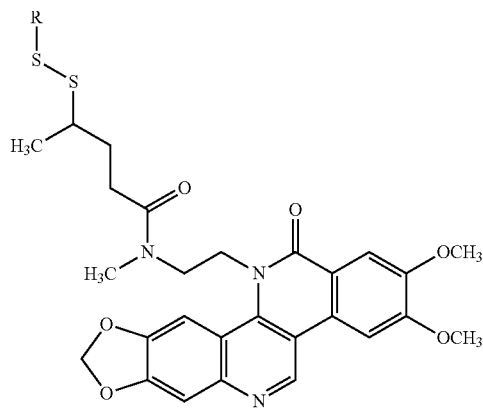

wherein R is a $(C_1-C_{10})$alkyl, phenyl, or a 5-6-membered monocyclic heteroaryl wherein any phenyl or 5-6-membered monocyclic heteroaryl is optionally substituted with one or more halogen, $(C_1-C_4)$alkyl, or —O$(C_1-C_4)$alkyl.

Scheme 3 illustrates a general method for the preparation of self-immolative N-acyl disulfide derivatives.

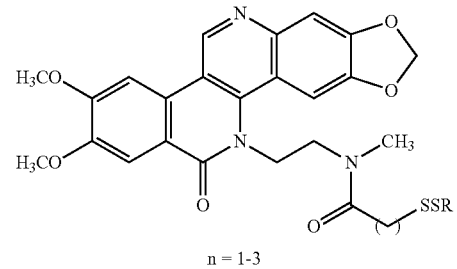

n = 1-3 wherein R is a $(C_1-C_{10})$alkyl, phenyl, or a 5-6-membered monocyclic heteroaryl wherein any phenyl or 5-6-membered monocyclic heteroaryl is optionally substituted with one or more halogen, $(C_1-C_4)$alkyl, or —O$(C_1-C_4)$alkyl.

Schemes 4 and 5 illustrate general methods for the preparation of chiral alpha-methyl self-immolative N-acyl disulfide derivatives.

Scheme 4

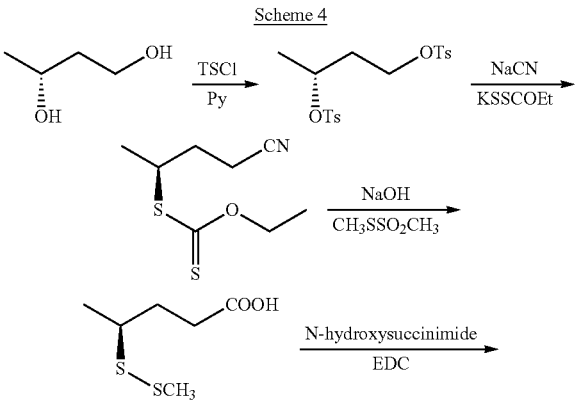

Scheme 3

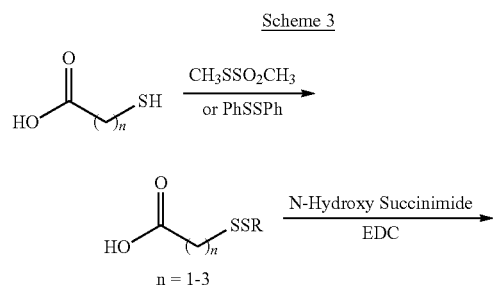

n = 1-3

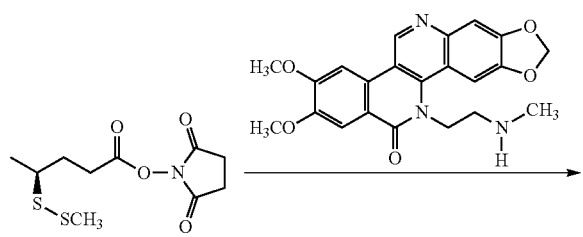

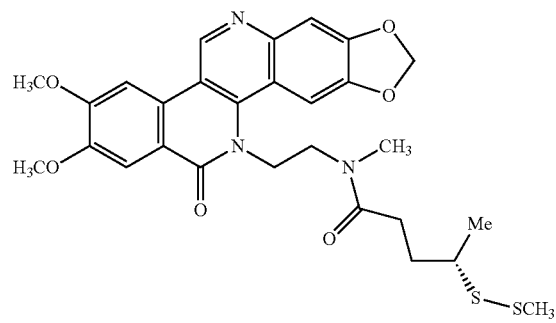

Scheme 6 illustrates a general method for the preparation of chiral alpha, alpha-dimethyl self-immolative N-acyl disulfide derivatives.

Scheme 6

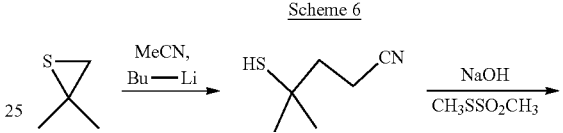

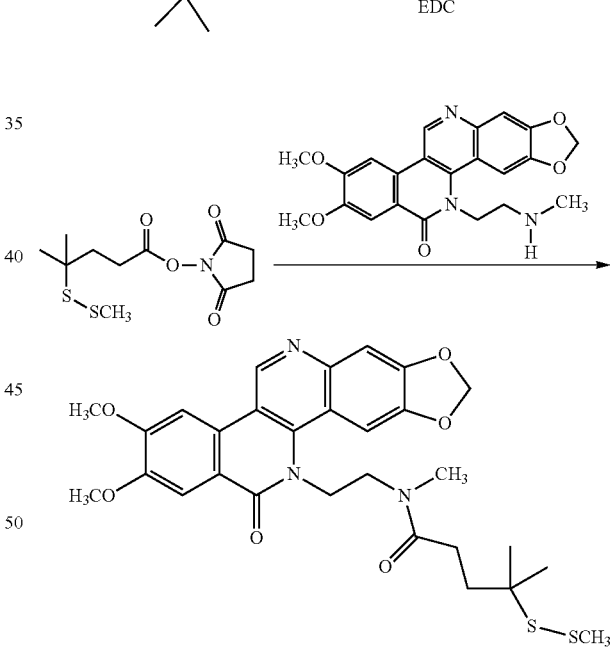

Scheme 5

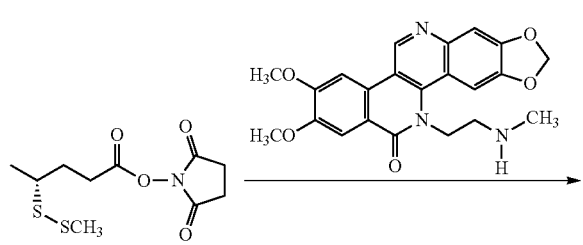

N-Acyl or N-alkyloxy derivatives of the compound of formula I also include moieties that can be selectively cleaved by enzymes that are elevated in tumor cells or within the more acidic cellular environment of tumor cells. These cleavage transformations will result in the formation of the compound of formula II. Specific examples of such derivatives are illustrated herein below.

One example is a self-immolitive compound of formula I that is activated (e.g., cleaved) by cathepsin B such as the compound of the following structure:

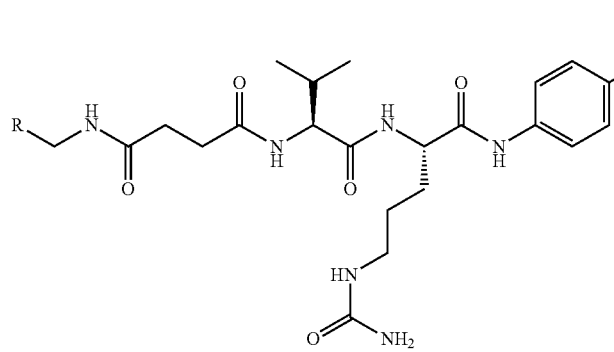

15 wherein R is a (C$_1$-C$_{10}$)alkyl, —O(C$_1$-C$_{10}$)alkyl, phenyl, or a 5-6-membered monocyclic heteroaryl wherein any phenyl or 5-6-membered monocyclic heteroaryl is optionally substituted with one or more halogen, (C$_1$-C$_4$)alkyl, or —O(C$_1$-C$_4$)alkyl. Scheme 7 illustrates a general method for the preparation of a compound of formula I that is a cathepsin B substrate wherein R is a (C$_1$-C$_{10}$)alkyl, —O(C$_1$-C$_{10}$)alkyl, phenyl, or a 5-6-membered monocyclic heteroaryl wherein any phenyl or 5-6-membered monocyclic heteroaryl is optionally substituted with one or more halogen, (C$_1$-C$_4$) alkyl, or —O(C$_1$-C$_4$)alkyl.

Scheme 7

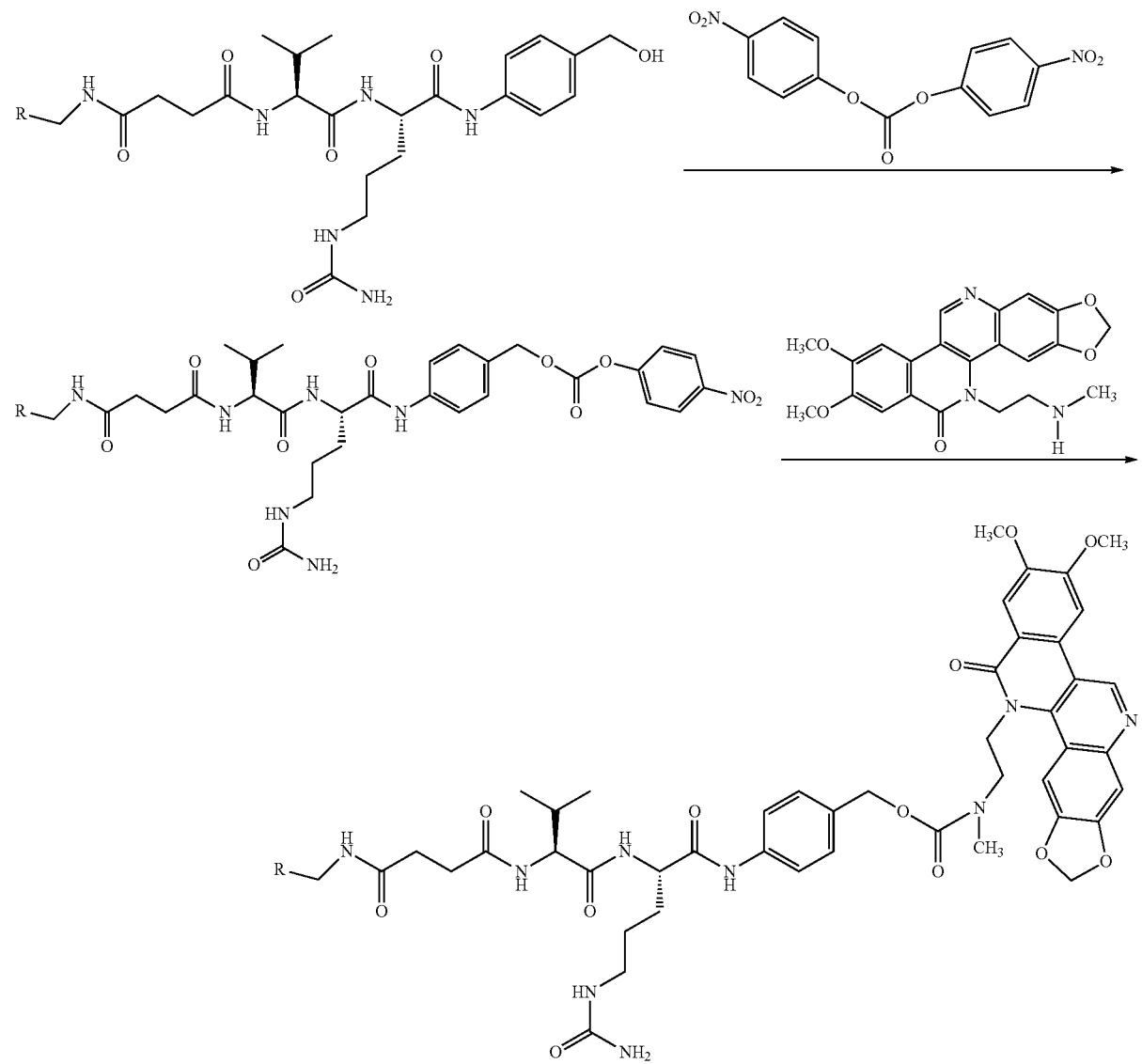

Another example is a self-immolitive compound of formula I that is activated (e.g., cleaved) by acid such as the compound of the following structure:

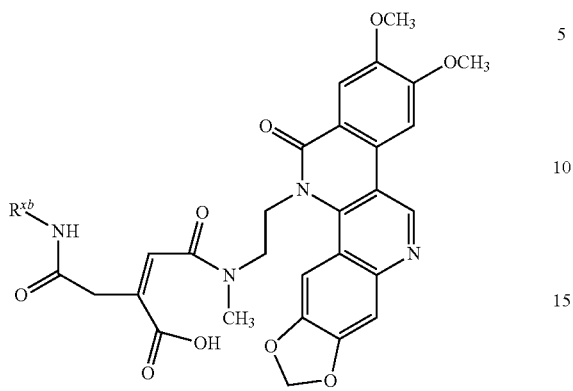

wherein $R^{xb}$ is a $(C_1-C_{10})$alkyl, $-O(C_1-C_{10})$alkyl, phenyl, or a 5-6-membered monocyclic heteroaryl wherein any phenyl or 5-6-membered monocyclic heteroaryl is optionally substituted with one or more halogen, $(C_1-C_4)$alkyl, or $-O(C_1-C_4)$alkyl. Scheme 8 illustrates a general method for the preparation of a compound of formula I that is an acid labile wherein $R^{xb}$ is a $(C_1-C_{10})$alkyl, $-O(C_1-C_{10})$alkyl, phenyl, or a 5-6-membered monocyclic heteroaryl wherein any phenyl or 5-6-membered monocyclic heteroaryl is optionally substituted with one or more halogen, $(C_1-C_4)$alkyl, or $-O(C_1-C_4)$alkyl.

Scheme 8

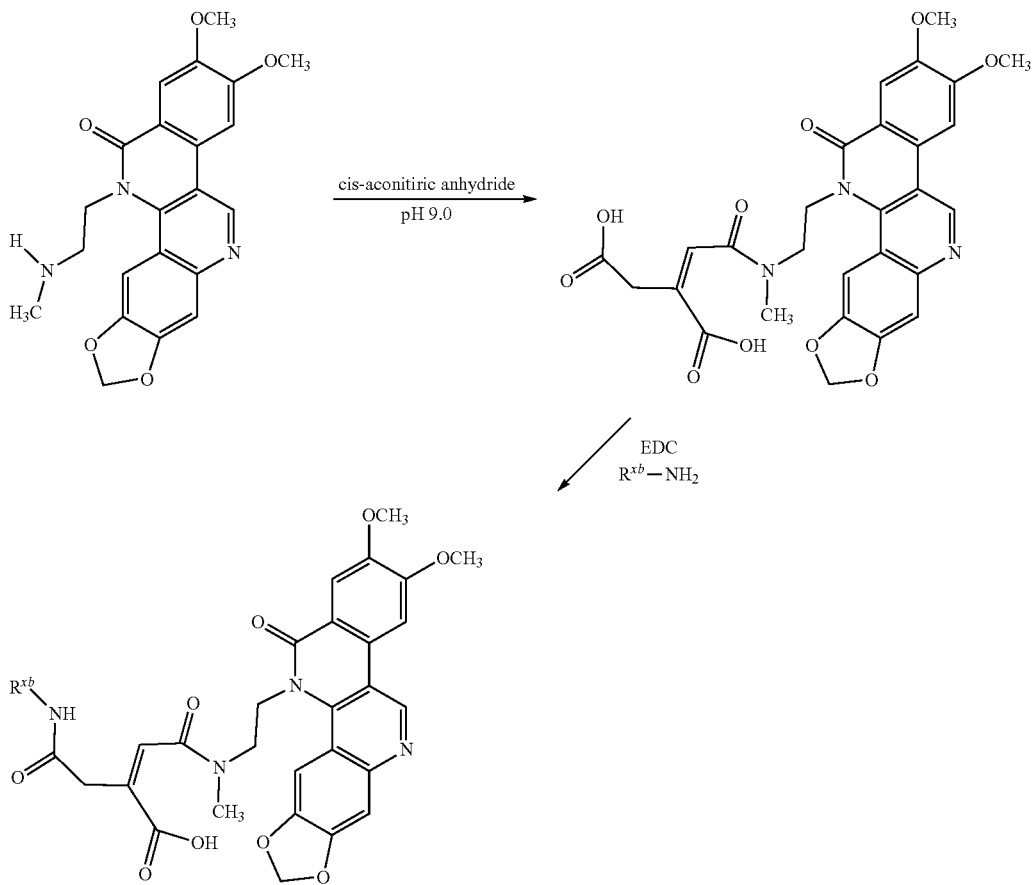

N-Acyl or N-alkyloxy derivatives of the compound of formula I can also include moieties which are recognized by transport mechanisms on the surface of tumor cells and permit enhanced uptake into the tumor. Such derivatives include compounds of formula I that comprise a folate. Folate is known to provide a mechanism for enhanced selectivity with regards to uptake into tumor cells. Specific examples of such agents are illustrated herein below.

One example of a self-immolitive compound of formula I that includes a folate moiety linked to the remainder of the compound of formula I with an acid labile linker is the compound of the following structure:

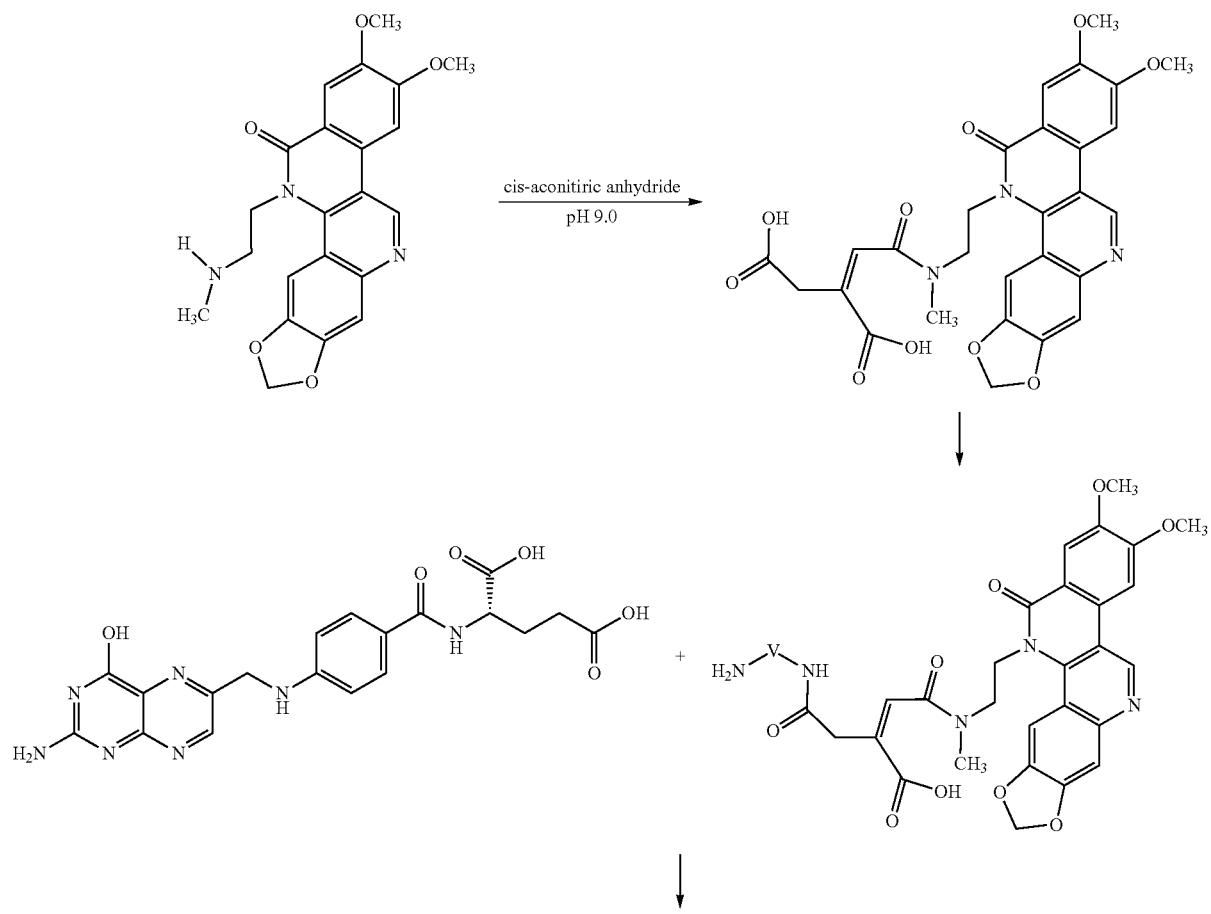

wherein V together with two nitrogen atoms as shown attached to V is a polyamine.

Schemes 9a and 9b illustrates a general method for the preparation of folic acid linked compounds of formula I.

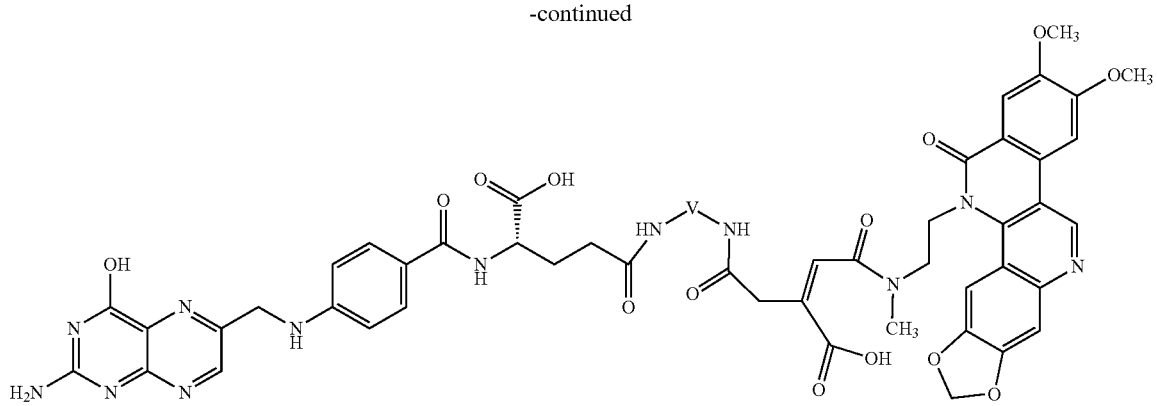
wherein V together with two nitrogen atoms as shown attached to V is a polyamine. In one embodiment the polyamine comprises alginate derivatives, bovine serum albumin, polylysine, or lysozyme. In one embodiment polyamine comprises a diaminoalkyl.
Scheme 9b
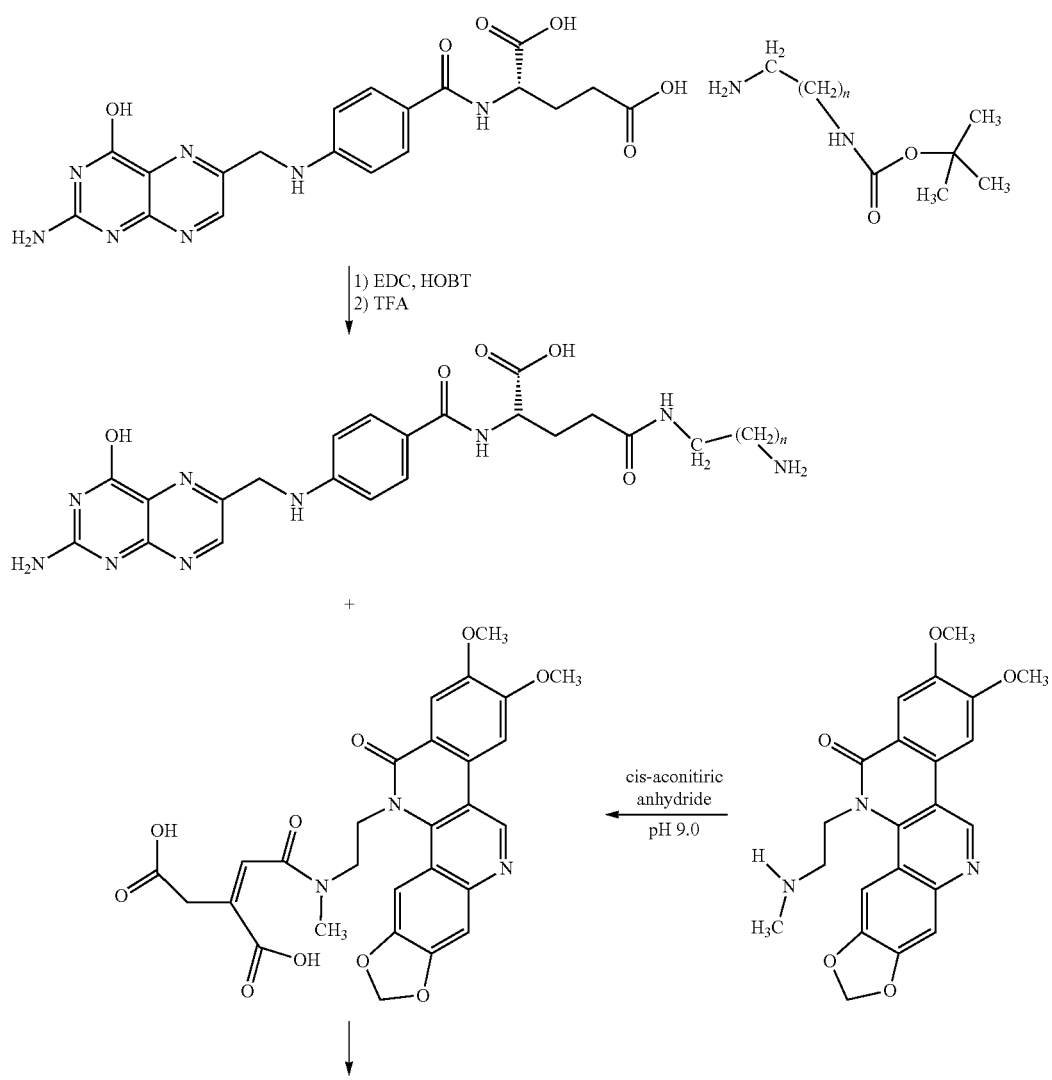

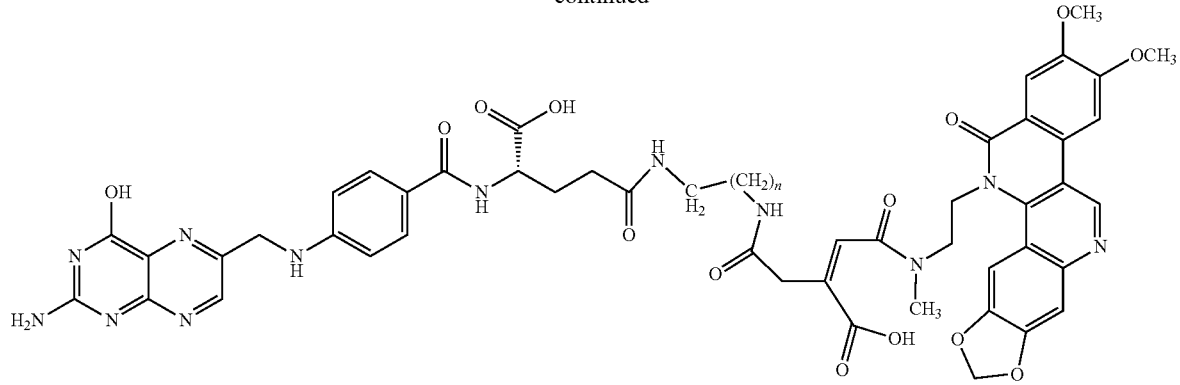
wherein n is 1-6.
Another example of a self-immolitive compound of formula I that includes a folate moiety linked to the remainder of the compound of formula I with a disulfide linker is the compound of the following structure:
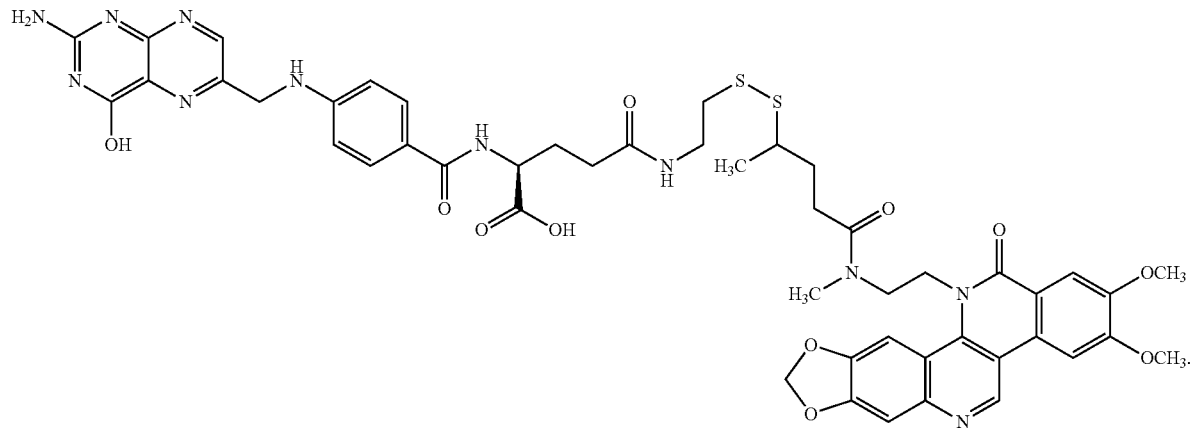 [SMILES: COc1cc2c(=O)n(CCN(C)C(=O)CCC(C)SSCCNC(=O)CC[C@H](NC(=O)c3ccc(NCc4cnc5nc(N)nc(O)c5n4)cc3)C(=O)O)c3c4cc5c(cc4ncc3c2cc1OC)OCO5]
Scheme 10 illustrates a general method for the preparation of a self-immolative disulfide prodrug derivative of the compound of formula 1.
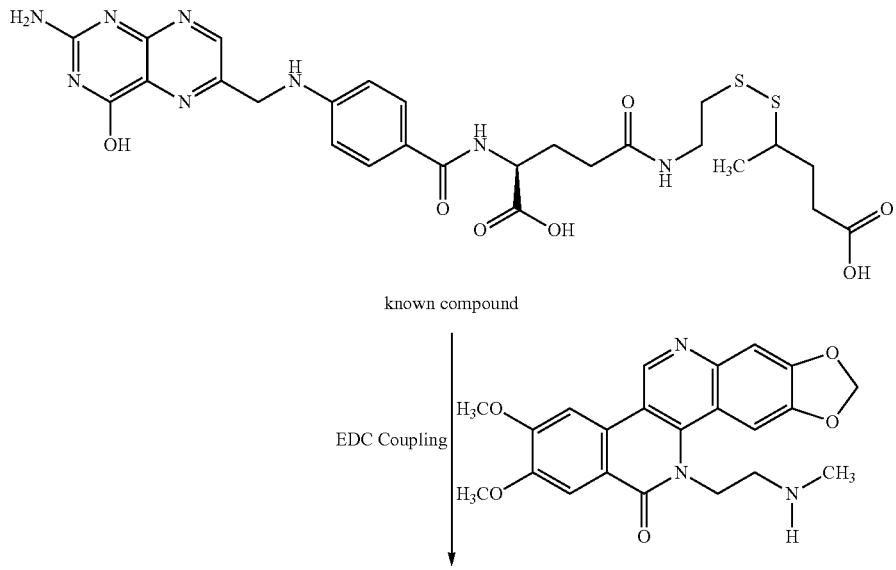

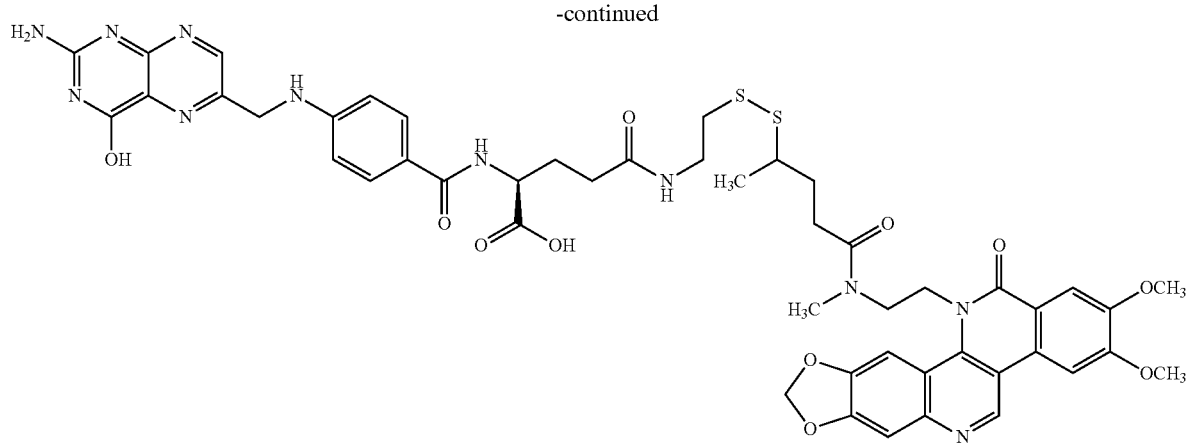

Compounds of formula I can also include moieties that are selective for the sigma-2 receptors that are highly expressed in human pancreatic cancer. The SW43 moiety has been shown to be selective for to sigma-2 receptors that are highly expressed in human pancreatic. Linkage of a selective sigma-2 to the remainder of the compound of formula I would be expected to be labile within tumor cells a may provide a means for both selective tumor uptake and selective activation with the tumor cell.

One example includes a compound of formula I that includes SW43 and is activated by cathepsin B that has the structure:

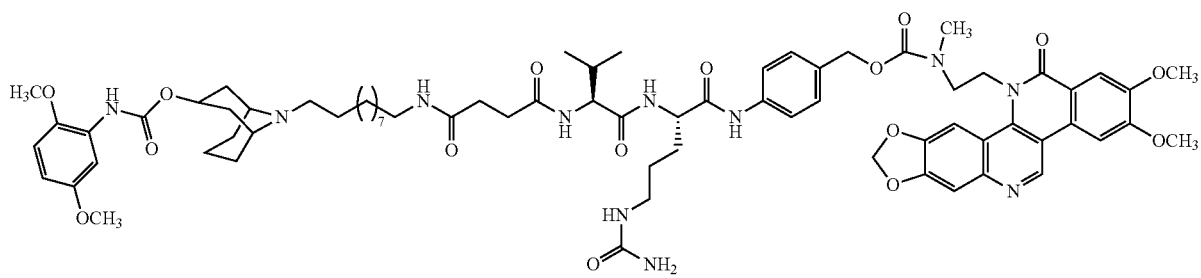

Scheme 11 illustrates a general method for the preparation of a capthepsin B activated prodrug of the compound of formula 1 linked to SW43.

Scheme 11

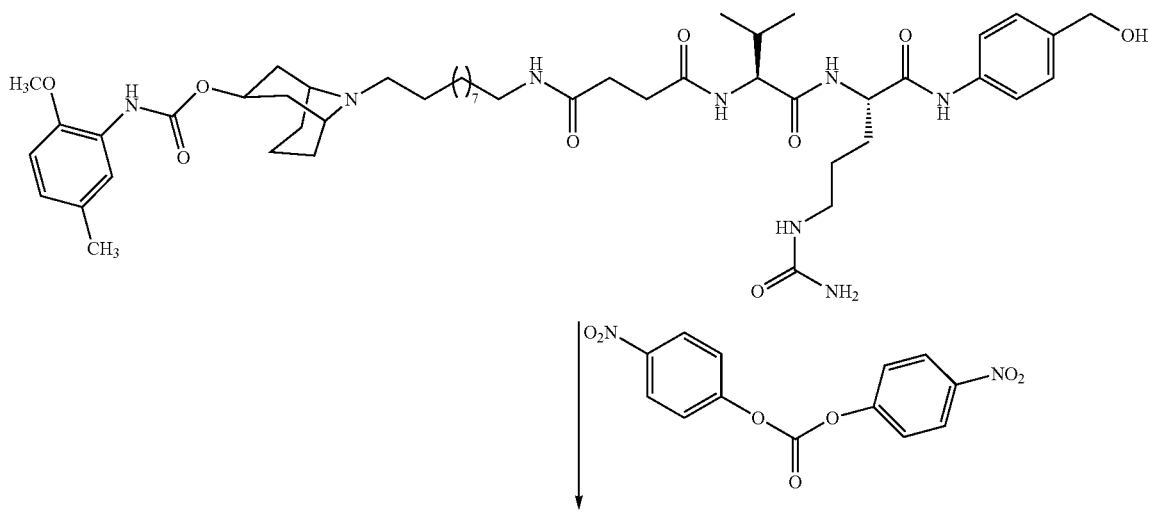

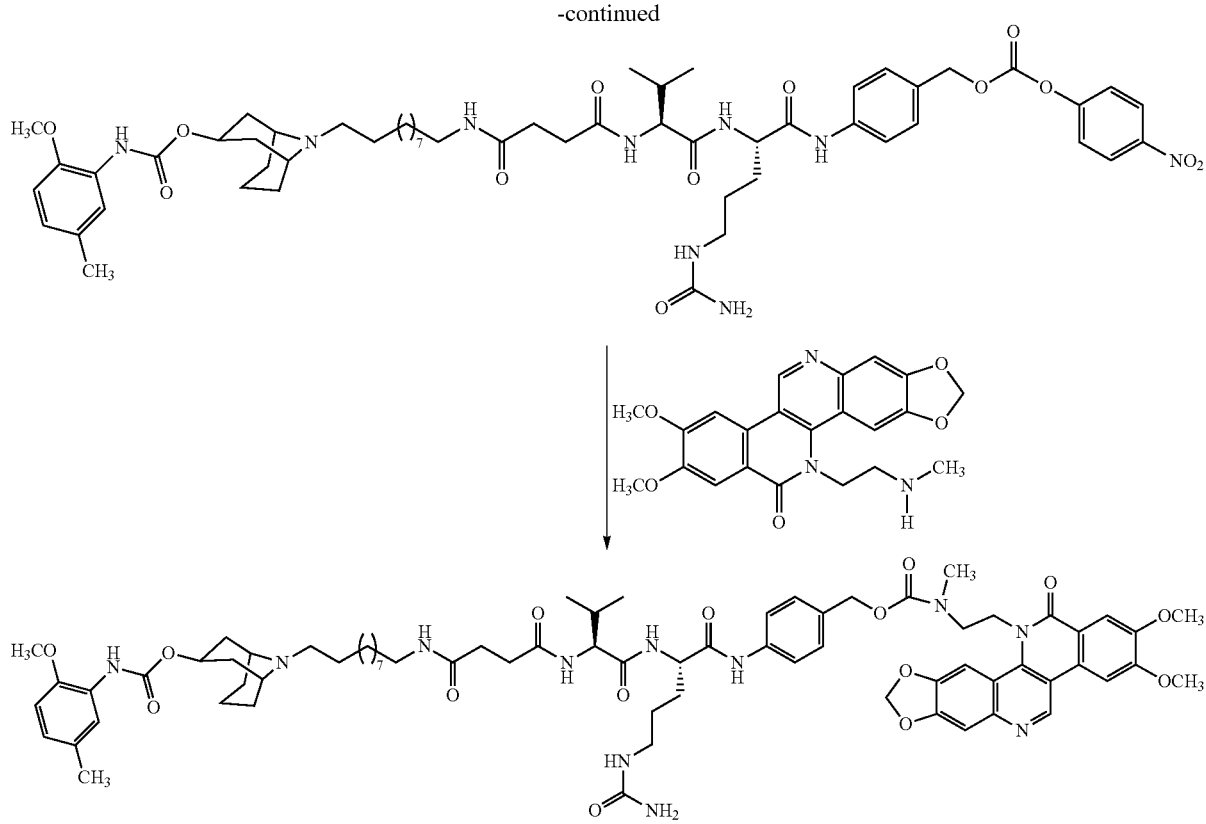
Another example of a compound of formula I that includes SW43 wherein SW43 is linked to the remainder of the compound of formula I by a disulfide is the compounds
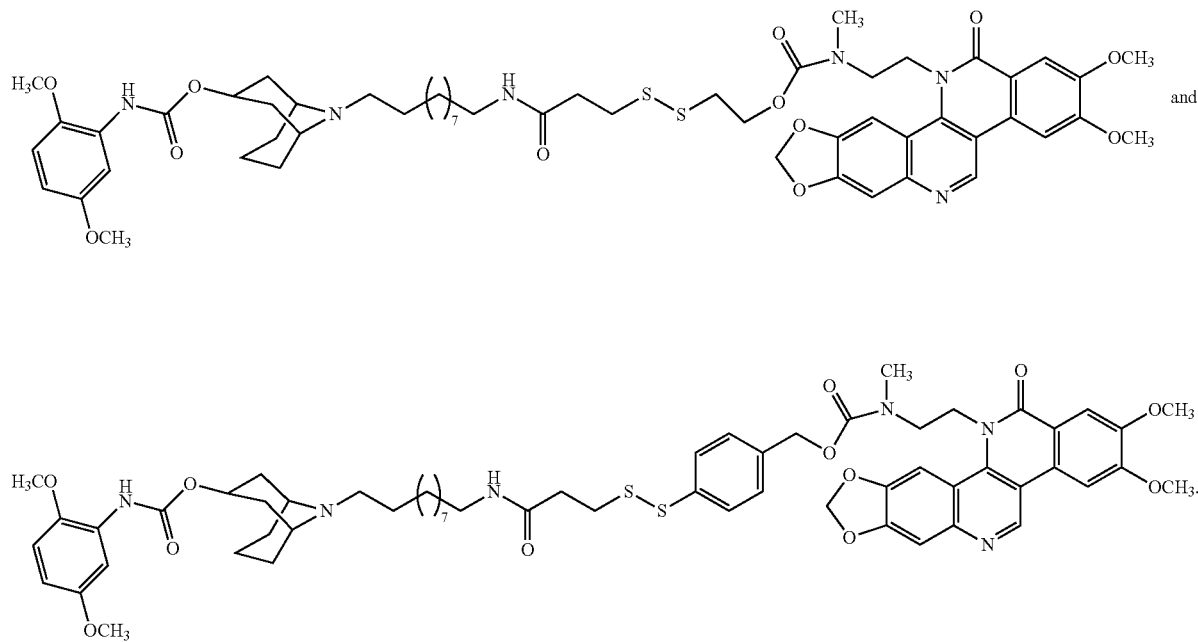
Schemes 12 and 13 illustrate general methods for the preparation of a such compounds of formula I.

Scheme 12
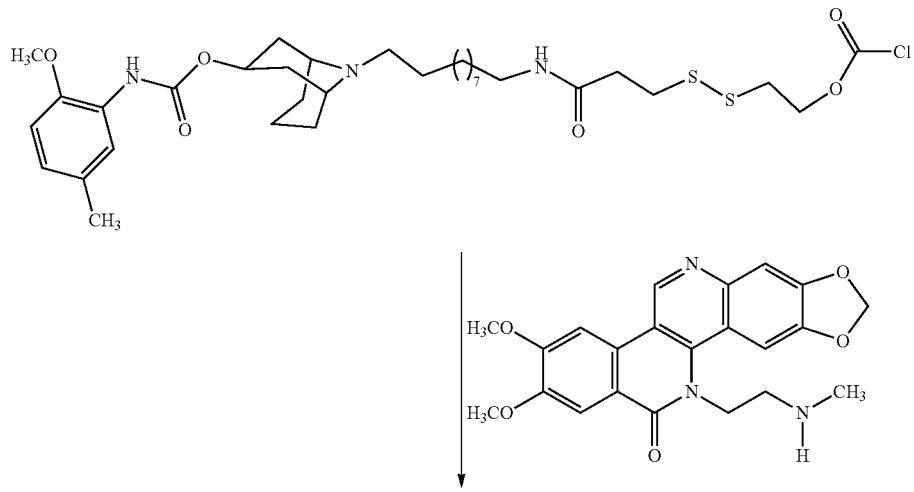
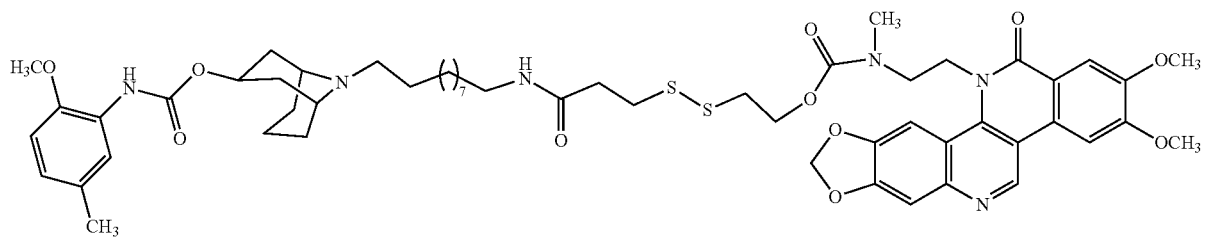
Scheme 13
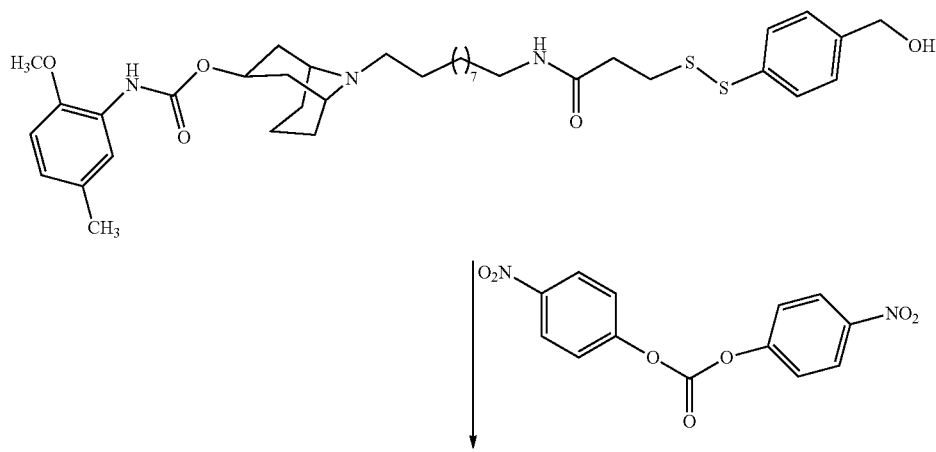

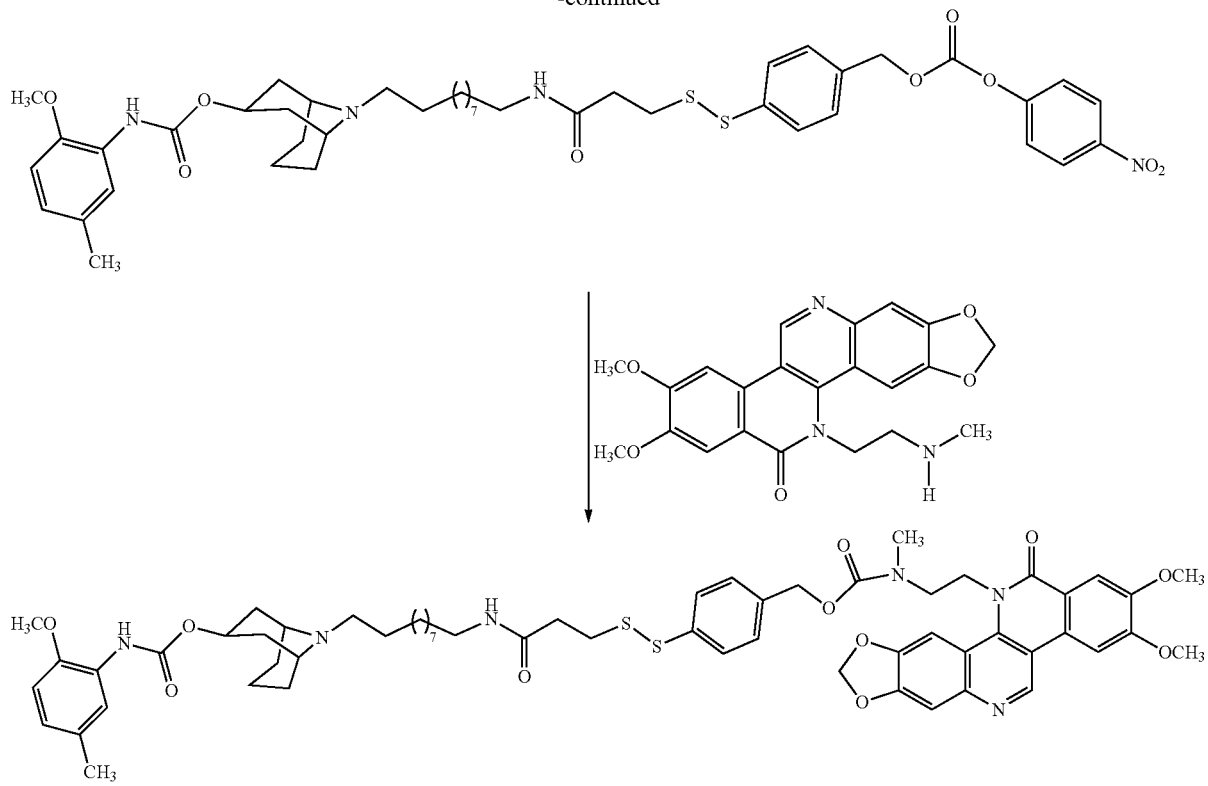

Another class of compounds of formula I include antibodies (e.g., monoclonal antibodies) that are linked (e.g., through a linker) to a residue of a compound of formula II. These compounds of formula I are also known as antibody drug conjugates (ADCs). As described herein the residue of the compound of formula II is formed by the removal of the hydrogen from the "methylamine" amine moiety of the compound of formula II. The linker is thus connected to the nitrogen atom of the methylamine moiety through the creation of the open valence from the removal of the hydrogen. The linkers of the ADCs can be cleaved in tumor cells; these cells are also capable of interacting with the antibodies of the compounds of formula I as these antibodies are highly selective for receptors on certain types of tumors. These compounds of formula I thus provide an additional class of tumor-specific cancer chemotherapeutic agents that will release the compound of formula II (i.e., the active compound).

There are several standard methods for forming antibody drug conjugates (ADCs). These methods generally involve connecting the compound of formula II to an antibody through an appropriate linker wherein the linker comprises a group that is capable of forming a bond (e.g., a covalent bond with an antibody). One method for accomplishing this involves attaching the linker to the compound of formula II. This drug-linker intermediate is then connected to an antibody through the group of the linker that is capable of forming the bond with the antibody. The schemes below outline several potent linker-drug intermediates (i.e. intermediates that comprise the compound of formula II and a "linker") bearing a group capable of forming a bond between the intermediate and the antibody (e.g., an electrophilic or reactive substituent). These drug-linker intermediates are embodiments of the invention. These drug-linker intermediates will interact with appropriate functional groups (e.g. thiols, alkyl amines and/or hydroxyl groups) of antibodies (e.g. monoclonal antibodies) to form ADCs. For example, thiol addition products that result in the formation of either thioethers or disulfides have been shown to particularly useful in forming effective ADCs. The maleimide moiety is known to react with the thiol functional group, including the thiol functional groups present in many proteins, to form a succinimidyl-sulfur covalent bond Various methods have generally allowed for linking between 1 to 8 drug molecules per monoclonal antibody. Accordingly, the invention provides for the linking of one or more (e.g. 1, 2, 3, 4, 5, 6, 7, 8, 9, 10 or more) compounds of the invention to an antibody (e.g. monoclonal antibody) through a "linker".

Controlled reduction of purified monoclonal antibody disulfides exposes free thiol groups which are capable of interacting with a reactive group of the "linker". In certain instances the amount to dithiothreitol is limited to allow for fewer thiol groups to be available for interaction with the linker. Using 3.25 and 2.75 molar equivalents of the strong reducing agents dithiothritol DTT and tris(2-carboxyethyl] phosphine TCEP have been used to reduce interchain disulfide bonds to provide free thiols. Partial reduction using the weaker reducing agent aminoethanethiol at pH 5 has been accomplished 500 molar equivalents. TCEP react poorly with maleimides and the excess of this reducing agent does not have to be removed before adding maleimide-containing dug linkers. In addition to partial reduction, a fully reduced monoclonal antibody can be partially re-oxidized with 5,5'-dithiobis-(2-nitrobenzoic acid) DTNB. The extent of reduction can be determined by assaying a portion of the reduction mixture by initial purification through a PD-10 column and titrating the number of antibody-cysteine thiols with 5,5'-dithio-bis(2-nitrobenzoic acid).

The drug-linker intermediate can be added to an appropriate solvent (e.g. ethanol, dimethylacetamide) wherein the resulting solution or mixture can be added to the reduced antibody. For example, the reduced antibodies in a 0.1 M phosphate buffer, pH 7.0, containing 2 mM EDTA, and the drug-linker intermediate are typically allowed to react for 1-20 hours at 0-20° C. Excess and/or unreacted drug-linker can then be quenched with an appropriate reagent such as N-acetylcyteine. Gel filtration over a PD-10 column will remove the quenched drug linker. The resulting ADC can at this point be filter-sterilized.

The ADC reaction mixture can be loaded on a hydroxyapatite column equilibrated with 10 mM sodium phosphate pH 7.0, 10 mM NaCl. After washing with several column volumes of the same buffer, the ADC is typically eluted with 100 mM phosphate, pH 7.0 and 10 mM NaCl. The ADCs can be concentrated and buffer-exchanged into PBS using Amicon Ultrafree centrifugal filter units. The ADC thus formed can be subjected to hydrophobic interaction (RP-HPLC) chromatography in some instances to isolate conjugates with different ratios of drug/antibody.

The methods depicted in the Schemes start from known or commercially available compounds and the reaction steps utilize known reagents and known reaction conditions. The term "mab" represents a monoclonal antibody.

One class of compounds of formula I (e.g., ADCs) include those with linkers known to be cleaved in tumors cells that are also capable of interacting with the lysine moieties of antibodies that are highly selective for receptors on certain types of tumors. These compounds of formula I thus provide an additional class of tumor-specific cancer chemotherapeutic agents that will release the compound of formula II (i.e., the active compound).

Drug-linker intermediates (useful for the preparation of the compounds of formula I (ADCs) comprising a maleimide and a residue of a compound of formula II can be coupled, with and antibody (e.g., monoclonal antibody) to the maleimide moiety of the drug linker intermediate to form an ADC of formula I. These drug linker intermediates are also embodiments of the invention and are described herein below. The maleimide can react with any appropriate functional group of an antibody such as a nucleophilic atom of a nucleophilic group (e.g., a nitrogen of a primary or secondary amine, an oxygen of a hydroxyl or a sulfur of a thiol) to form a bond between the nucleophilic atom of the nucleophilic group of the antibody and the corresponding succinimidyl group (i.e., the reduced from of the maleimide resulting from the reaction of the maleimide moiety and the nucleophilic group). One particular nucleophilic group atom is the nucleophilic amine of a lysine residue of an antibody. Thus, one embodiment provides a drug linker intermediate comprising a compound of formula II linked to a maleimide (e.g., linked through the methylamine nitrogen of the compound of formula II). Scheme 14 shows non-limiting examples of such intermediates.

Scheme 14

Intermediates for conjugating antiboides -- cysteine bsedA

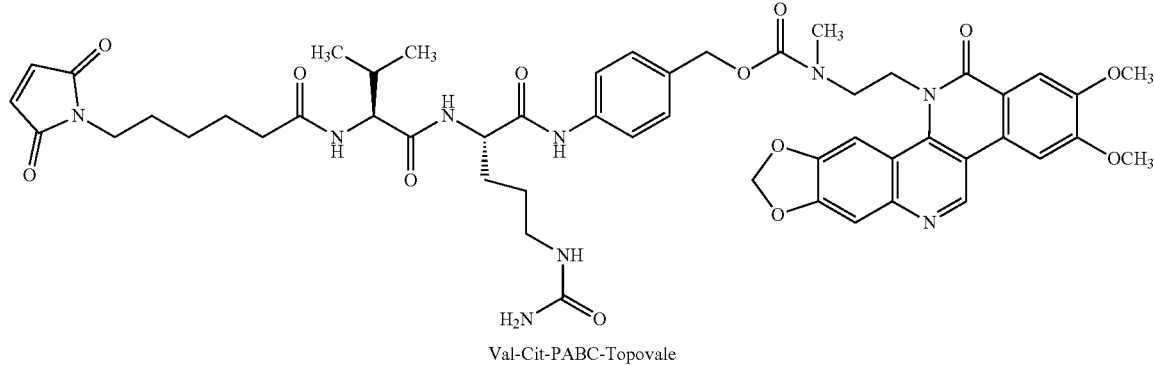

Val-Cit-PABC-Topovale

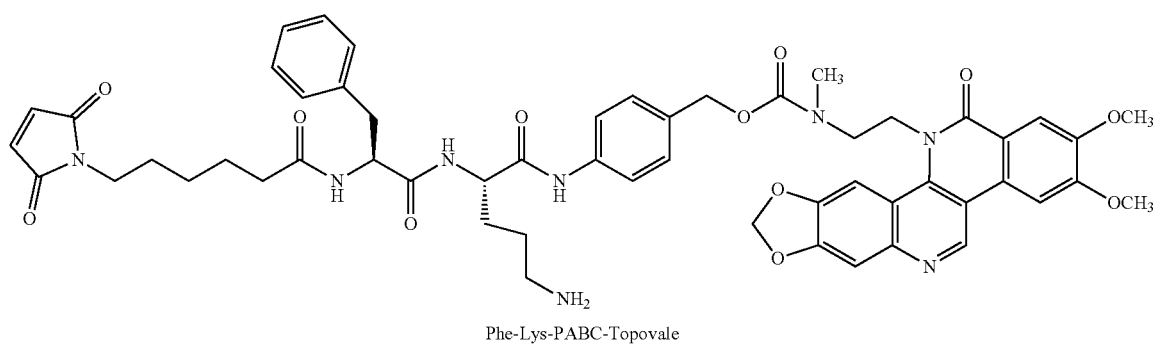

Phe-Lys-PABC-Topovale

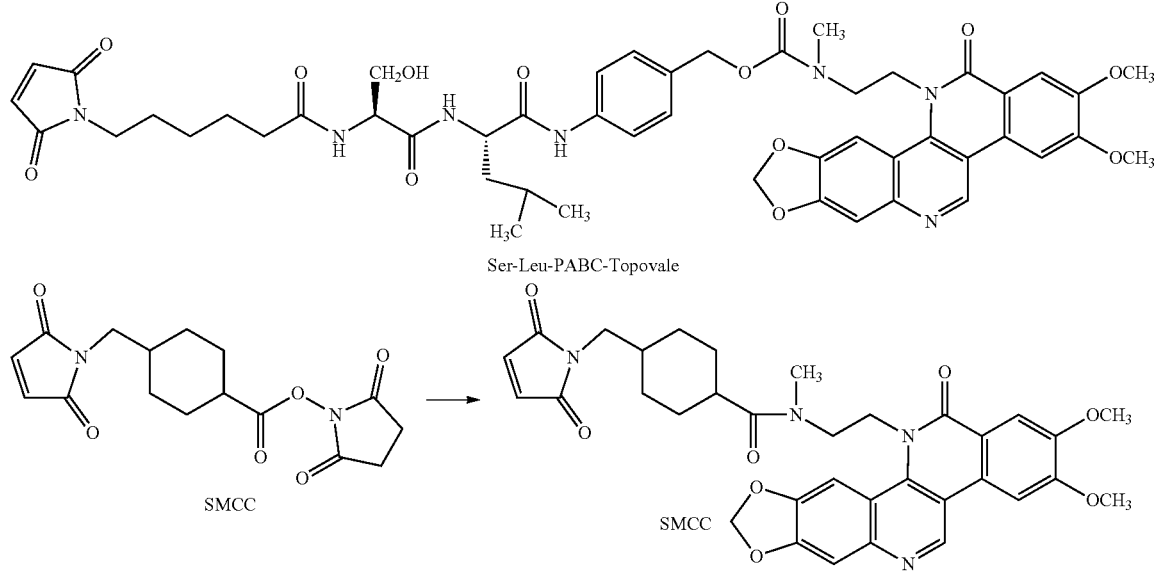
Ser-Leu-PABC-Topovale
SMCC
SMCC
Schemes 15-17 illustrate general methods for preparing drug linker intermediates that can form, for example a lysine-linkage to a tumor-selective antibody.
Scheme 15
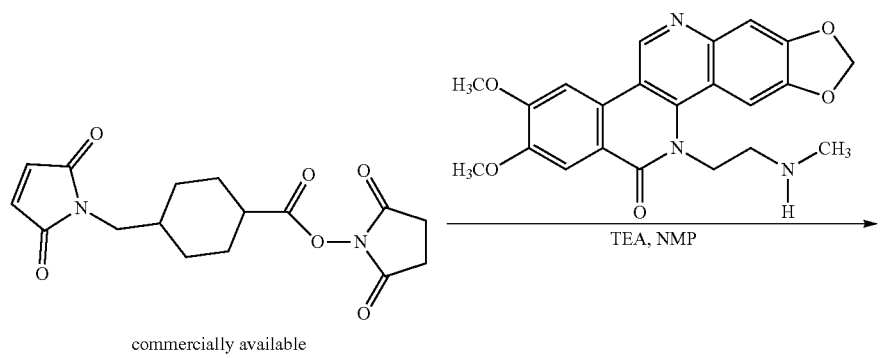
commercially available
TEA, NMP
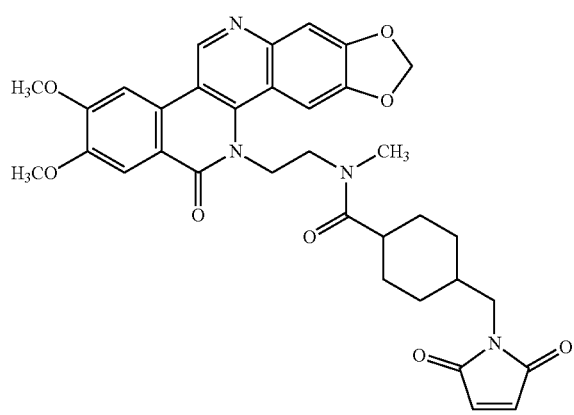

Scheme 16
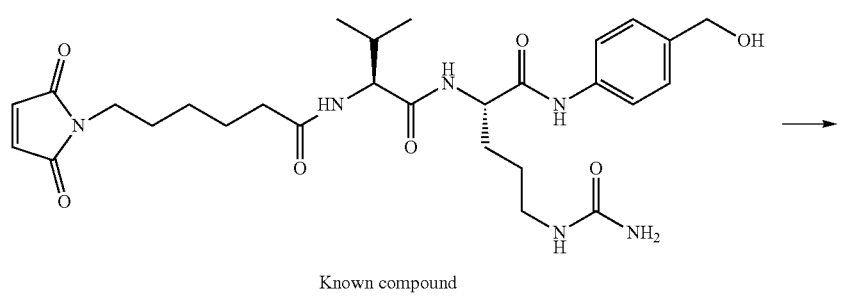
Known compound
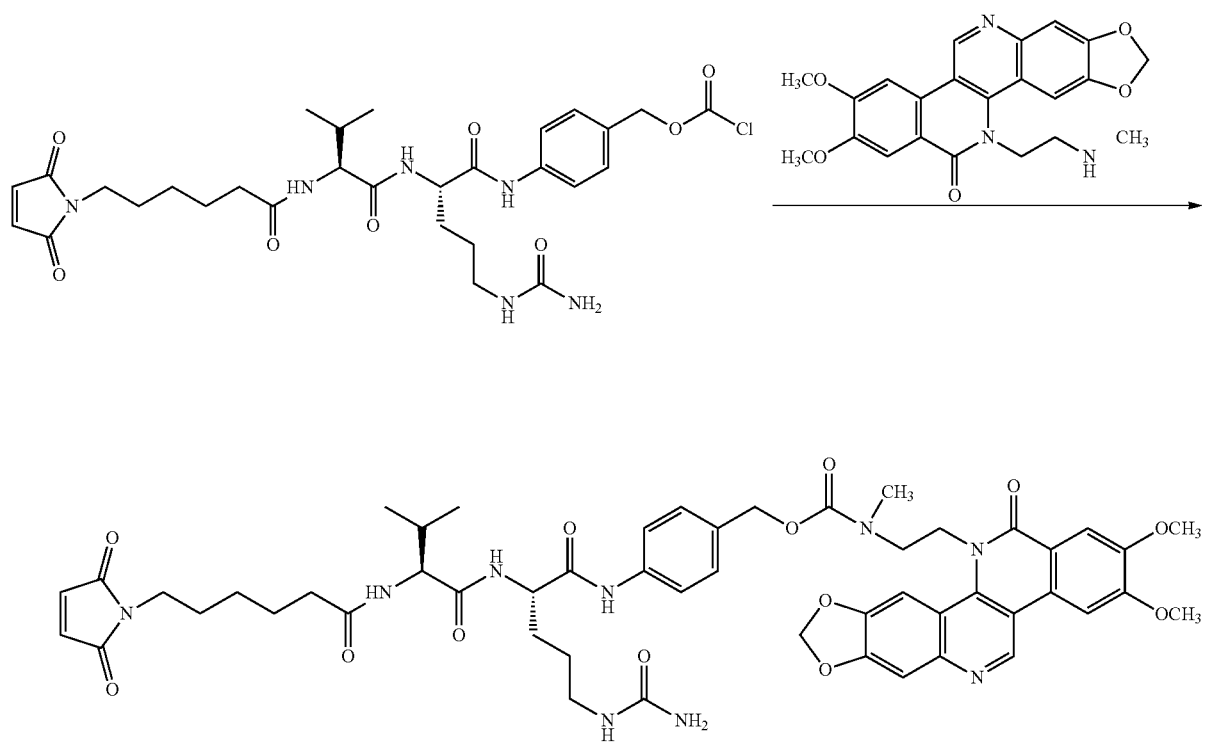
Scheme 17
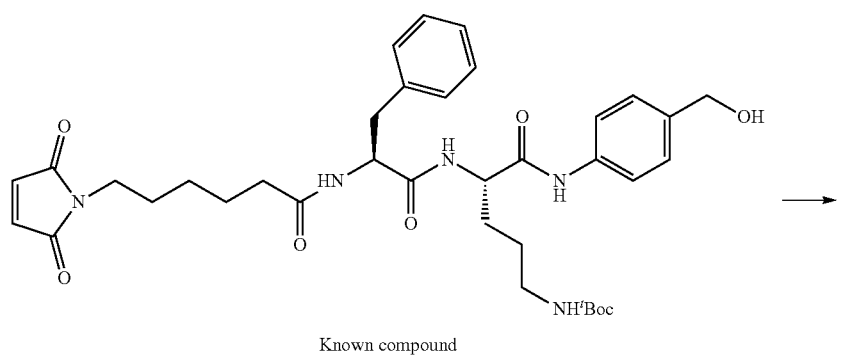
Known compound -continued

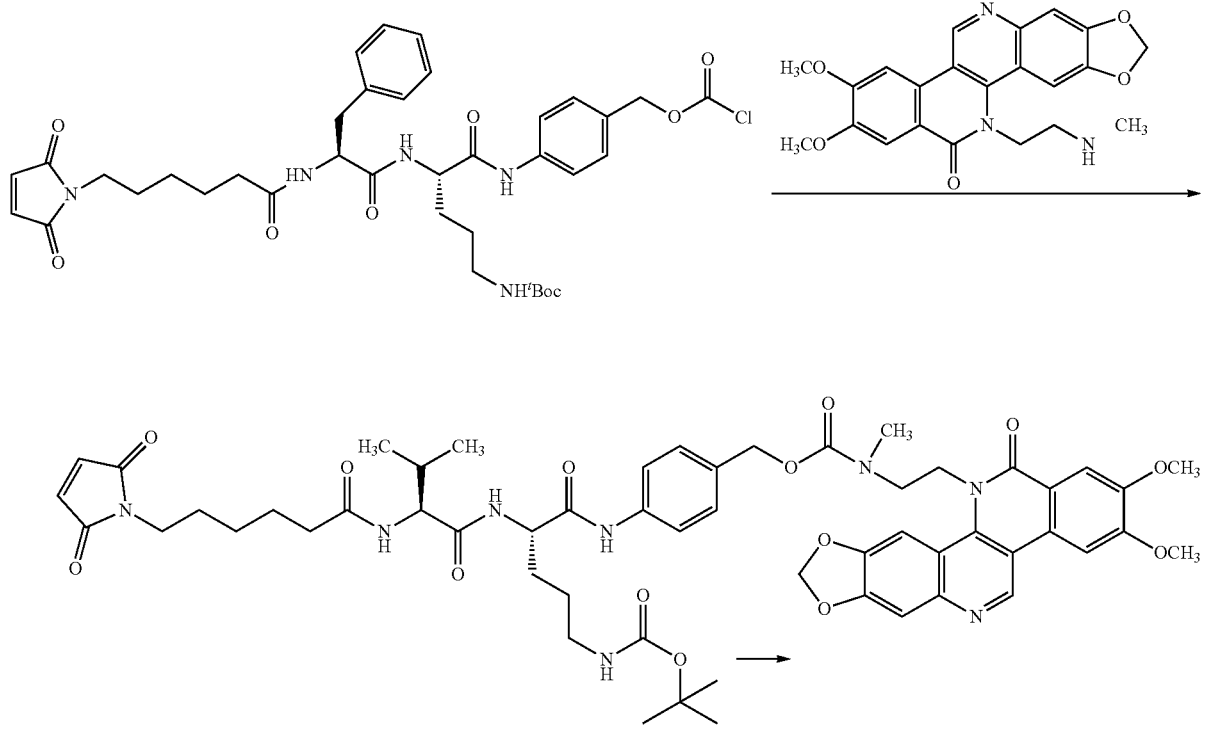

Compounds of formula I (ADCs) can also be formed by linking a cysteine residue of an antibody to an drug linker intermediate comprising a disulfide moiety and a residue of a compound of formula II. Examples of such intermediates are also embodiments of the invention and are described herein below. These intermediates comprise a compound of formula II with a linker comprising a disulfide bond. Such intermediates can be reacted with a cysteine residue of a biomolecule such as an antibody to form a compound of formula I. Scheme 18 shows non-limiting examples of such intermediates (drug linker intermediates).

Scheme 18

Intermediates for conjugating antiboides -- cysteine bsedA

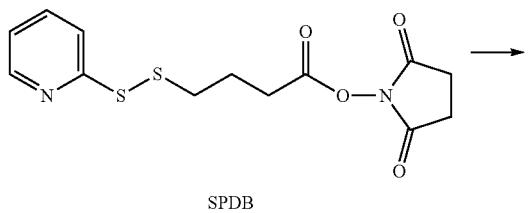

SPDB

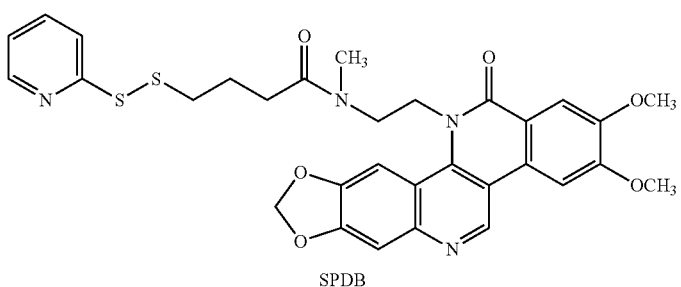

SPDB

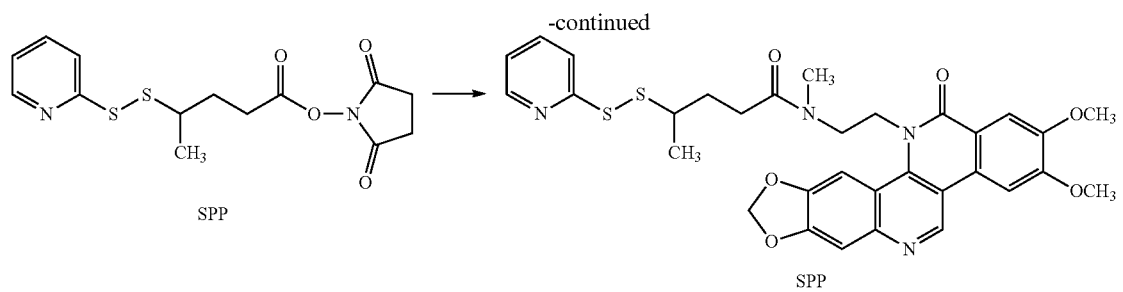
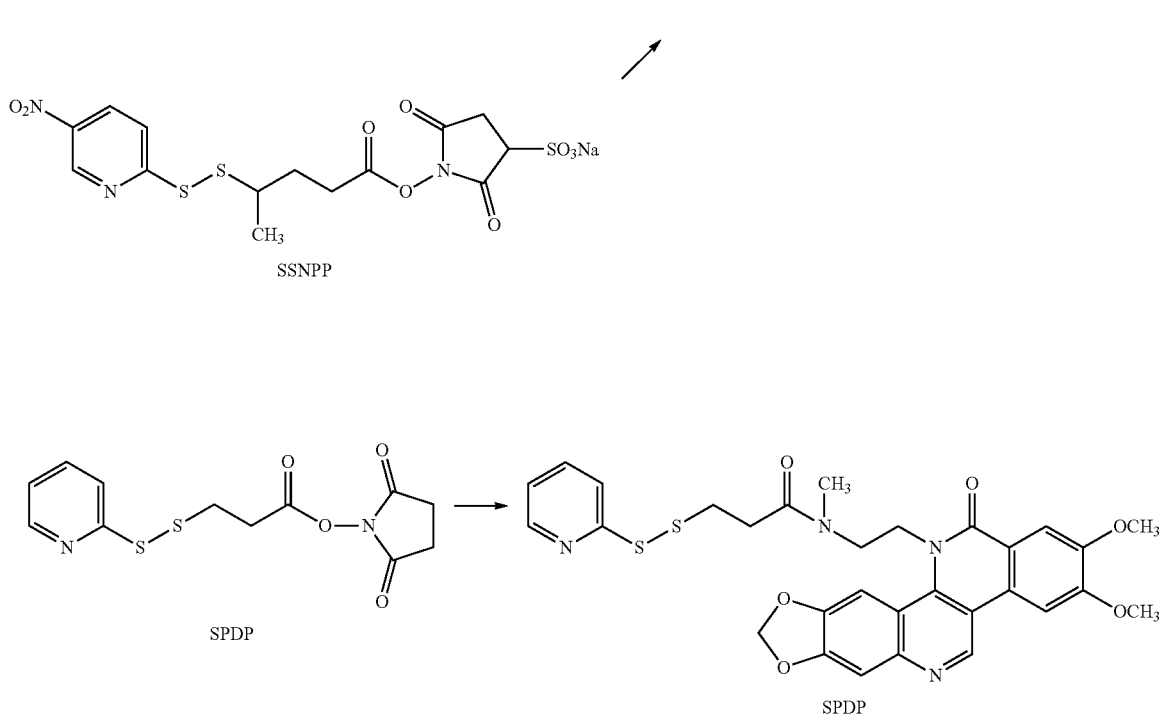
Schemes 19-23 illustrate general methods for preparing intermediates that can form a cysteine-linkage to a tumor-selective antibody.
Scheme 19
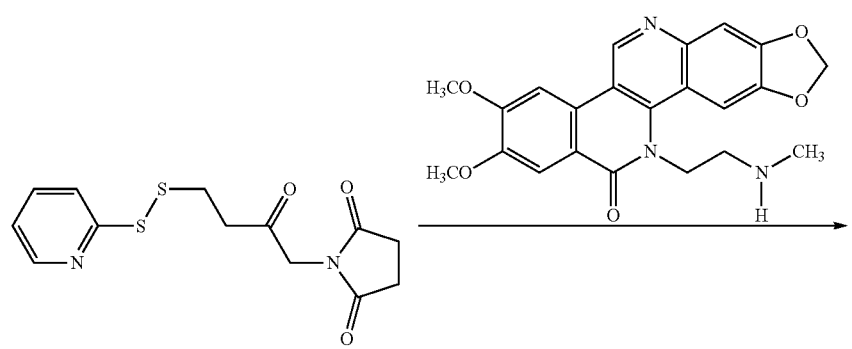

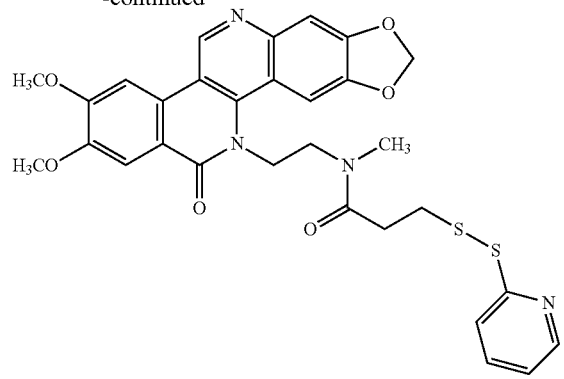
-continued
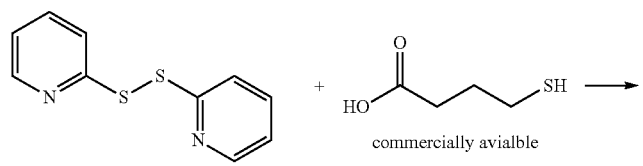
Scheme 20
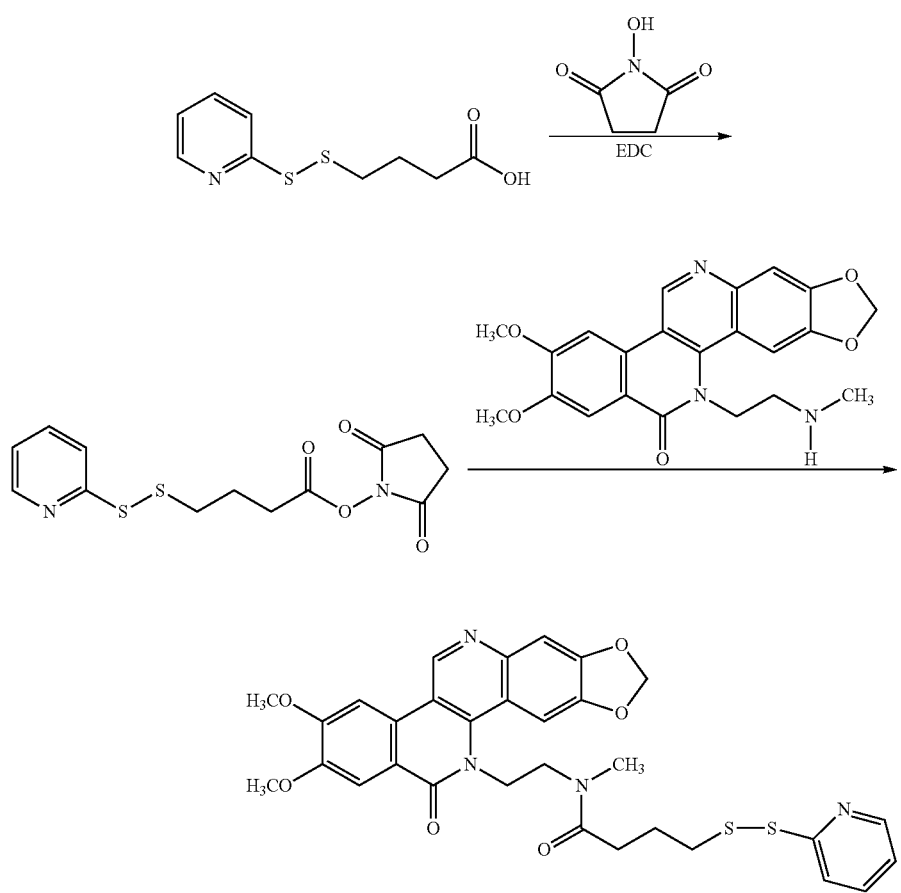

Scheme 21
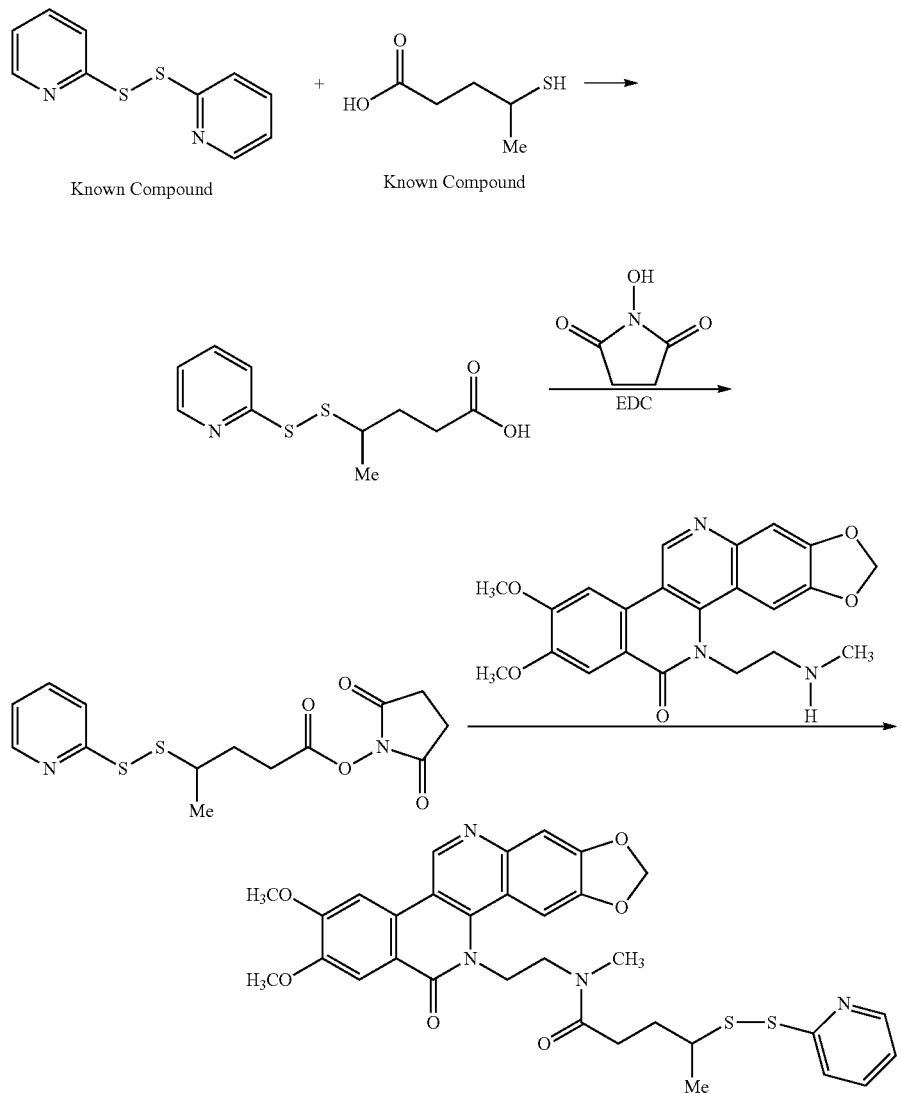
Scheme 22
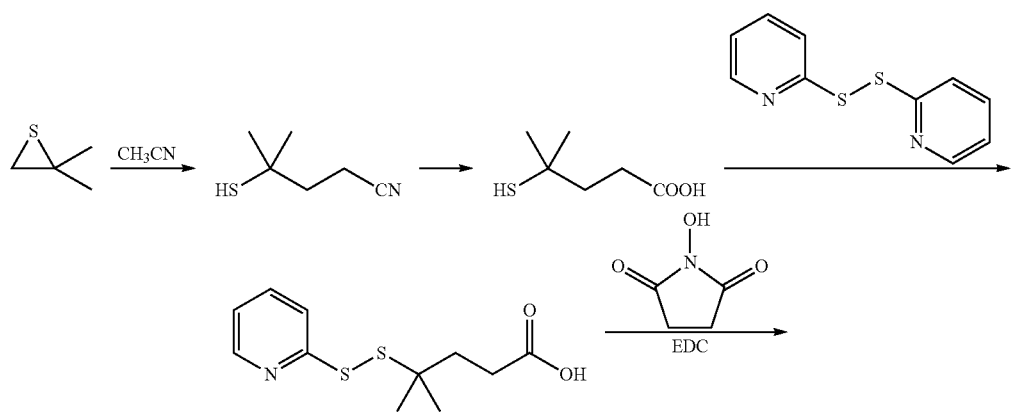

-continued
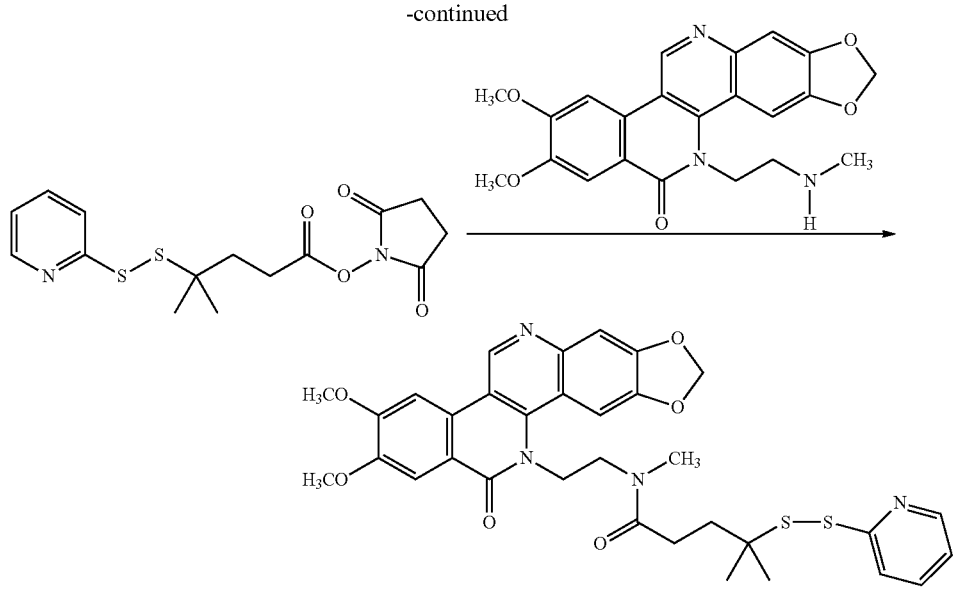
Scheme 23
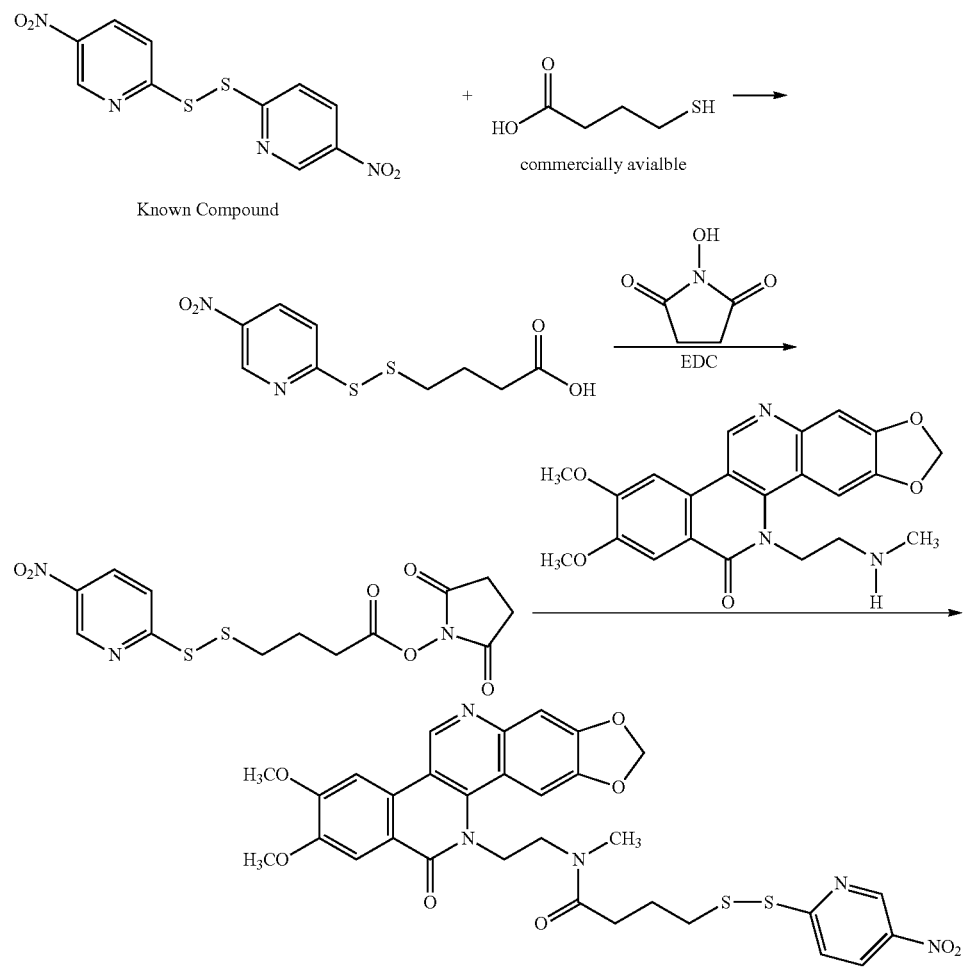

The drug linker intermediates (intermediates) described in Schemes 14-23 can be used to prepare compounds of formula I (ADCs of formula I). The structures of Schemes 24 and 25 represent non-limiting compounds of formula I (ADCs of formula I) are thus embodiments of the invention.
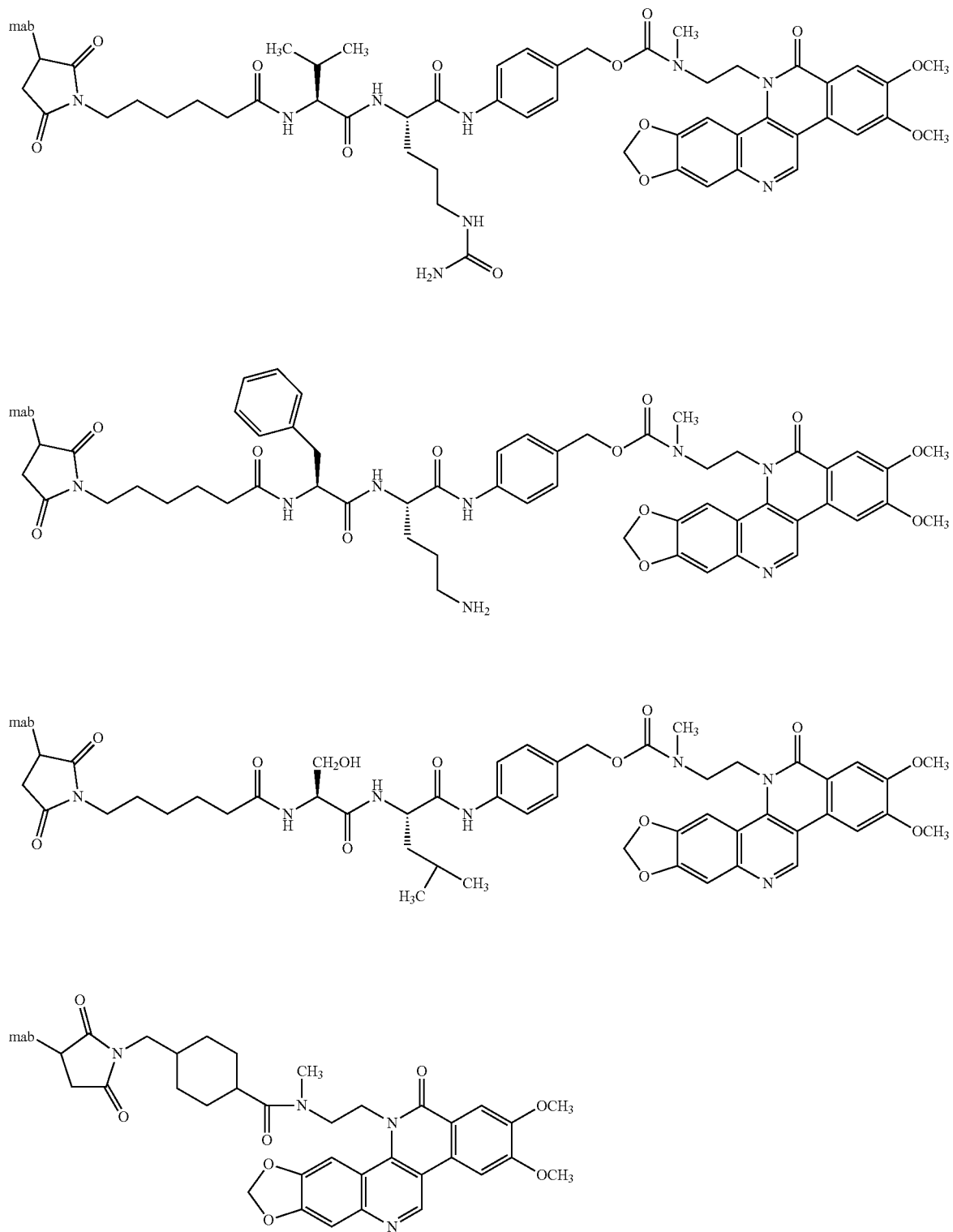
Scheme 24

Scheme 25

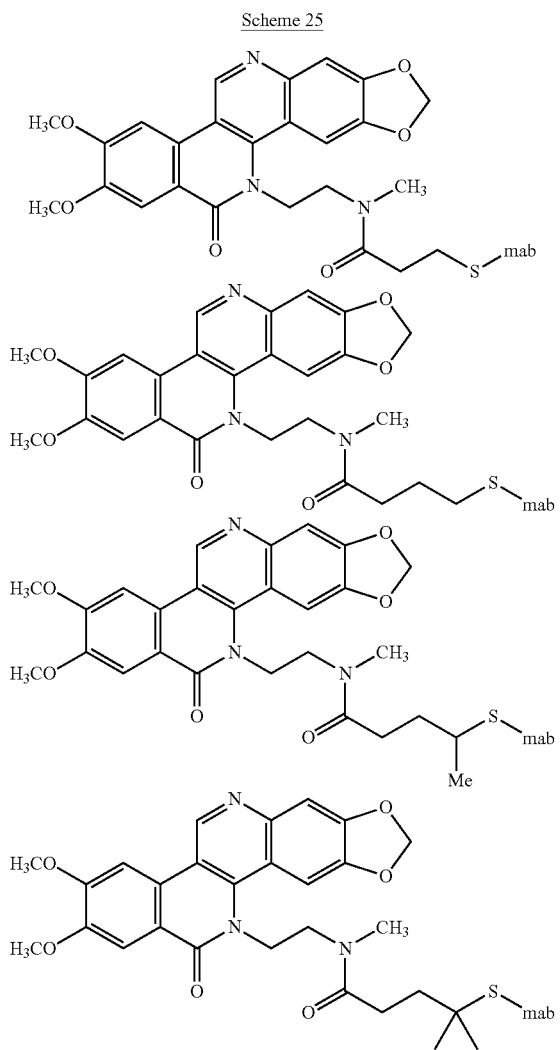

Pharmaceutically acceptable salts may be obtained using standard procedures well known in the art, for example by reacting a sufficiently basic compound such as an amine with a suitable acid affording a physiologically acceptable anion. Alkali metal, for example, sodium, potassium or lithium, or alkaline earth metal, for example calcium, salts of carboxylic acids can also be made.

The compounds of the invention can be formulated as pharmaceutical compositions and administered to a mammalian host, such as a human patient in a variety of forms adapted to the chosen route of administration, that is, orally or parenterally, by intravenous, intramuscular, topical or subcutaneous routes. Typically the compounds will be administered by infusion.

Thus, the present compounds may be systemically administered, for example, orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compound may also be administered intravenously or intraperitoneally by infusion or injection. Solutions of the compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The in vivo antitumor activity of a compound of the invention can be determined using pharmacological models that are well known in the art, for example, using a model like Test A described below.

Test A. Human Tumor Xenograft Assay

Bioassays are performed using female NCR/NU NU mice of approximately 9 weeks of age as obtained from Taconic Farms, Inc. (Germantown, N.Y., USA). Mice are housed 4 per cage in laminar flow HEPA filtered microisolator caging (Allentown Caging Equipment Co., Allentown, N.J., USA). Mice are fed Purina autoclavable breeder chow #5021 and given drinking water, purified by reverse-osmosis, ad libitum. Five days after arrival within the animal facility, the mice are inoculated on the right flank with $1.5 \times 10^6$ MDA-MB-435 tumor cells in 0.1 mL of RPMI 1640 Media by sc injection (25 gauge needle×⅝"). The MDA-MB-435 cells are grown in 75 $cm^2$ flasks using RPMI 1640 Media and 10% fetal bovine serum. Tumors are of sufficient size at 19-20 days after inoculation. Tumor-bearing mice are evenly matched in each experimental group based on tumor volume. Tumor volume is calculated by measuring the tumor with a microcaliper. The length (l) is the maximum two dimensional distance of the tumor and the width (w) is the maximum distance perpendicular to this length measured in mm. Tumor volume is calculated using the formula $(l \cdot w^2)/2$. Every mouse is weighed individually on a daily basis. Dose adjustments for each experimental group can be made throughout the study based upon the effect or lack of an effect of treatment on average body weights. Tumor volume is determined for each individual mouse every other day.

The ability of a compound described herein to be actively transported can be determined using pharmacological models that are well known in the art, for example, using a model like test B described below.

Test B. Efflux Assay

The cytotoxicity of the representative compounds of the invention were also tested against cell line KB3-1 (parent cell line), KBV-1 (a variant that overexpresses efflux transporter MDR1) and KBH5.0 (a variant that overexpresses BCRP). Differences in the relative cytotoxicity between the parent and variant cell lines may be indicative of a compound that is a substrate for an efflux transporter. These data suggest that the compounds tested may be substrates to varying degrees for MDR1 and BCRP and that the compound of Example 2 is not a substrate for BCRP. Accordingly, compounds of the invention may be useful to treat tumors that are resistant to other anticancer agents, including anticancer agents that are susceptible to efflux by BCRP (e.g. anthracyclines, mitoxantrone, topotecan, irinotecan, bisanthrone, doxorubicin, daunorubicin, and epirubin.

Topoisomerase inhibitors are also known to possess antifungal, antipsoritic (psoriasis), antiprotozoal, antihelmetic, and antiviral activity. Accordingly, the topoisomerase inhibitor prodrug of formula II (i.e., the compound of formula I) of the invention may also be useful as, antifungal, antipsoritic (psoriasis), antiprotozoal, antihelmetic, or antiviral agents. Thus, certain compounds of formula I may be particularly useful as systemic antifungal, antipsoritic (psoriasis), antiprotozoal, antihelmetic, or antiviral agents in mammals. One embodiment provides the use of a compound of formula I or a pharmaceutically acceptable salt thereof for the manufacture of a medicament useful for producing an antifungal, antipsoritic (psoriasis), antiprotozoal, antihelmetic, or antiviral effect in a mammal.

As used herein, the term "solid mammalian tumors" include cancers of the head and neck, lung, mesothelioma, mediastinum, esophagus, stomach, pancreas, hepatobiliary system, small intestine, colon, rectum, anus, kidney, ureter, bladder, prostate, urethra, penis, testis, gynecological organs, ovarian, breast, endocrine system, skin central nervous system; sarcomas of the soft tissue and bone; and melanoma of cutaneous and intraocular origin. The term "hematological malignancies" includes childhood leukemia and lymphomas, Hodgkin's disease, lymphomas of lymphocytic and cutaneous origin, acute and chronic leukemia, plasma cell neoplasm and cancers associated with AIDS. The preferred mammalian species for treatment are humans and domesticated animals.

The invention will now be illustrated by the following non-limiting Examples.

EXAMPLE 1

Preparation of Compound 1

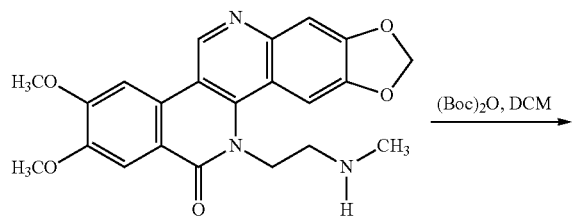

2,3-Dimethoxy-12-(2-(methylamino)-ethyl)[1,3]dioxolo[4',5':4,5]-benzo[1,2-h]benzo[c][1,6]naphthyridin-13(12H)-one

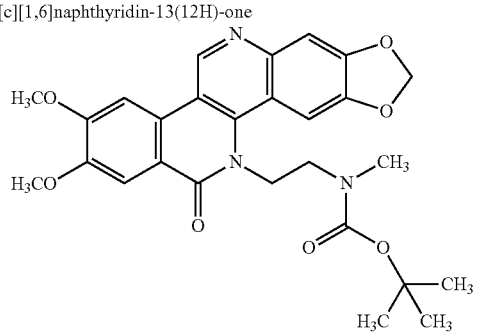

1

To a partial solution of 2,3-dimethoxy-12-(2-(methylamino)ethyl)-[1,3]dioxolo[4',5':4,5]-benzo[1,2-h]benzo[c][1,6]naphthyridin-13(12H)-one (100 mg, 0.24 mmol) in methylene chloride (5 mL) was added (Boc)$_2$O (65 mg, 0.29 mmol) at room temperature. The reaction mixture immediately became soluble and thin-layer chromatography showed total consumption of the starting material. The solvent was removed and the crude mixture was purified using ISCO column chromatography on silica to afford the desired product as a white solid (72 mg, 59% yield). $^1$HNMR (300 mHz, CDCl$_3$) d: 9.4 (s, 1H), 7.96 (s, 1H), 7.7 (s, 1H), 7.5 (s, 1H), 7.32 (s, 1H), 6.2 (s, 2H), 4.8 (m, 2H), 4.15 (s, 3H), 4.08 (s, 3H), 3.9 (m, 1H), 3.7 (s, 1H), 2.7 (s, 3H), 1.4 (m, 9H).

EXAMPLE 2

Preparation of Compound 2

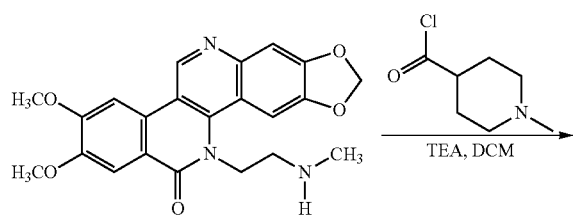

2,3-Dimethoxy-12-(2-(methylamino)-ethyl)[1,3]dioxolo[4',5':4,5]-benzo[1,2-h]benzo[c][1,6]naphthyridin-13(12H)-one

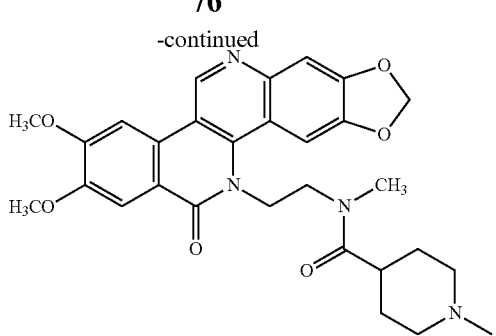

2

To a partial solution of 2,3-dimethoxy-12-(2-(methylamino)ethyl)-[1,3]dioxolo[4',5':4,5]-benzo[1,2-h]benzo[c][1,6]naphthyridin-13(12H)-one (33 mg, 0.08 mmol) in DCM (3 mL) was added triethylamine (0.025 ml, 0.162 mmol) followed by 1-methylpiperidine-4-carbonyl chloride (33 mg) at −78° C. The reaction mixture was then allowed to warm to room temperature at which time TLC showed total consumption of the starting material. The reaction mixture was diluted with dichloromethane and was washed with NaHCO$_3$ and brine. The organic layers were dried, evaporated under reduced pressure and the crude residue was purified using ISCO chromatography on silica to afford the product as white solid (22 mg, 51% yield). $^1$HNMR (300 mHz, CDCl$_3$) d: 9.38 (s, 1H), 7.96 (s, 1H), 7.87 (s, 1H), 7.38 (s, 1H), 7.36 (s, 1H), 6.19 (s, 2H), 4.7 (m, 2H), 4.13 (s, 3H), 4.05 (s, 3H), 3.9 (m, 1H), 3.7 (s, 1H), 2.95 (m, 4H), 2.8 (s, 4H), 2.1 (m, 1H), 1.6 (m, 4H).

EXAMPLE 3

Preparation of Compound 3

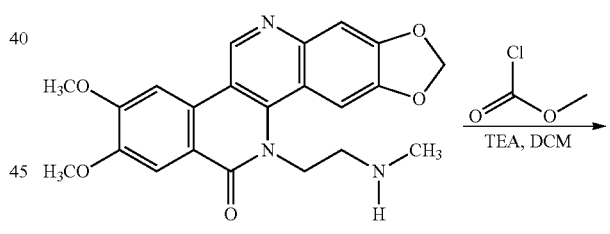

2,3-Dimethoxy-12-(2-(methylamino)-ethyl)[1,3]dioxolo[4',5':4,5]-benzo[1,2-h]benzo[c][1,6]naphthyridin-13(12H)-one

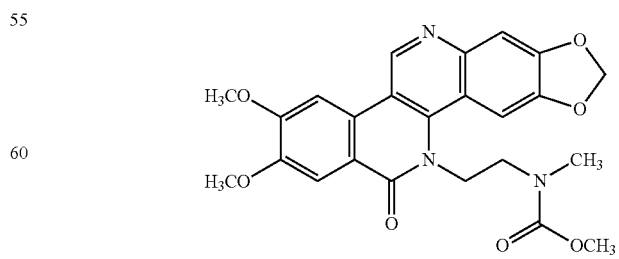

3

To a partial solution of Gen 644282 (25 mg, 0.06 mmol) in methylene chloride (3 mL) was added triethylamine (0.017 ml, 0.12 mmol) followed by methyl carbonochloridate (0.010 ml) at −78° C. The reaction mixture was then allowed to warm to room temperature at which time analysis by thin-layer chromatography showed total consumption of the starting material. The reaction mixture was diluted with DCM and was washed with NaHCO3 and brine. The organic layers were dried, evaporated under vacuum the crude mixture was purified using ISCO column chromatography on silica to afford the desired product as white solid (20 mg, 71% yield). $^1$HNMR (300 mHz,CDCl$_3$) d: 9.4 (s, 1H), 7.90 (s, 1H), 7.8 (s, 1H), 7.7 (s, 1H), 7.5 (d, 1H), 6.19 (s, 2H), 4.7 (m, 2H), 4.16 (s, 3H), 4.09 (s, 3H), 4.0-3.9 (m, 2H), 3.7 (d, 3H), 3.0 (s, 3H).

EXAMPLE 4

Preparation of Compound 4

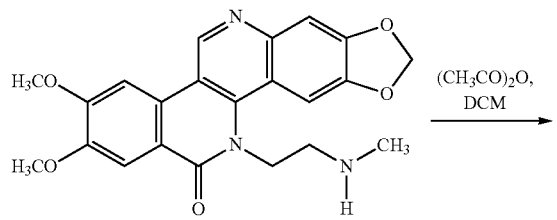

2,3-Dimethoxy-12-(2-(methylamino)-ethyl)[1,3]dioxolo[4′,5′:4,5]-benzo[1,2-h]benzo[c][1,6]naphthyridin-13(12H)-one

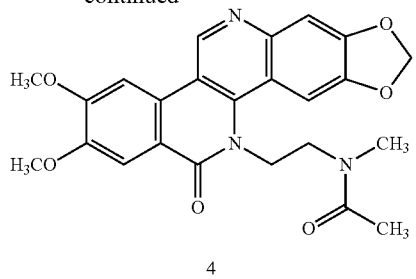

4

To a partial solution of 2,3-dimethoxy-12-(2-(methylamino)ethyl)[1,3]dioxolo[4′,5′:4,5]-benzo[1,2-h]benzo[c][1,6]naphthyridin-13(12H)-one (20 mg, 0.048 mmol) in DCM (2 mL) was added acetic anhydride (0.006 ml) at room temperature. The reaction mixture immediately became soluble and TLC showed total consumption of the starting material. The solvent was removed and the crude mixture was purified by ISCO column chromatography to afford product as white solid (12 mg, 52% yield). $^1$HNMR (300 mHz,CDCl$_3$) d: 9.4 (s, 1H), 8.35 (s, 1H), 7.94 (s, 1H), 7.7 (s, 1H), 7.42 (s, 1H), 6.23 (s, 2H), 4.68 (m, 2H), 4.14 (s, 3H), 4.07 (s, 3H), 3.9 (m, 2H), 3.17 (s, 3H), 2.07 (s, 3H).

EXAMPLE 5

Preparation of Compound 7

Compound 7 is useful for the conjugation of the TOP1-targeting agent II to antibodies via a Val-Cit Cleavable linker.

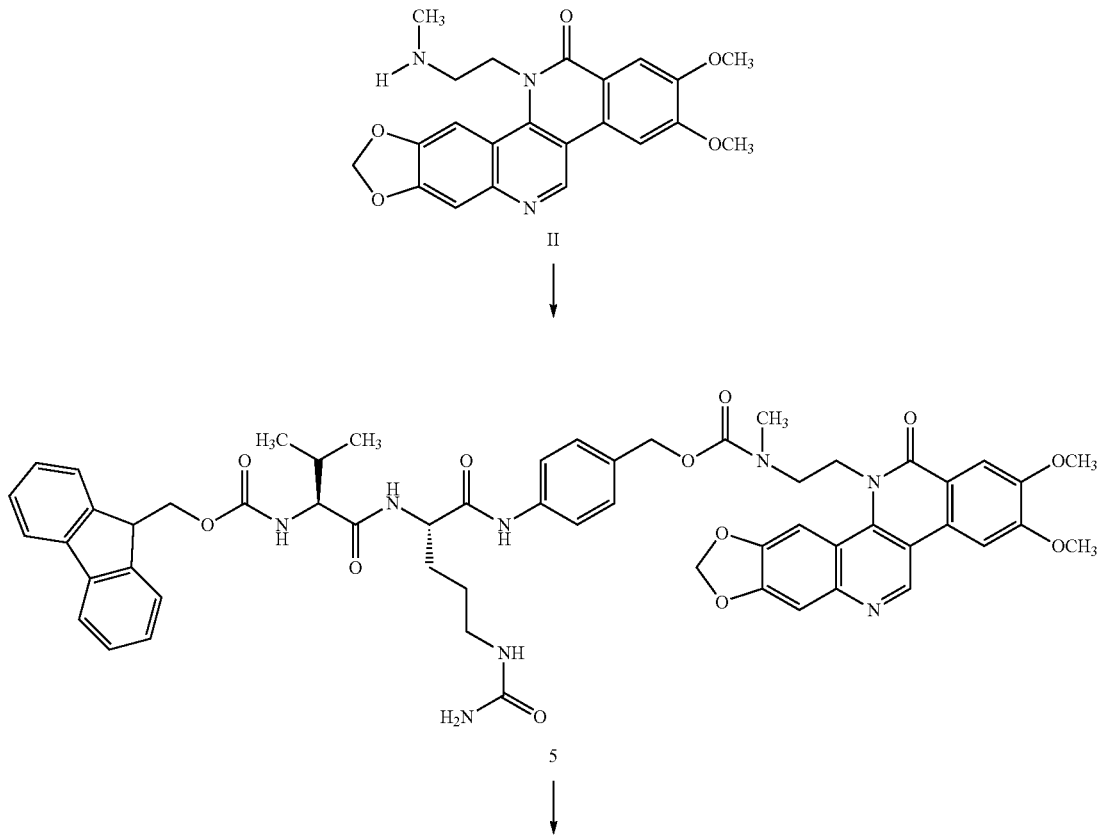

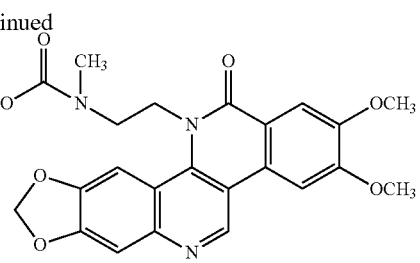

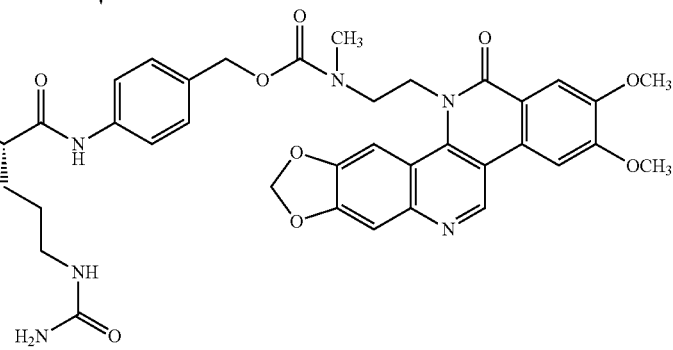

2,3-Dimethoxy-12-(2-(methylamino)ethyl)[1,3]dioxolo[4',5':4,5]benzo[1,2-h]benzo[c][1,6]naphthyridin-13(12H)-one (II) has a secondary amine that could be acylated by Val-Cit-PABA linker. This linker (developed by Seattle Genetics Inc.) has been extensively used in ADC projects. It represents the only enzyme cleavable linker component for FDA approved ADCs. Compound 7 was utilized for a maleimide-sulfhydryl coupling between the partially reduced mAb and the maleimide of compound 7. The chemical synthesis of 7 follows the route published by Seattle Genetics Inc. (*Bioconjugate Chem.* 2002, 13:855-869; *Blood* 2003, 102:1458-1465; *Nature Biotech.*, 2003, 21:778-784).

The cytotoxic TOP-1 targeting agent II was coupled to Fmoc-Val-Cit-PABA-PNP (1 eq) in the presence of HOBt (1 eq) in DMF-2,6-lutidine (4/1, v/v) to provide compound 5. The reaction mixture was evaporated and treated with piperidine in DMF (20 v/v %) followed by semi-preparative reverse phase HPLC purification and lyophilization. Compound 6 was treated with 6-maleimidohexanoic acid succinate ester in DMF in the presence of DIPEA (2 eq). Compound 7 was purified by RP-HPLC and lyophilized. The final product was conjugated to the mAb previously reduced by dithiothreitol.

EXAMPLE 6

The following illustrate representative pharmaceutical dosage forms, containing a compound of the invention ('Compound X'), for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Injection 3 (1 mg/ml) | mg/ml |
|---|---|
| 'Compound X' (free base form) | 1.0 |
| Citric Acid | 0.1% |
| D5W | q.s. ad 1 mL |

| (vii) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

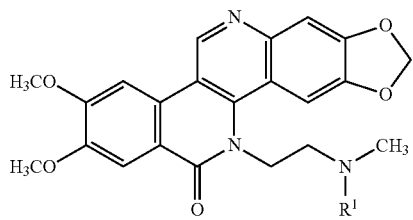

wherein $R^1$ is —C(=O)$R^a$, —C(=O)O$R^b$, a self-immolative moiety, or a linker substituted with one or more targeting moieties;

$R^a$ is $(C_1-C_6)$ alkyl, 5-6-membered monocyclic heterocycle, phenyl, or 5-6-membered monocyclic heteroaryl wherein any $(C_1-C_6)$ alkyl of $R^a$ is optionally substituted with one or more halogen, hydroxy, —O$(C_1-C_6)$ alkyl, COO$R^c$, or N$R^d R^e$ and any 5-6-membered monocyclic heterocycle, phenyl, or 5-6-membered monocyclic heteroaryl of $R^a$ is optionally substituted with one or more halogen, $R^f$, COO$R^c$, or N$R^d R^e$;

$R^b$ is $(C_1-C_6)$ alkyl, 5-6-membered monocyclic heterocycle, phenyl, or 5-6-membered monocyclic heteroaryl wherein any $(C_1-C_6)$ alkyl of $R^b$ is optionally substituted with one or more halogen, hydroxy, —O$(C_1-C_6)$ alkyl, COO$R^c$, or N$R^d R^e$ and any 5-6-membered monocyclic heterocycle, phenyl, or 5-6-membered monocyclic heteroaryl of $R^b$ is optionally substituted with one or more halogen, hydroxy, $R^f$, COO$R^c$, or N$R^d R^e$;

each $R^c$ is independently hydrogen or $(C_1-C_4)$alkyl;

each $R^d$ and $R^e$ is independently hydrogen or $(C_1-C_3)$ alkyl, or $R^d$ and $R^e$ together with the nitrogen to which they are attached form a 3-7 membered monocyclic heterocycle optionally substituted with one or more $(C_1-C_3)$alkyl; and each $R^f$ is independently $(C_1-C_6)$ alkyl or —O$(C_1-C_6)$ alkyl wherein any $(C_1-C_6)$alkyl or —O$(C_1-C_6)$ alkyl of $R^f$ is optionally substituted with one or more halogen, hydroxy, COO$R^c$, or N$R^d R^e$;

or a salt thereof.

2. The compound of claim 1, wherein $R^1$ is —C(=O)$R^a$ or —C(=O)O$R^b$.

3. The compound of claim 1, wherein $R^a$ is $(C_1-C_6)$ alkyl or a piperidinyl, wherein the piperidine is optionally substituted with one or more halogen, $(C_1-C_6)$ alkyl or —O$(C_1-C_6)$ alkyl.

4. The compound of claim 1 that is:

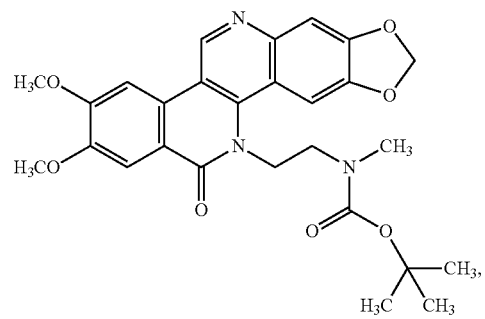

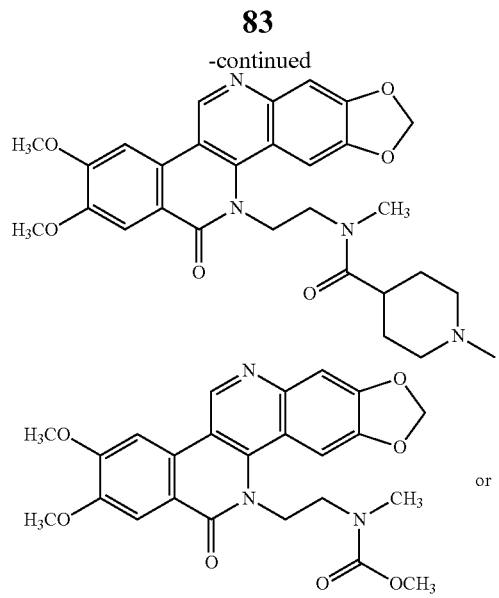
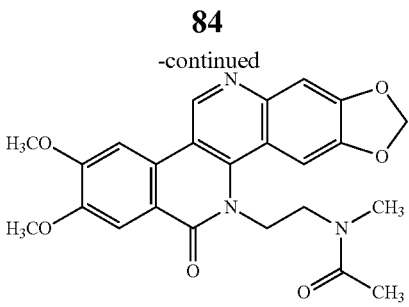
or a pharmaceutically acceptable salt thereof.
5. The compound of claim 1, wherein $R^1$ is a self-immolative moiety.
6. The compound of claim 1, wherein $R^1$ is a self-immolative moiety that is:
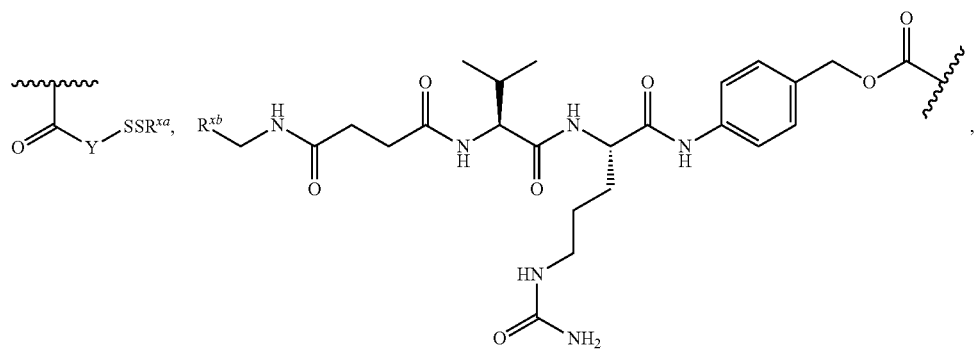
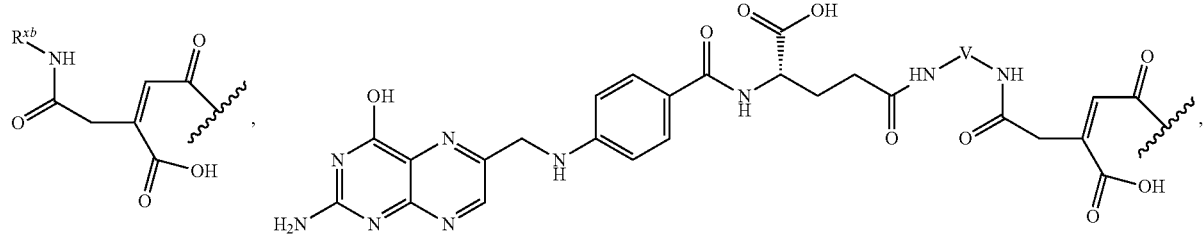
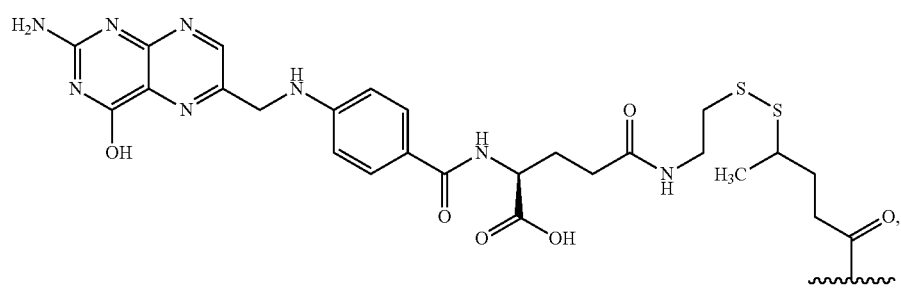

-continued

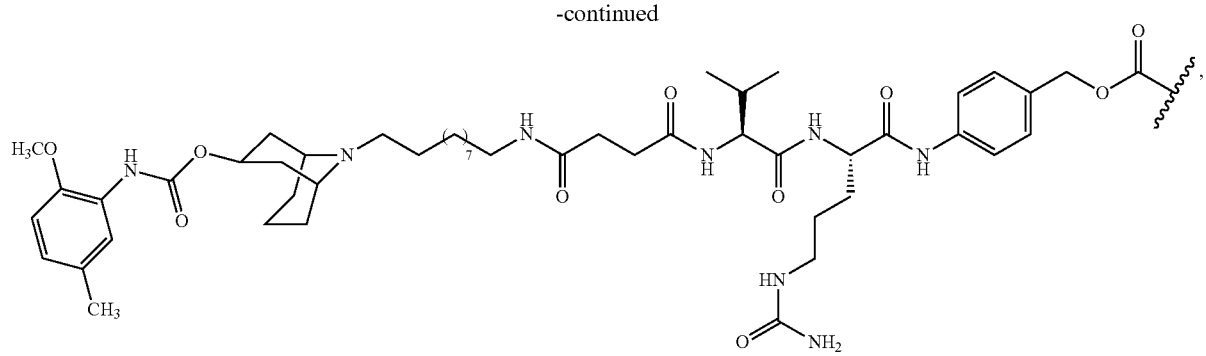

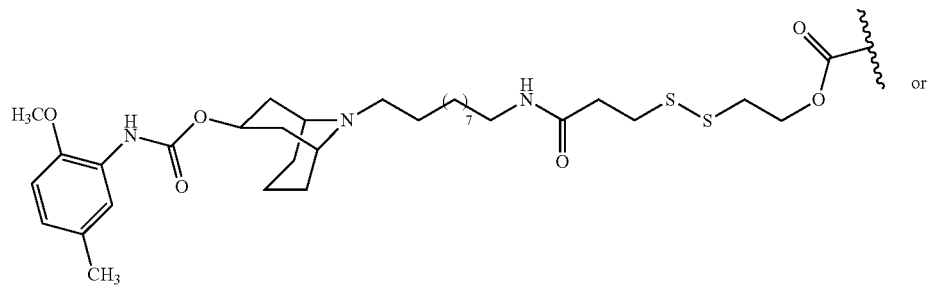

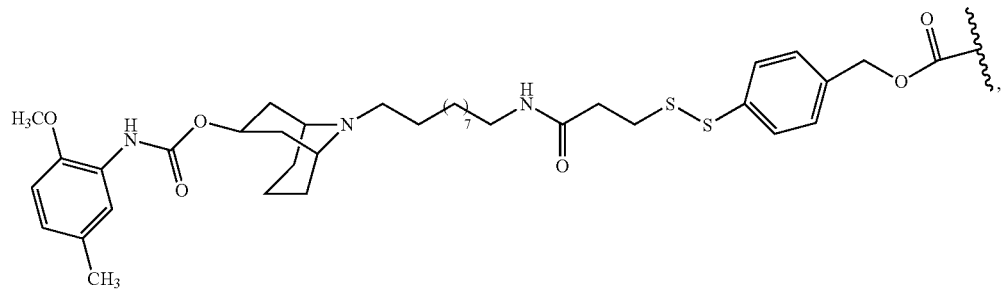

wherein Y is $(C_2-C_{10})$alkyl; V together with two nitrogen atoms as shown attached to V is a polyamine; $R^{xa}$ is $(C_1-C_{10})$alkyl, phenyl or 5-6-membered monocyclic heteroaryl, wherein any phenyl or 5-6-membered monocyclic heteroaryl of $R^{xa}$ is optionally substituted with one or more halogen, $(C_1-C_4)$alkyl or $(C_1-C_4)$alkyl; and $R^{xa}$ is $(C_1-C_{10})$ alkyl, $-O(C_1-C_{10})$alkyl, phenyl, or a 5-6-membered monocyclic heteroaryl, wherein any phenyl or 5-6-membered monocyclic heteroaryl of $R^{xa}$ is optionally substituted with one or more halogen, $(C_1-C_4)$alkyl, or $-O(C_1-C_4)$alkyl.

7. The compound of claim 1, wherein the compound of formula I is:

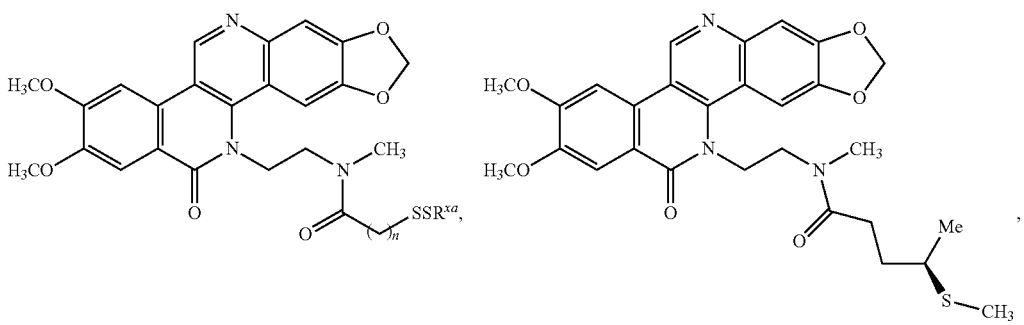

87 88
-continued
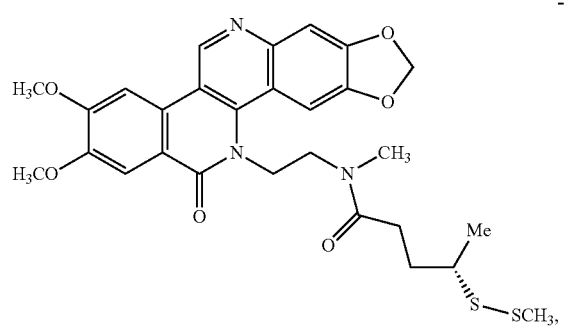
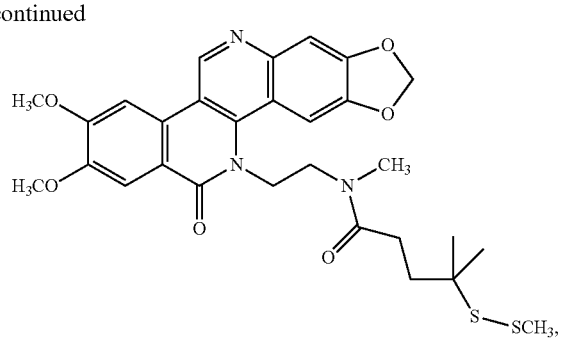
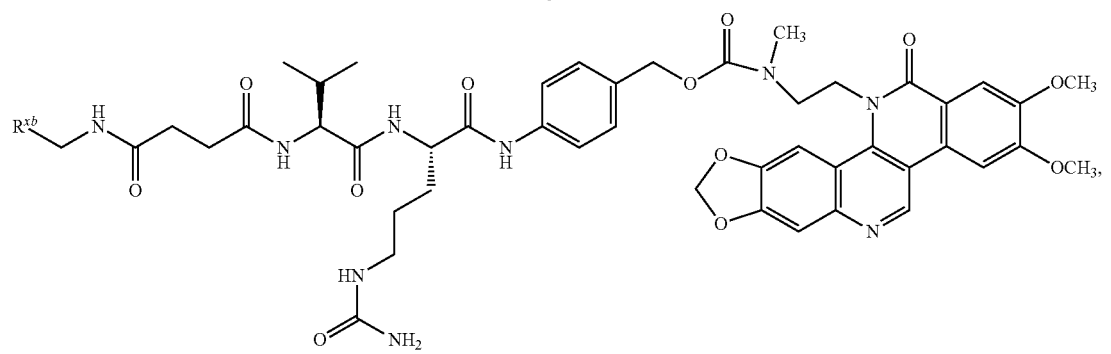
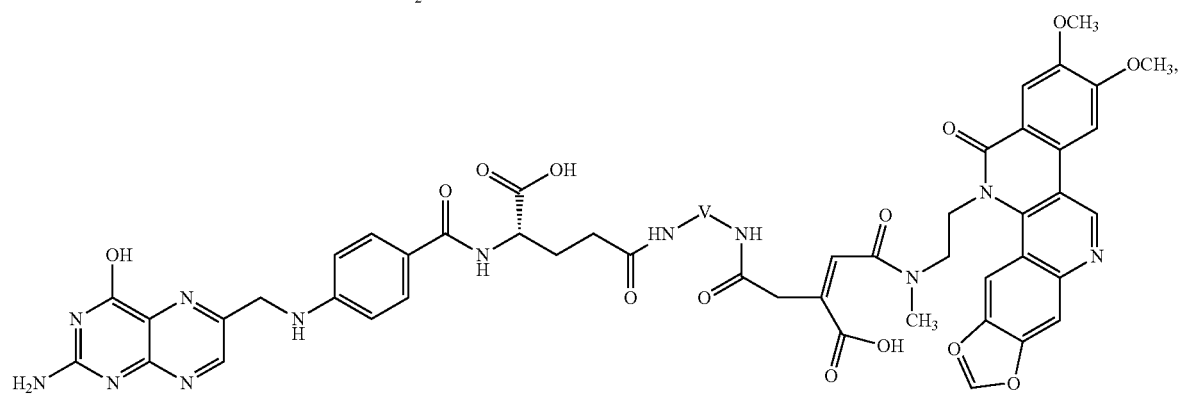
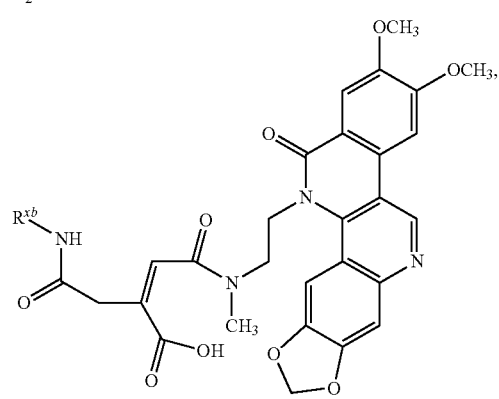
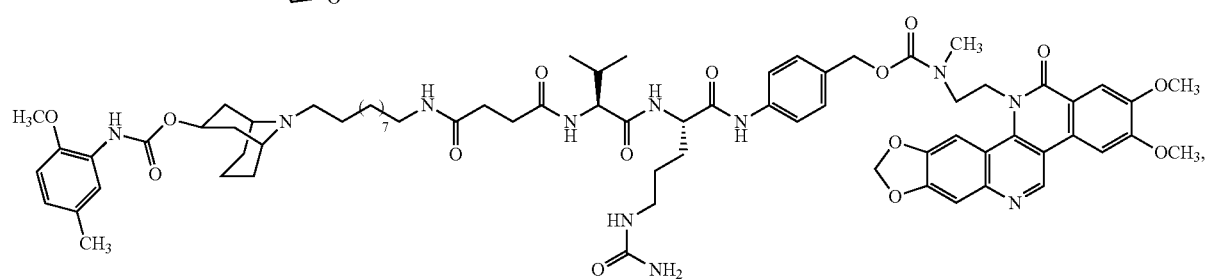

-continued

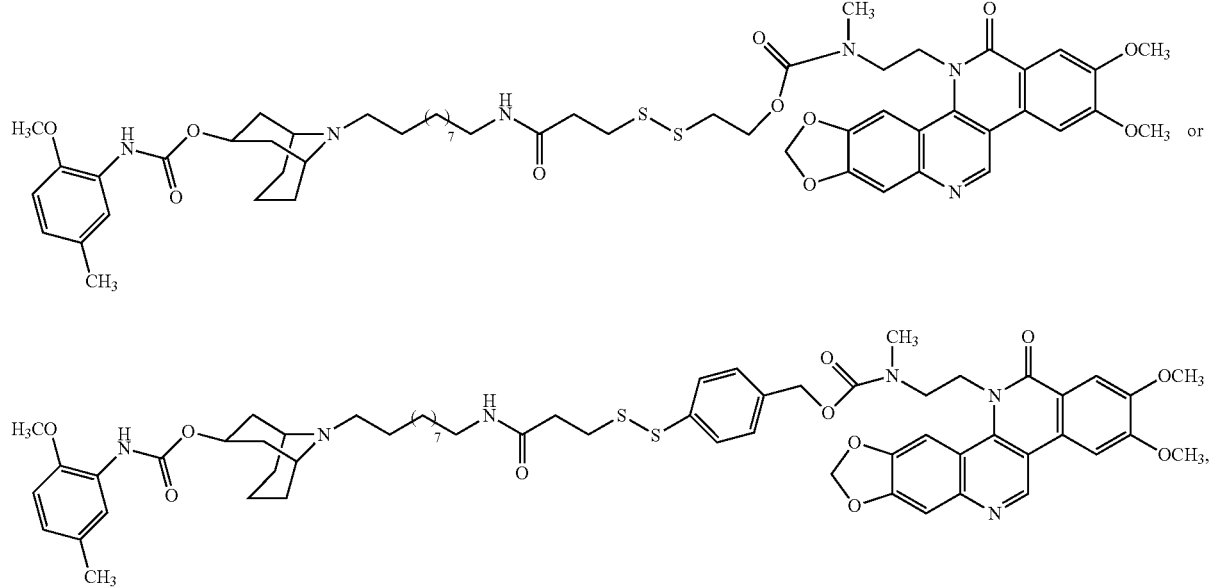

wherein n is 1, 2 or 3; $R^{xa}$ is $(C_1\text{-}C_{10})$alkyl, phenyl or 5-6-membered monocyclic heteroaryl, wherein any phenyl or 5-6-membered monocyclic heteroaryl of $R^{xa}$ is optionally substituted with one or more halogen, $(C_1\text{-}C_4)$alkyl or $(C_1\text{-}C_4)$alkyl; and $R^{xb}$ is $(C_1\text{-}C_{10})$alkyl, —O$(C_1\text{-}C_{10})$alkyl, phenyl, or a 5-6-membered monocyclic heteroaryl, wherein any phenyl or 5-6-membered monocyclic heteroaryl is optionally substituted with one or more halogen, $(C_1\text{-}C_4)$alkyl, or —O$(C_1\text{-}C_4)$alkyl; and V together with two nitrogen atoms as shown attached to V is a polyamine; or a pharmaceutically acceptable salt thereof.

8. The compound of claim 1, wherein $R^1$ is a self-immolative moiety that is:

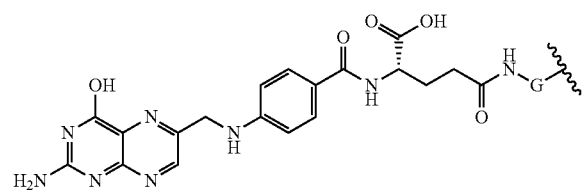

wherein G is a branched or unbranched, saturated or unsaturated, hydrocarbon chain, having from 2 to 25 carbon atoms, wherein one or more of the carbon atoms is optionally replaced by (—O—), (—NH—) or (—S—)and wherein the chain is optionally substituted on carbon with one or more substituents selected from $(C_1\text{-}C_6)$alkoxy, $(C_3\text{-}C_6)$cycloalkyl, $(C_1\text{-}C_6)$alkanoyl, $(C_1\text{-}C_6)$alkanoyloxy, $(C_1\text{-}C_6)$alkoxycarbonyl, $(C_1\text{-}C_6)$ alkylthio, cyano, nitro, halo, hydroxy, oxo (=O), carboxy, aryl, aryloxy, heteroaryl, and heteroaryloxy.

9. The compound of claim 1, wherein $R^1$ is a linker substituted with one or more targeting moieties.

10. The compound of claim 1, wherein the linker is a branched or unbranched, saturated or unsaturated, hydrocarbon chain, having from 2 to 60 carbon atoms, wherein one or more of the carbon atoms is optionally replaced by (—O—), phenyl, succinimdyl, or (—NH—) and wherein the chain is optionally substituted on carbon with one or more substituents selected from $(C_1\text{-}C_6)$alkoxy, $(C_3\text{-}C_6)$cycloalkyl, $(C_1\text{-}C_6)$alkanoyl, $(C_1\text{-}C_6)$alkanoyloxy, $(C_1\text{-}C_6)$alkoxycarbonyl, $(C_1\text{-}C_6)$alkylthio, oxo, azido, amino, cyano, nitro, halo, hydroxy, oxo (=O), carboxy, phenyl, phenoxy, 5-6-membered monocyclic heteroaryl, and 5-6-membered monocyclic heteroaryloxy.

11. The compound of claim 1, wherein the linker has a formula of:

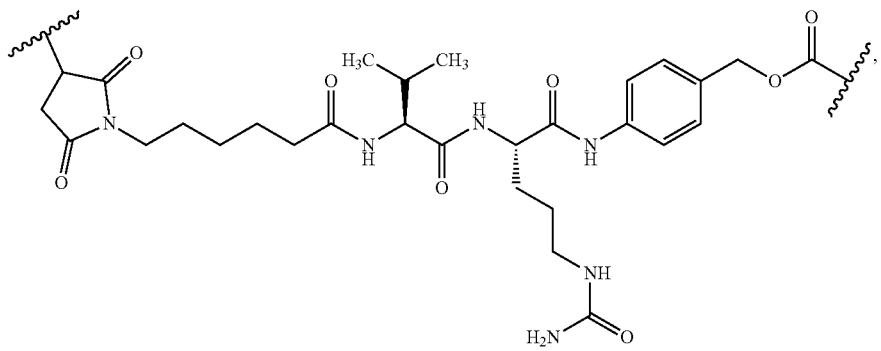

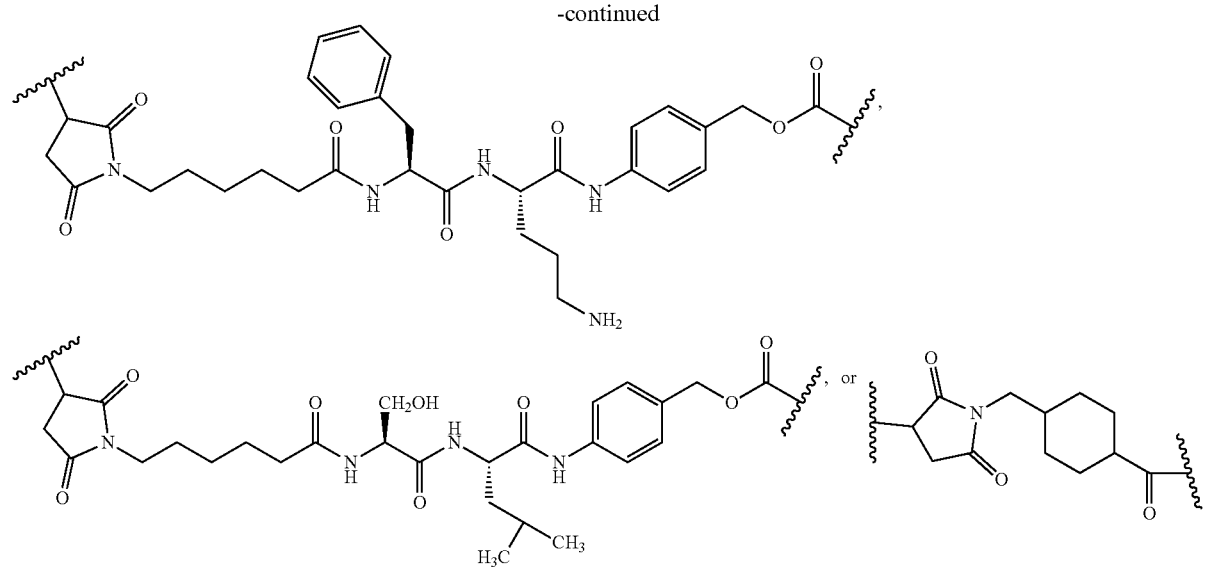

wherein the wavy line at the left depicts the point of attachment to the targeting moiety and wherein the wavy line at the right is the point of attachment to the remainder of the compound of formula I.

12. The compound of claim 1, wherein the linker has a formula of:

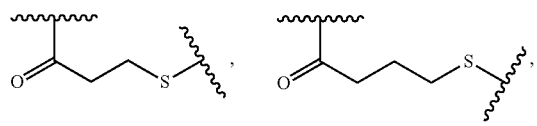

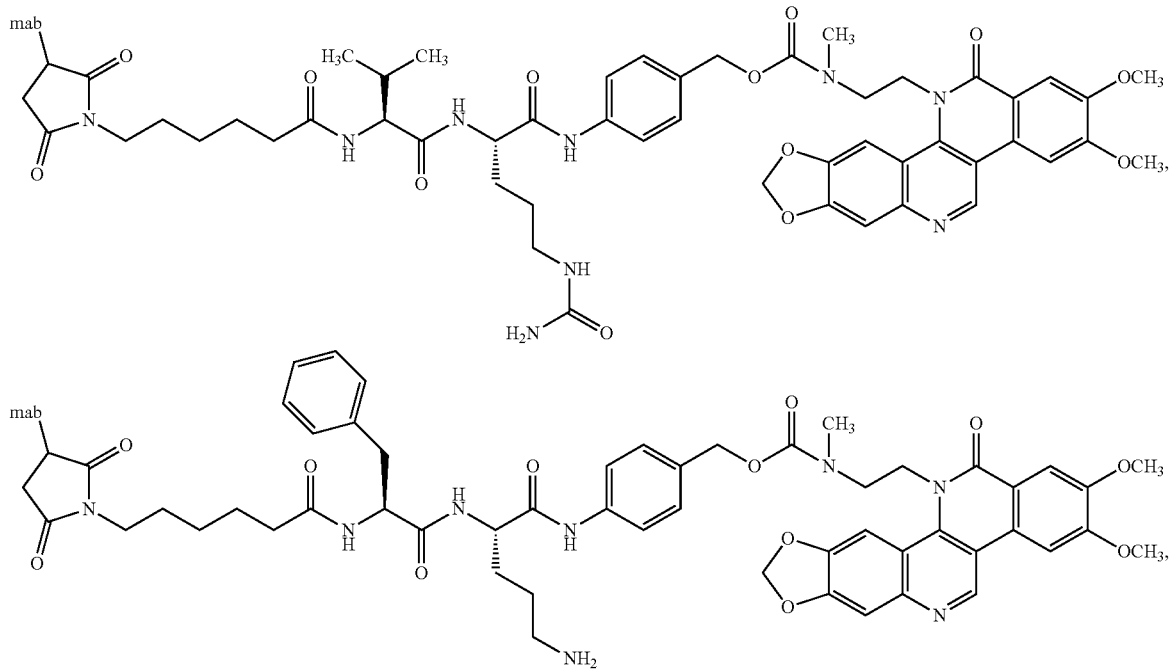

wherein the wavy line at the right depicts the point of attachment to the targeting moiety and wherein the wavy line at the left is the point of attachment to the remainder of the compound of formula I.

13. The compound of claim 1, wherein the targeting moieties are monoclonal antibodies (mab).

14. The compound of claim 1, wherein the compound of formula I is:

-continued

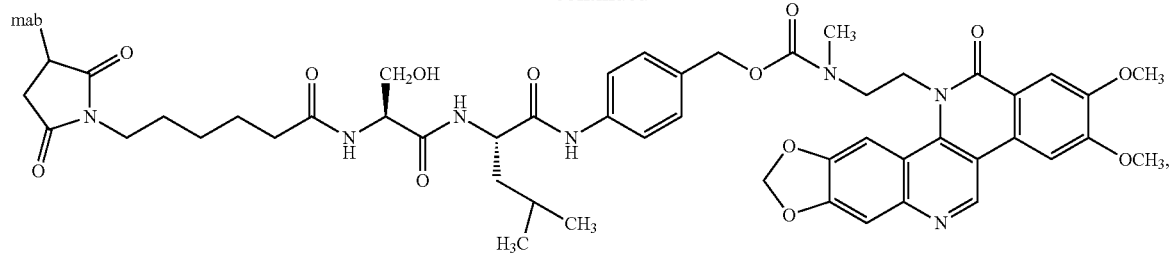

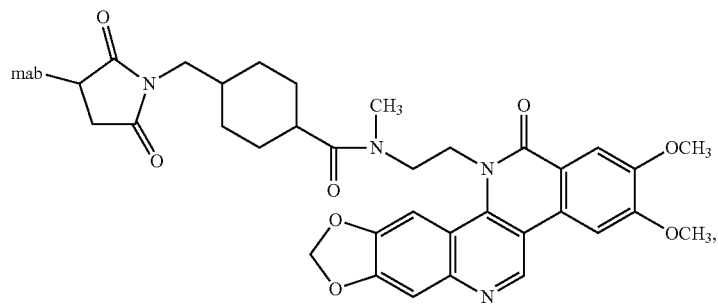

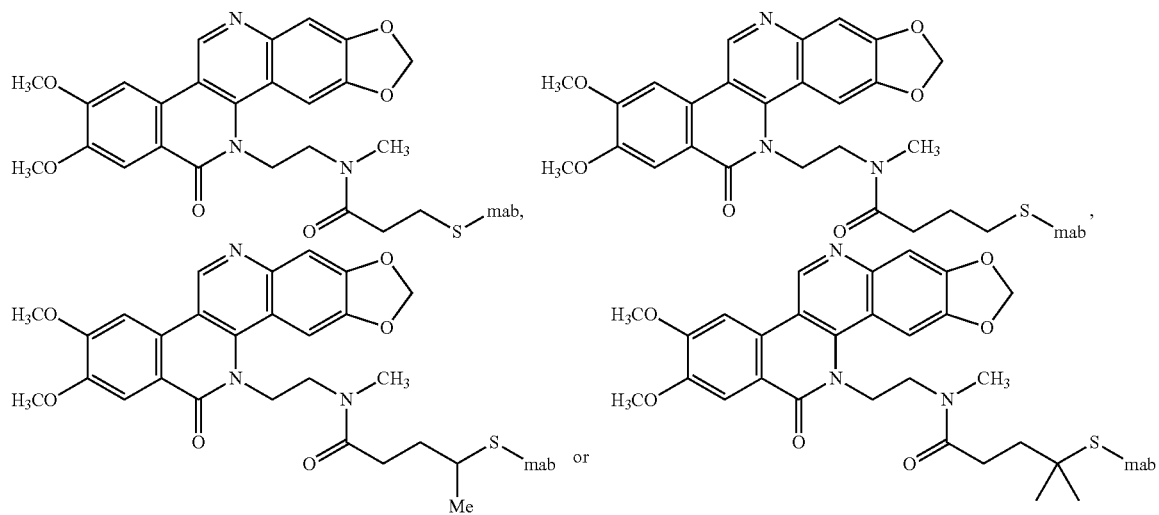

or a pharmaceutically acceptable salt thereof.

15. A pharmaceutical composition comprising a compound as described in claim 1 or a pharmaceutically acceptable salt thereof, and a pharmaceutically acceptable diluent or carrier.

16. A compound of formula III:

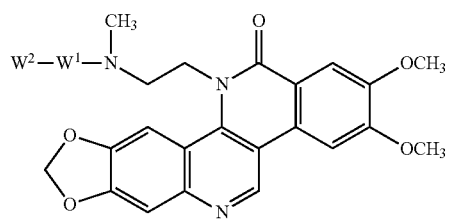

wherein $W^1$ is a linker;

$W^2$ is:

and $R^W$ is 5-6-membered monocyclic heteroaryl optionally substituted by one or more halogen, $NO_2$, or $(C_1-C_6)$ alkyl, wherein the alkyl is optionally substituted by one or more halogen;

or a salt thereof.

17. The compound of claim 16, wherein $W^1$ is:
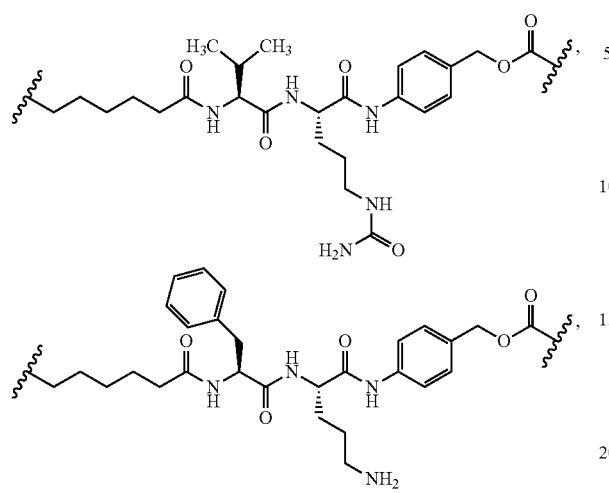
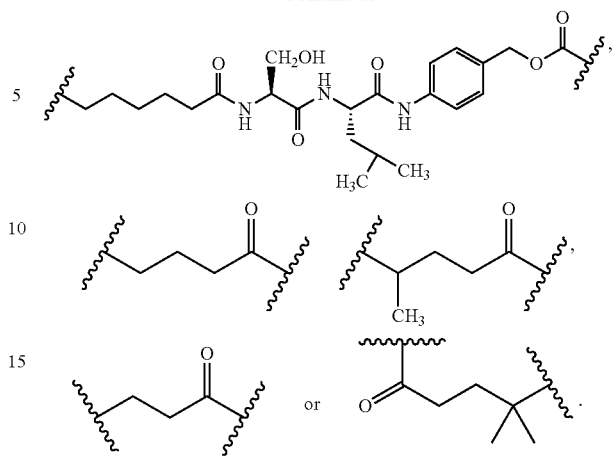
18. The compound of claim 16, wherein the compound of formula III is:
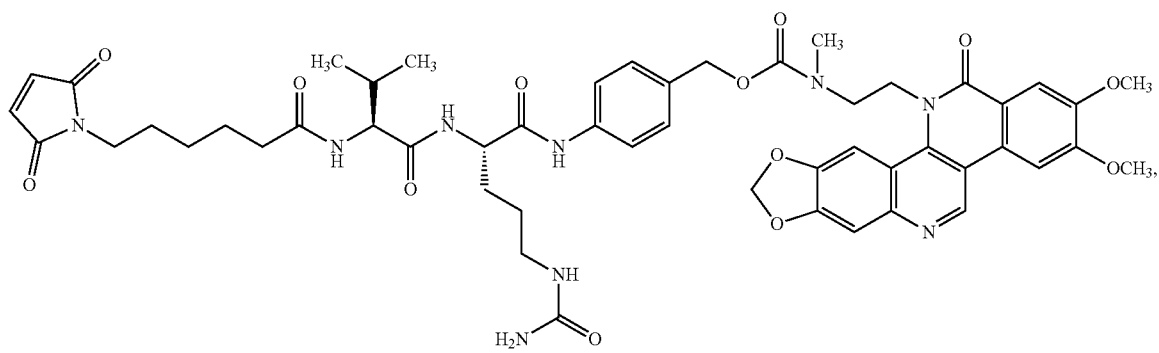
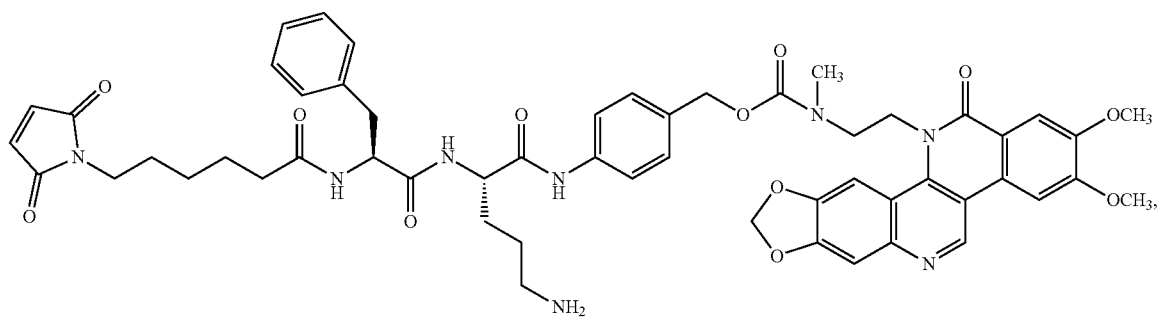
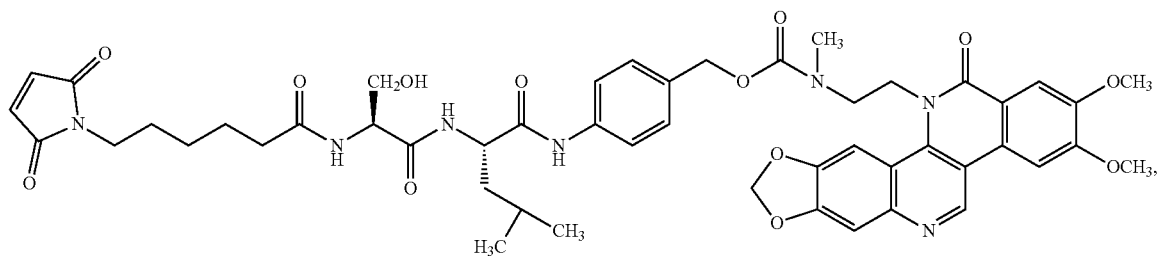

-continued
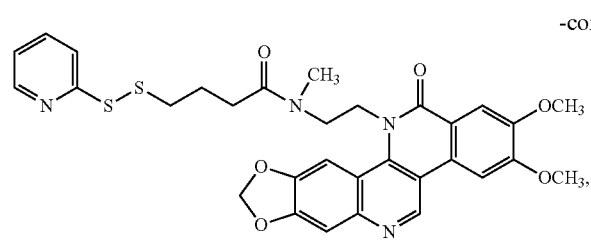
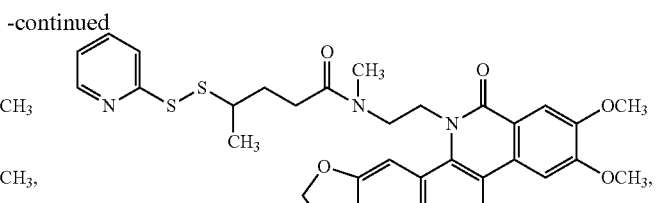
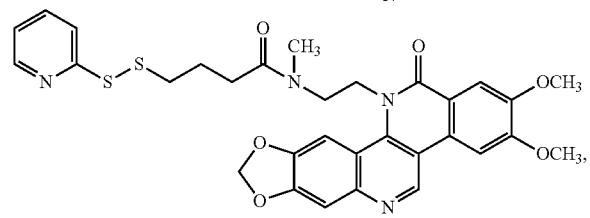
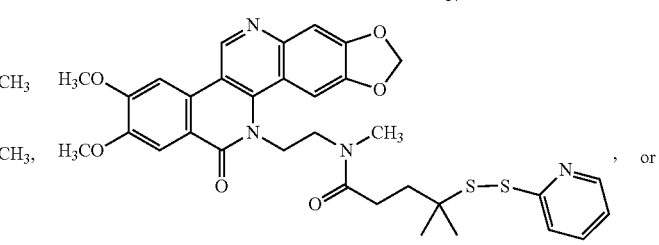
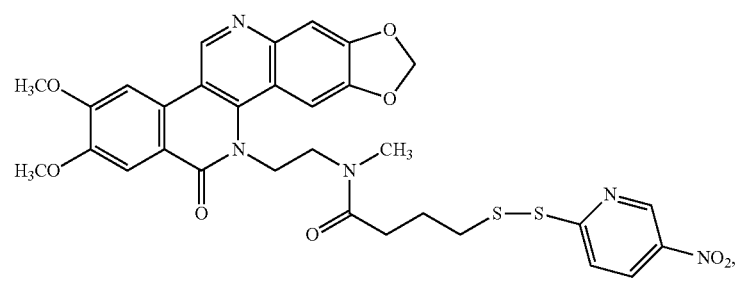
30
or a salt thereof.
* * * * *

UNITED STATES PATENT AND TRADEMARK OFFICE
CERTIFICATE OF CORRECTION

PATENT NO.      : 11,091,498 B2
APPLICATION NO. : 16/090802
DATED           : August 17, 2021
INVENTOR(S)     : Edmond J. LaVoie and Ajit K. Parhi Page 1 of 1

It is certified that error appears in the above-identified patent and that said Letters Patent is hereby corrected as shown below:

In the Claims

Column 87, third structure, Claim 7, please delete:

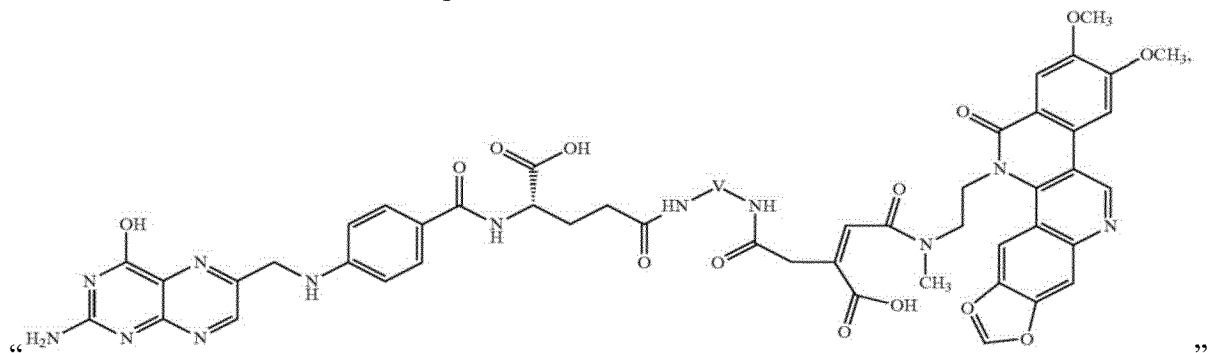

And insert:

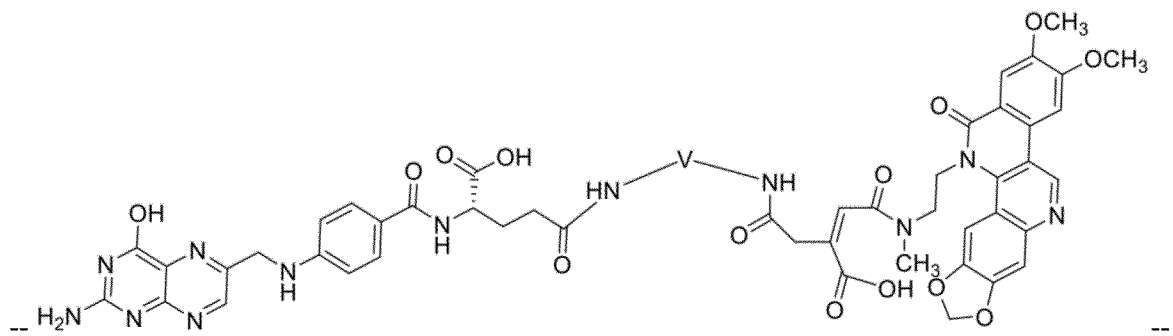

therefor.

Signed and Sealed this
Second Day of August, 2022

Katherine Kelly Vidal
*Director of the United States Patent and Trademark Office*